(12) United States Patent
Schmidt-Dannert et al.

(10) Patent No.: US 7,897,369 B2
(45) Date of Patent: Mar. 1, 2011

(54) ISOPRENOID WAX ESTER SYNTHASES, ISOPRENOID ACYL COA-SYNTHETASES, AND USES THEREOF

(75) Inventors: Claudia Schmidt-Dannert, St. Paul, MN (US); Erik K. Holtzapple, Davis, CA (US)

(73) Assignee: Regents of the University of Minnesota, St. Paul, MN (US)

( * ) Notice: Subject to any disclaimer, the term of this patent is extended or adjusted under 35 U.S.C. 154(b) by 0 days.

(21) Appl. No.: 12/199,439

(22) Filed: Aug. 27, 2008

(65) Prior Publication Data

US 2009/0117629 A1 May 7, 2009

Related U.S. Application Data

(60) Provisional application No. 60/966,272, filed on Aug. 27, 2007.

(51) Int. Cl.
| | |
|---|---|
| C12P 7/64 | (2006.01) |
| C12P 21/06 | (2006.01) |
| C12N 9/08 | (2006.01) |
| C12N 9/00 | (2006.01) |
| C12N 1/00 | (2006.01) |
| C12N 15/00 | (2006.01) |
| C12Q 1/48 | (2006.01) |
| C07H 21/04 | (2006.01) |

(52) U.S. Cl. ............... 435/134; 435/193; 435/183; 435/254.2; 435/69.1; 435/320.1; 435/15; 536/23.2

(58) Field of Classification Search ............ 435/134, 435/193, 183, 69.1, 254.2, 320.1, 15; 536/23.2
See application file for complete search history.

(56) References Cited

U.S. PATENT DOCUMENTS

| 4,703,004 A | 10/1987 | Hopp et al. |
| 4,782,137 A | 11/1988 | Hopp et al. |
| 5,594,115 A | 1/1997 | Sharma |
| 5,935,824 A | 8/1999 | Sgarlato |
| 6,165,757 A | 12/2000 | Ykema et al. |
| 7,118,896 B2 | 10/2006 | Kalscheuer et al. |
| 2008/0171378 A1 | 7/2008 | Keasling et al. |

FOREIGN PATENT DOCUMENTS

WO WO 2007/136762 A2 11/2007

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Guo et al., Protein tolerance to random amino acid change. PNAS., 2004, vol. 101 (25): 9205-9210.*
Genbank Accession Number: National Center for Biotechnology Information, National Library of Medicine, National Institutes of Health, GenBank Locus AJ245436, Accession No. AJ245436.1, "*Pseudomonas putida* OCT plasmid alk genes cluster (alkBFGHJKL, alkN and alkST genes) and flanking DNA, strain TF4-1L (GPo1), formerly annotated as *Pseudomonas oleovorans*," [online]. Bethesda, MD [retrieved on Apr. 3, 2009]. Retrieved from the Internet<URL:http://www.ncbi.nlm.nih.gov/nuccore/5824135>; first page only.
Genbank Accession Number: National Center for Biotechnology Information, National Library of Medicine, National Institutes of Health, GenBank Locus EF219372, Accession No. EF219372.1, "Marinobacter hydrocarbonoclasticus strain DSM8798 medium-chain acyl-CoA synthetase (acs1) gene, complete cds," [online]. Bethesda, MD [retrieved on Apr. 3, 2009]. Retrieved from the Internet<URL:http://www.ncbi.nlm.nih.gov/nuccore/126567221>; 3 pgs.
Genbank Accession Number: National Center for Biotechnology Information, National Library of Medicine, National Institutes of Health, GenBank Locus EF219373, Accession No. EF219373.1, "Marinobacter hydrocarbonoclasticus strain DSM8798 long-chain acyl-CoA synthetase (acs2) gene, complete cds," [online]. Bethesda, MD [retrieved on Apr. 3, 2009]. Retrieved from the Internet<URL:http://www.ncbi.nlm.nih.gov/nuccore/126567223>; 3 pgs.
Genbank Accession Number: National Center for Biotechnology Information, National Library of Medicine, National Institutes of Health, GenBank Locus EF219374, Accession No. EF219374.1, "Marinobacter hydrocarbonoclasticus strain DSM8798 long-chain acyl-CoA synthetase (acs3) gene, complete cds," [online]. Bethesda, MD [retrieved on Apr. 3, 2009]. Retrieved from the Internet<URL:http://www.ncbi.nlm.nih.gov/nuccore/126567225>; 3 pgs.

(Continued)

*Primary Examiner* — Ganapathirama Raghu
(74) *Attorney, Agent, or Firm* — Mueting Raasch & Gebhardt, P.A.

(57) ABSTRACT

The present invention provides isolated polynucleotides and isolated polypeptides. The polypeptides of the present invention have isoprenoid wax ester synthase activity or isoprenoid acyl CoA-synthetase activity. The present invention also includes methods of using the polynucleotides and polypeptides of the present invention. For instance, the methods include producing biodiesel and producing wax esters.

21 Claims, 20 Drawing Sheets

OTHER PUBLICATIONS

*Genbank Accession Number*: National Center for Biotechnology Information, National Library of Medicine, National Institutes of Health, GenBank Locus EF219375, Accession No. EF219375.1, "Marinobacter hydrocarbonoclasticus strain DSM8798 long-chain acyl-CoA synthetase (acs4) gene, complete cds," [online]. Bethesda, MD [retrieved on Apr. 3, 2009]. Retrieved from the Internet<URL:http://www.ncbi.nlm.nih.gov/nuccore/126567227>; 3 pgs.

*Genbank Accession Number*: National Center for Biotechnology Information, National Library of Medicine, National Institutes of Health, GenBank Locus EF219376, Accession No. EF219376.1, "Marinobacter hydrocarbonoclasticus strain DSM8798 wax ester synthase (ws1) gene, complete cds," [online]. Bethesda, MD [retrieved on Apr. 3, 2009]. Retrieved from the Internet<URL:http://www.ncbi.nlm.nih.gov/nuccore/126567229>; 3 pgs.

*Genbank Accession Number*: National Center for Biotechnology Information, National Library of Medicine, National Institutes of Health, GenBank Locus EF219377, Accession No. EF219377.1, "Marinobacter hydrocarbonoclasticus strain DSM8798 wax ester synthase (ws2) gene, complete cds," [online]. Bethesda, MD [retrieved on Apr. 3, 2009]. Retrieved from the Internet<URL:http://www.ncbi.nlm.nih.gov/nuccore/126567231>; 3 pgs.

*Genbank Accession Number*: National Center for Biotechnology Information, National Library of Medicine, National Institutes of Health, GenBank Locus EF219378, Accession No. EF219378.1, "Marinobacter hydrocarbonoclasticus strain DSM8798 ws3 gene, complete cds," [online]. Bethesda, MD [retrieved on Apr. 3, 2009]. Retrieved from the Internet<URL:http://www.ncbi.nlm.nih.gov/nuccore/126567233>; 3 pgs.

*Genbank Accession Number*: National Center for Biotechnology Information, National Library of Medicine, National Institutes of Health, GenBank Locus EF219379, Accession No. EF219379.1, "Marinobacter hydrocarbonoclasticus strain DSM8798 ws4 pseudogene, complete sequence," [online]. Bethesda, MD [retrieved on Apr. 3, 2009]. Retrieved from the Internet<URL:http://www.ncbi.nlm.nih.gov/nuccore/126567235>; 2 pgs.

*Genbank Accession Number*: National Center for Biotechnology Information, National Library of Medicine, National Institutes of Health, GenPept Locus ABJ10798, Accession No. ABJ10798.1, "putative AMP-binding protein [Pseudomonas aeruginosa UCBPP-PA14]," [online]. Bethesda, MD [retrieved on Apr. 3, 2009]. Retrieved from the Internet<URL:http://www.ncbi.nlm.nih.gov/nuccore/115584783>; 2 pgs.

Akoh et al., "Enzymatic approach to biodiesel production," Oct. 31, 2007, *J. Agric. Food Chem.*, 55(22):8995-9005. Available online Sep. 29, 2007.

Alvarez et al., "Lipid storage compounds in marine bacteria," *Appl. Microbiol. Biotechnol.*, 1997, 47:132-139.

Alvarez et al., "Identification of phenyldecanoic acid as a constituent of triacylglycerols and wax ester produced by Rhodococcus opacus PD630," *Microbiol.*, May 2002, 148(Pt 5):1407-1412.

Antoni et al., "Biofuels from microbes," *Appl. Microbiol. Biotechnol.*, Nov. 2007, 77(1):23-35. Available online Sep. 22, 2007.

Arora et al., "Promiscuous fatty acyl CoA ligases produce acyl-CoA and acyl-SNAC precursors for polyketide biosynthesis," *J. Am. Chem. Soc.*, Jul. 6, 2005, 127(26):9388-9389.

Bowie et al., "Deciphering the message in protein sequences: tolerance to amino acid substitutions," *Science*, Mar. 16, 1990, 247(4948):1306-1310.

Canoira et al., "Biodiesel from Jojoba oil-wax: transesterification with methanol and properties as a fuel ," *Biomass and Bioenergy*, 2006, 30:76-81. Available online Sep. 19, 2005.

Carvalhal et al., "Ethanol production from lactose and whey by *Escherichia coli* expressing genes from Zymomonas mobilis," *Revista De Microbiologia*, 1996, 27(4):263-267.

Chemler et al., "Biosynthesis of isoprenoids, polyunsaturated fatty acids and flavonoids in Saccharomyces cerevisiae," *Microb. Cell Fact.*, May 23, 2006, 5(20):9 pgs.

Chisti, "Biodiesel from microalgae beats bioethanol," *Trends Biotechnol.*, Mar. 2008, 26(3):126-31. Available online Jan. 24, 2008.

Dahlqvist et al., "Phospholipid:diacylglycerol acyltransferase: an enzyme that catalyzes the acyl-CoA-independent formation of triacylglycerol in yeast and plants," *Proc. Natl. Acad. Sci USA*, Jun. 6, 2000, 97(12):6487-6492. Available online May 30, 2000.

Daniel et al., "Induction of a novel class of diacylglycerol acyltransferases and triacylglycerol accumulation in *Mycobacterium tuberculosis* as it goes into a dormancy-like state in culture," *J Bacteriol.*, Aug. 2004, 186(15):5017-5030.

Dien et al., "Bacteria engineered for fuel ethanol production: current status," *Appl. Microbiol. Biotechnol.*, 2003, 63:258-266. Available online Sep. 16, 2003.

Dunahay et al., "Manipulation of microalgal lipid production using genetic engineering," *Appl. Biochem. Biotechnol.*, 1996, 57/58:223-231.

Ellman, "Tissue sulfhydryl groups," *Arch. Biochem. Biophys.*, 1959, 82:70-77.

Fickers et al., "Hydrophobic substrate utilisation by the yeast Yarrowia lipolytica, and its potential applications," *FEMS Yeast Res.*, Apr. 2005, 5(6-7):527-543. Available online Oct. 22, 2004.

Gaspar et al., "The emergence of yeast lipidomics," *Biochim. Biophys. Acta.*, Mar. 2007, 1771(3):241-254. Available online Jul. 14, 2006.

Gauthier et al., "Marinobacter hydrocarbonoclasticus gen. nov., sp. nov., a new, extremely halotolerant, hydrocarbon-degrading marine bacterium," *Int. J. Syst. Bacteriol.*, Oct. 1992, 42(4):568-576.

Geigenberger et al., "Tuber physiology and properties of starch from tubers of transgenic potato plants with altered plastidic adenylate transporter activity," *Plant Physiol.*, Apr. 2001, 125(4):1667-78.

Harlow et al., *Antibodies: A Laboratory Manual*, Cold Spring Harbor Laboratory Press, Cold Spring Harbor, NY, 1988; title page, publisher's page and table of contents only, 9 pages.

Hisanaga et al., "Structural basis of the substrate-specific two-step catalysis of long chain fatty acyl-CoA synthetase dimer," *J. Biol. Chem.*, Jul. 23, 2004; 279(30):31717-31726. Available online May 15, 2004.

Holtzapple et al., "Biosynthesis of isoprenoid wax ester in Marinobacter hydrocarbonoclasticus DSM 8798: identification and characterization of isoprenoid coenzyme A synthetase and wax ester synthases," *J. Bacteriol.*, May 2007, 189(10):3804-3812. Available online Mar. 9, 2007.

Holtzapple et al., "Identification of Novel Isoprenoid Wax Ester Synthases," International Symposium on Biological Polyesters, Minneapolis, MN, Aug. 28, 2006, poster; 1 pg.

Holtzapple et al., "Identification and Characterization of an acyl-CoA synthetase and Isoprenoid wax ester synthases from Marinobacter hydrocarbonoclasticus DSM 8798," Gordon Research Conference, Mount Holyoke, MA, Jul. 15-20, 2007, poster; 1 pg.

Holtzapple et al., "Microbial Metal from Renewable Resources," Initiative for Renewable Energy and the Environment (IREE) Symposium, Minneapolis, MN, Nov. 28, 2007, poster; 1 pg.

Huu et al., "Marinobacter aquaeolei sp. nov., a halophilic bacterium isolated from a Vietnamese oil-producing well," *Int. J. Syst. Bacteriol.*, Apr. 1999, 49(Pt 2):367-375.

Ingram et al., "Efficient Ethanol- Production from Xylose, Lactose and Glucose by Recombinant *Escherichia-coli*," *Abstracts of Papers of the American Chemical Society*, 1989, 198:29-MBTD.

Ishige et al., "Wax ester production by bacteria," *Curr. Opin. Microbiol.*, Jun. 2003, 6(3):244-250.

Jetter et al., "Plant surface lipid biosynthetic pathways and their utility for metabolic engineering of waxes and hydrocarbon biofuels," *Plant J.*, May 2008, 54(4):670-683.

Kalscheuer et al., "A novel bifunctional wax ester synthase/acyl-CoA:diacylglycerol acyltransferase mediates wax ester and triacylglycerol biosynthesis in Acinetobacter calcoaceticus ADP1," *J. Biol. Chem.*, Mar. 7, 2003, 278(10):8075-8082. Available online Dec. 26, 2002.

Kalscheuer et al., "Synthesis of novel lipids in *Saccharomyces cerevisiae* by heterologous expression of an unspecific bacterial acyltransferase," *Appl. Environ. Microbiol.*, Dec. 2004, 70(12):7119-7125.

Kalscheuer et al., "Neutral lipid biosynthesis in engineered *Escherichia coli*: jojoba oil-like wax esters and fatty acid butyl esters," *Appl. Environ. Microbiol.*, Feb. 2006, 72(2):1373-1379.

Kalscheuer et al., "Microdiesel: *Escherichia coli* engineered for fuel production," *Microbiol.*, Sep. 2006, 152(Pt 9):2529-2536.

Kalscheuer et al., "Analysis of storage lipid accumulation in Alcanivorax borkumensis: Evidence for alternative triacylglycerol biosynthesis routes in bacteria," *J. Bacteriol.*, Feb. 2007, 189(3):918-928. Available online Nov. 22, 2006.

Klaus et al., "Increased fatty acid production in potato by engineering of acetyl-CoA carboxylase," *Planta*, Jul. 2004, 219(3):389-96. Available online Mar. 10, 2004.

Marquez et al., "Marinobacter hydrocarbonoclasticus Gauthier et al. 1992 and Marinobacter aquaeolei Nguyen et al. 1999 are heterotypic synonyms," *Int. J. Syst. Evol. Microbiol.*, May 2005, 55(Pt 3):1349-1351.

Olivera et al., "Two different pathways are involved in the beta-oxidation of n-alkanoic and n-phenylalkanoic acids in Pseudomonas putida U: genetic studies and biotechnological applications," *Mol. Microbiol.*, Feb. 2001, 39(4):863-874.

Olukoshi et al., "Importance of stored triacylglycerols in Streptomyces: possible carbon source for antibiotics," *Microbiol.*, Apr. 1994, 140(Pt 4):931-943.

Packter et al., "Ultrastructural studies of neutral lipid localisation in Streptomyces," *Arch. Microbiol.*, Dec. 1995, 164(6):420-427.

Papiz et al., "The structure and thermal motion of the B800-850 LH2 complex from Rps.acidophila at 2.0A resolution and 100K: new structural features and functionally relevant motions," *Mol. Biol.*, Mar. 7, 2003, 326(5):1523-1538.

Rontani et al., "Aerobic and anaerobic metabolism of 6,10,14-trimethylpentadecan-2-one by a denitrifying bacterium isolated from marine sediments," *Appl. Environ. Microbiol.*, Feb. 1997, 63(2):636-643.

Rontani et al., "Production of wax esters during aerobic growth of marine bacteria on isoprenoid compounds," *Appl. Environ. Microbiol.*, Jan. 1999, 65(1):221-230.

Rontani et al., "Production of a polyunsaturated isoprenoid wax ester during aerobic metabolism of squalene by Marinobacter squalenivorans sp. nov.," *Appl. Environ. Microbiol.*, Jul. 2003, 69(7):4167-4176.

Sambrook et al., *Molecular Cloning: A Laboratory Manual, Books 1-3*, Cold Spring Harbor Laboratory Press, Cold Spring Harbor, NY, 1989; title page, publisher's page and table of contents only, 30 pgs.

Sandager et al., "Storage lipid synthesis is non-essential in yeast," *J. Biol. Chem.*, Feb. 22, 2002, 277(8):6478-6482. Available online Dec. 10, 2001.

Schmidt-Dannert et al., "Molecular breeding of carotenoid biosynthetic pathways," *Nat. Biotechnol.*, Jul. 2000, 18(7):750-753.

Stachelhaus et al., "Peptide bond formation in nonribosomal peptide biosynthesis. Catalytic role of the condensation domain," *J. Biol. Chem.*, Aug. 28, 1998, 273(35):22773-22781.

Steinberg et al., "Very long-chain acyl-CoA synthetases. Human "bubblegum" represents a new family of proteins capable of activating very long-chain fatty acids," *J. Biol. Chem.*, Nov. 10, 2000, 275(45):35162-35169.

Steinbüchel, "Perspectives for biotechnological production and utilization of biopolymers: metabolic engineering of polyhydroxyalkanoate biosynthesis pathways as a successful example," *Macromol. Biosci.*, 2001, 1:1-24.

Stolz et al., "Identification of the plasma membrane H+-biotin symporter of *Saccharomyces cerevisiae* by rescue of a fatty acid-auxotrophic mutant," *J. Biol. Chem.*, Jun. 25, 1999, 274(26):18741-18746.

Stöveken et al., "The wax ester synthase/acyl coenzyme A:diacylglycerol acyltransferase from Acinetobacter sp. strain ADP1: characterization of a novel type of acyltransferase," *J. Bacteriol.*, Feb. 2005, 187(4):1369-1376.

Stryer, *Biochemistry*, 3rd ed., W.H. Freeman And Company, New York, 1988, title page, publisher's page, pp. 481-485.

Talarico et al., "Construction and expression of an ethanol production operon in Gram-positive bacteria," *Microbiol.*, Dec. 2005, 151(Pt 12):4023-4031.

Tatusova et al., "BLAST 2 Sequences, a new tool for comparing protein and nucleotide sequences," *FEMS Microbiol. Lett.*, May 15, 1999; 174(2):247-50.

Tjaden et al., "Expression of a plastidic ATP/ADP transporter gene in *Escherichia coli* leads to a functional adenine nucleotide transport system in the bacterial cytoplasmic membrane," *J. Biol. Chem.*, 1998, 273(16):9630-9636.

Trivedi et al., "Enzymic activation and transfer of fatty acids as acyl-adenylates in mycobacteria," *Nature*, Mar. 25, 2004, 428(6981):441-445.

Uthoff et al., "Thio wax ester biosynthesis utilizing the unspecific bifunctional wax ester synthase/acyl coenzyme A:diacylglycerol acyltransferase of Acinetobacter sp. strain ADP1," *Appl. Environ. Microbiol.*, Feb. 2005, 71(2):790-796.

van Beilen et al., "DNA sequence determination and functional characterization of the OCT-plasmid-encoded alkJKL genes of *Pseudomonas oleovorans*," *Mol. Microbiol.*, Nov. 1992, 6(21):3121-3136.

Verschuren et al., "Evaluation of jojoba oil as a low-energy fat. 2. Intestinal transit time, stomach emptying and digestibility in short-term feeding studies in rats," *Food Chem. Toxicol.*, Jan. 1989, 27(1):45-8.

Wältermann et al., "Rhodococcus opacus strain PD630 as a new source of high-value single-cell oil? Isolation and characterization of triacylglycerols and other storage lipids," *Microbiol.*, May 2000, 146(Pt 5):1143-1149.

Wältermann et al., "Mechanism of lipid-body formation in prokaryotes: how bacteria fatten up," *Mol. Microbiol.*, Feb. 2005, 55(3):750-763.

Wältermann et al., "Neutral lipid bodies in prokaryotes: recent insights into structure, formation, and relationship to eukaryotic lipid depots," *J. Bacteriol.*, Jun. 2005, 187(11):3607-3619.

Wältermann et al., "Key enzymes for biosynthesis of neutral lipid storage compounds in prokaryotes: properties, function and occurrence of wax ester synthases/acyl-CoA: diacylglycerol acyltransferases," *Biochimie*, Feb. 2007, 89(2):230-242. Available online Aug. 7, 2006

Watkins et al., "Phytanic acid activation in rat liver peroxisomes is catalyzed by long-chain acyl-CoA synthetase," *J. Lipid Res.*, Nov. 1996, 37(11):2288-2295.

Wiegel, "Formation of ethanol by bacteria. A pledge for the use of extreme thermophilic anaerobic bacteria in industrial ethanol fermentation processes," *Experientia*, 1980, 36:1434-1446.

Wisniak, "Jojoba oil and derivatives," *Prog. Chem. Fats Other Lipids*, 1977, 15(3):167-218.

Yanisch-Perron et al. "Improved M13 phage cloning vectors and host strains: nucleotide sequences of the M13mp18 and pUC19 vectors," *Gene*, 1985, 33(1):103-119.

* cited by examiner

```
ADP1    1   ----MRPLHPIDFIPLSLEKRQQPMHVGGLFLFQIPDNAPDTFIQDLVNDIRISKSIPVP
WS1     1   ----MTPLNPTDQLFLWLEKRQQPMHVGGLQLFSPPEGAPDDYVAQLADQLRQKTEVTAP
WS2     1   ----MKRLGTLDASWLAVESEDTPMHVGTLQIFSLPEGAPETFLRDMVTRMKEAGDVAPP
WS3     1   ----MRQLSELDASFLYLESDTTPMHIGGIYLFDASGLSNPLAFSTFVAYLRSRLHVVPL
WS4     1   MSAKRTAMTSVDRSWLRMDTPENPMMISAVLAFE-----QPIPLKRLKRTLEERFLKFRR

ADP1    57  ---PFNN-----KLNGLFWDEDEEFDLDHHFRHIALPHPGRIRELLIYISQEHSTLLDRA
WS1     57  FNQRLSY-----RLGQPVWVEDEHLDLEHHFRFEALPTPGRIRELLSFVSAEHSHLMDRE
WS2     57  WGYKLAWSGFLGRVIAPAWKVDKDIDLDYHVRHSALPRPGGERELGILVSRLHSNPLDFS
WS3     57  FRQKLKEIPL--RLGRPYWVDDADFSIERHLAYVNLGEHGKQASLISLASKILEEPLKRD
WS4     56  FRQRIVD-----KGDKVYWEDDPLFDLDNHLHTIALPGNAGKRELQALASDFNSTALDFR

ADP1    109 KPLWTCNILEGI--------EGNRFAMYFKIHHAMVDGVAGMRLIEKSLSHDVTEKSIVPP
WS1     112 RPMWEVHLIEGL--------KDRQFALYTKVHHSLVDGVSAMRMATRMLSENPDEHGMPPI
WS2     117 RPLWECHVIEGL--------ENNRFALYTKMHHSMIDGISGVRLMQRVLTTDPERCNMPPP
WS3     115 RPLWHITFVDGFRIDDPEGEKEGFALIVKLHHAAIDAFSGEEIMGKLEYTPSPRTITPP
WS4     111 RPLWQIHYIDNY--------ENGCALLIRIHHCIADGISLVRVLLSLTDRTPEPKLERVA

ADP1    162 W---CVEGKRAKRLRE------PKTGKIKKIMSGIKSQLQATPTVIQELSQTVFKDIGRN
WS1     165 WDLPCLSRDRGESDGH------SLWRSVTHLLGLSDRQLGTIPTVAKELLKTI-NQARKD
WS2     170 WTVRPHQRRGAKTDKEA-----SVPAAVSQAMDALKLQADMAPRLWQAGNRLVHSVRHPE
WS3     175 ---RPWLPRQEPSEERV-----FLQAGANMLKTPMQLASLAYNAAEATTRGLIQKQLHKL
WS4     163 HPKLPTKPNGTAASRFLHRIVDSTQAAWGQANLFVDSIRKEPDYPLKLATTAGGIVLDLA

ADP1    213 PDHVSSFQAPCSILNQRVSSSRRFAAQSFDLDRFRNIAKSL-NVTINDVVLAVCSGALRA
WS1     218 PAYDSIFHAPRCMLNQKITGSRRFAAQSWCLKRIRAVCEAY-GTTVNDVVTAMCAAALRT
WS2     225 DGLTAPFTGPVSVLNHRVTAQRRFATQHYQLDRLKNLAHAS-GGSLNDIVLYLCGTALRR
WS3     227 PLPLPLFTAPHSPFNRQITANRRIVSTSVDLSRLKAIKGSLVDVTLNDVVLGLCAESLAR
WS4     223 KLGLAPFEPKTSLKSPLLGRKQVAWAEPLELETVKQCARTL-GGTVNDVLLCAATGALTR

ADP1    272 YLMSH-NSLPSKPLIAMVPASIR-ND-D-SDVSNRITMILANLATHKDDPLQRLEIIRRS
WS1     277 YLMNQ-DALPEKPLVAFVPVSLR-RD-D-SSGGNQVGVILASLHTDVQDAGERLLKIHHG
WS2     284 FLAEQ-NNLPDTPLTAGIPVNIRPAD-D-EGTGTQISFMIASLATDEADPLNRLQQIKTS
WS3     287 YLANQ-NIETKSSLVAMTPISVRSSSLR-KATGNQMSAMLLDLATAEPNPAARIRRIHRN
WS4     282 HFTEHGQSIPDCGIRVAVPFNLRPLDQPIETLGNQFGLVLVCLPVEVTDPIMCFRQVQEN

ADP1    328 VQNSKQRFKRMTSDQILNYSAVVYGPAGLNIISGM--MPKRQ-AFNLVISNVPGPREPLY
WS1     333 MEEAKQRYRHMSPEEIVNYTALTLAPAAFHLLTGL--APKWQ-TFNVVISNVPGPSRPLY
WS2     341 TRRAKEHLQKLPKSALTQYTMLLMSPYILQLMSGL--GGRMRPVFNVTISNVPGPEGTLY
WS3     345 AVESEPYREAIAADRLTELLPSTLLALSARLYSELQVAQRYQPLFNVPITNVPGPQVPLY
WS4     342 MNRLKRSYXAQVTYSLLDLFGRGPDILERRALDLL------SNKASAVLTNVPGPRHAVY
                                   *

ADP1    385 WNGAKLDALYPASIVLDGQALNITMTSYLDKLEVGLIACRNALPRMQNLLTHLEEEIQLF
WS1     390 WNGAKLEGMYPVSIDMDRLALNMTLTSYNDQVEFGLIGCRRTLPSLQRMLDYLEQGLAEL
WS2     399 YEGARLEAMYPVSLIAHGGALNITCLSVAGSLNFGFTGCRDTLPSMQKLAVYTGEALDEL
WS3     405 LQGARLVRQYNSAPLFDSLGLVIVAVSYQGQLTLNFTLCPDVVADSDQLPELVHDSLEAI
WS4     396 LAGSKLVQPMFWVPQSGNIGIGMSIFSYAGTVQFGITVDKGIKADPGEVMDYFRDSFENL

ADP1    445 EGVIAKQEDIKTAN-------------------------------
WS1     450 ELNAGL----------------------------------------
WS2     459 ESLILPPKKRARTRK-------------------------------
WS3     465 EKAAAELGPDQGHEQFPEPQHNMTDDVLAYVEKLLKGGLGKFRR
WS4     456 HQAALEKAGAGGFRQAS-----------------------------
```

*Fig. 2*

Gene Cluster 1
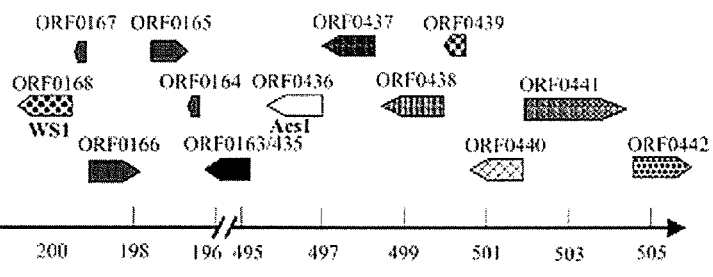
Gene Cluster 2
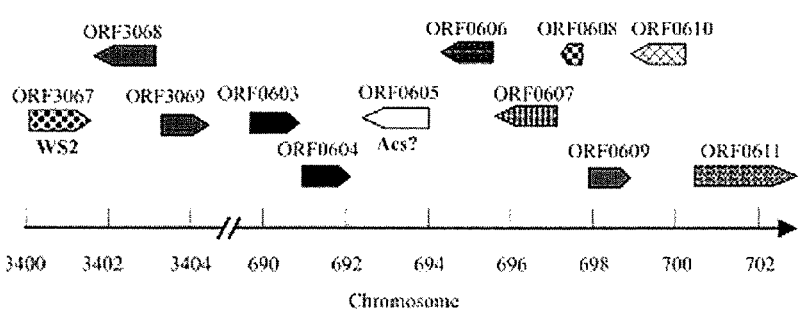
Key:
- ⬜ Acyl-CoA synthetase
- ⬛ Alcohol dehydrogenase
- ▥ Aldehyde dehydrogenase
- ▧ Alkane 1-monooxygenase
- ▨ AlkB1GHJ regulator
- ▩ Rubredoxin
- ▦ Rubredoxin reductase
- ▤ Wax ester synthase
- ⬛ Transposase
⟷ = 2 kilobases (2,000 bp)
Fig. 3

O  T  WS1 WS2 WS3

← ethyloleate

← fatty acids

Std.    ----    WS2

*Fig. 11*

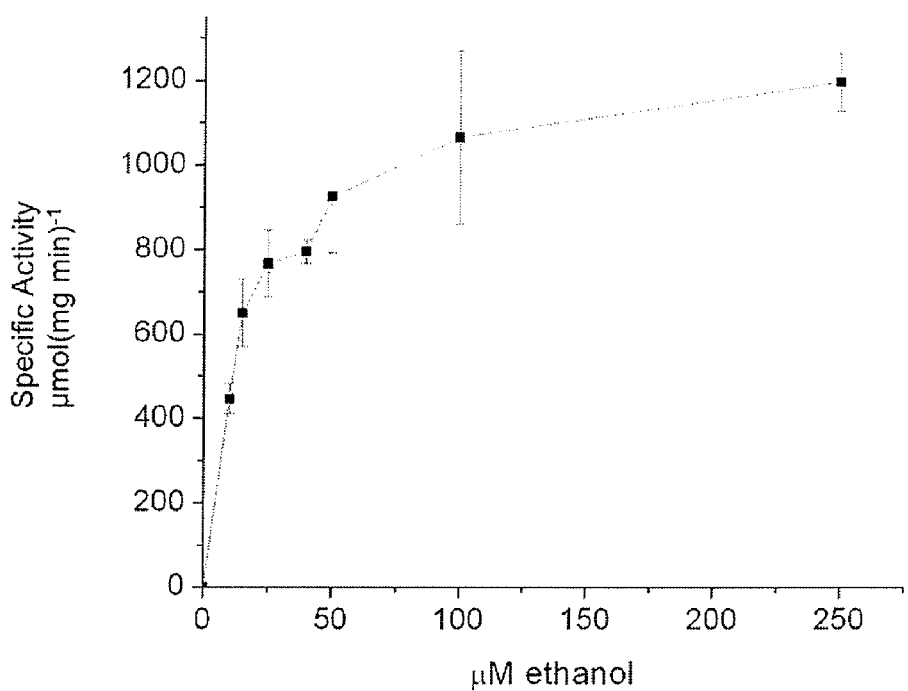
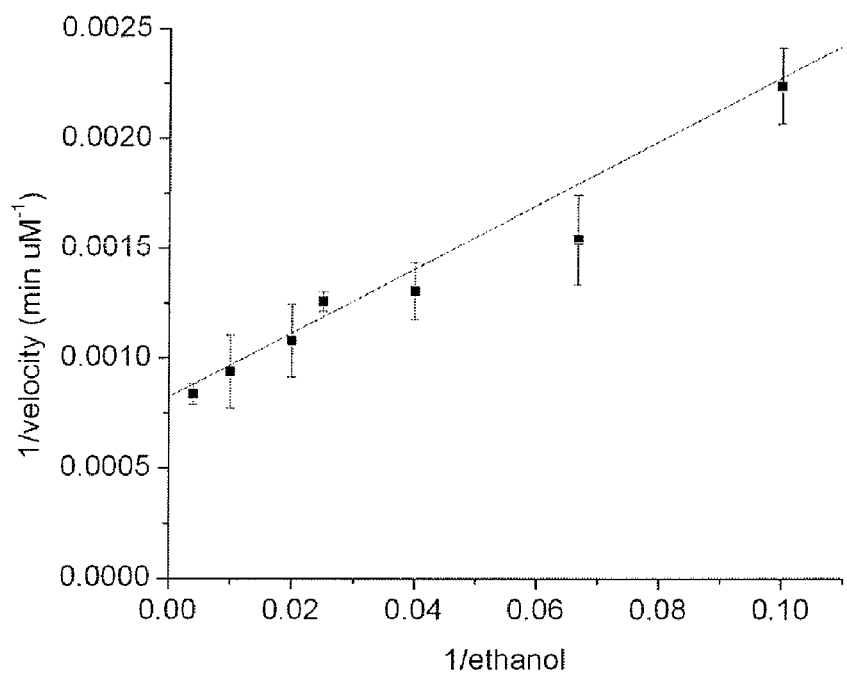
*Fig. 14*

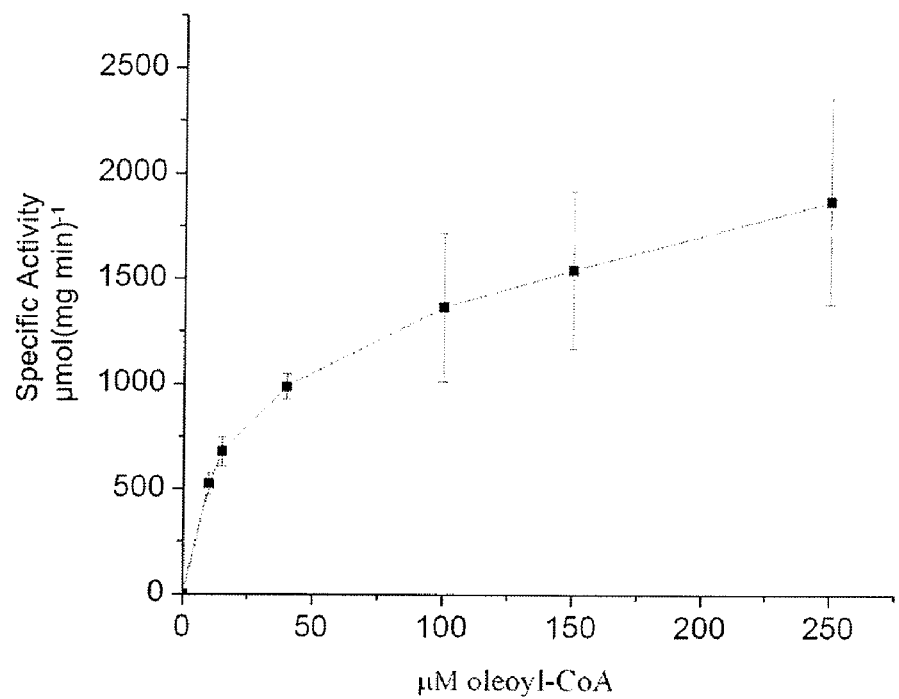
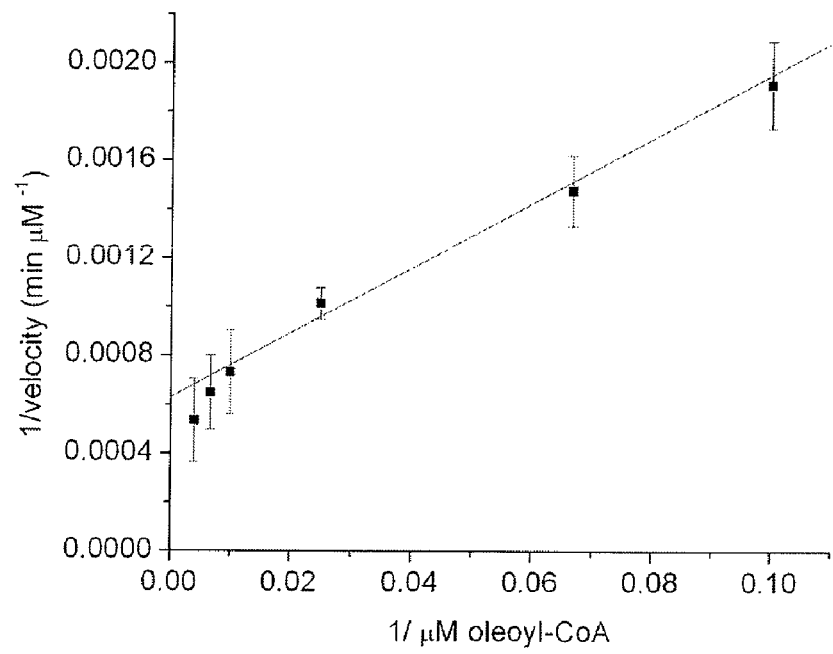
Fig. 15

Fig. 19

A  TGATTTTCCCGAGCGATCGGTCTTGGCAAAACATTACAATCAGGGGGCTTCTGAACCCATCCGGTAGTACCCCACAGCGC
CAATCAGACAGGAGATGGTGATGGATTTTGAGCAGTTCTATCAAGACAAATACCCAGCTGGCATCCCCCGGGAAATCGAT
CTCAATAAATACAAGAACATGGTGGATGTTTTTGAGCAGGCGGTACAGAAGTTTGCAGACAAGCCTGCGTTTACAGCAGT
TGGCGTTACCCTGACTTATCGGGATCTTGATACTCAGAGCCGCAACTTCGCGGCCTGGCTGCAGAACAAAACCGACCTGA
AACCGGGCGACCGCATTGCGGTGCAGATGCCGAACGTTACCCAGTATCCGGTGGTTGTGTTCGGAGCCATGCGCGCTGGT
CTGATTGTGGTGAACACCAACCCCCTGTACACCACTCGCGAGATGGAGCACCAGTTTAACGATTCTGGCGCAAAGGCTCT
GGTTGTTCTGGCCAATATGGCCGACAACGCGGAGAAGGTGTTGCCTCATACCGGCATCGAGCACGTGATCGTGACCGAGA
TTGCCGATATGCATTCCCCCATCAAGCGTACCCTGATGAATGCCGCGGTGAAGCACCTCAAGAAGATGGTTCCGGCGTTC
AACATTCCGGGTGCTCATAAGCTGCCGGCGGTACTCAGTGCCGGTGCCCGTGAAAAGTTTACCCCGGTCGACATCAAGCT
GGATGACCTGGCCGTGCTGCAGTACACCGGTGGTACCACTGGTGTTGCCAAGGGTGCCATGCTGACTCACGCCAACCTGG
TGGCCAACCTGACACAAGTCCGGCCAATGCTGGAAGATCAGGTGGAAGAGGGCAAGGAAGTGGTGATTGCACCGCTGCCG
CTGTACCACATTTACTCCTTCACCCTGAACTGCGGCATTATGCTGGAAGCAGGTGCCCATAACGTTCTGATTCCGAACCC
GCGTGATATCCCCGGCTTTGTTAAAGAGCTGCAGAAGCAGAAGTTCTCTGCCTTTATTGGCCTGAATACCTTGTTTGTGG
CCCTGTGCAACAACGAGGACTTCCAGGATCTGGACTTCTCTGGCCTCAAGCTGACTGCCTCTGGTGGTATGGCTCTGACC
AGTGATACCGCGAAAATGTGGCAGCGTGTGACCGGTTGCGAAATCAGCGAAGGCTACGGTATGACCGAGACTTCTCCGGT
GGTTACCTTCAATCCCCGCAGCGCCATCCAGATCGGCACCATCGGTCTGCCGATTCCGTCCACTGTGGTCAAAACCATTG
ACGACGACGGCAACGAAACGCCGGTCGGCGAGCCGGGCGAACTGTGCGTGAAAGGCCCGCAGGTGATGCGCGGTTACTGG
CAGCGTCCCGATGATACCCAGAAGTCGTTCACCGATGACGGTTTCCTGAAGACCGGCGATGTGGCCCTGATCCAGGAAGA
TGGCTATATCCGCATTGTGGATCGTAAAAAGGACATGATCATTTGTGTCCGGTTTTAACGTGTTCCCGAACGAAATCGAAG
ATGTTGTGACCACACACCCGAAAGTGGTGGAGTGTGCCGCCGTGGGGATCCCCGATGCCAAGAGCGGCGAAGCGGTGAAG
GTTTATGTAGTGCCCACCAAAGAAGGTGTAACCGCCAACGAACTCAAGGAGTTCTGTCGGGAGCGTCTGACCGCCTACAA
GGTACCCAAGCACTTTGAGTTCCGTGATGAACTGCCAAAGAGCAACGTGGGCAAGATCCTGCGCCGTGAGCTGCGGGACG
AGGCGAACGCCAAGTAACAGGCGAGGCCCGCAGACCAACCAAAGACCCTGCTTCGGCGGGGTCTTTGTGTTTCTTGGCTC
CGGTTTTCGTTAGACTGTTTTGCCCTGACGTTCCACC

B  GATGGGAGCCCAATCCCGGTTTTGATCGTGTGCACCTGCGGATATCAGTATACTTGCAGGAAACAACCAAAACACAAATG
ACTGCGGAGAATGACAAGGAATGAAACGTCTCGGAACCCTGGACGCCTCCTGGCTGGCGGTTGAATCTGAAGACACCCC
GATGCATGTGGGTACGCTTCAGATTTTCTCACTGCCGGAAGGCGCACCAGAAACCTTCCTGCGTGACATGGTCACTCGAA
TGAAAGAGGCCGGCGATGTGGCACCACCCTGGGGATACAAACTGGCCTGGTCTGGTTTCCTCGGGCGCGTGATCGCCCCG
GCCTGGAAAGTCGATAAGGATATCGATCTGGATTATCACGTCCGGCACTCAGCCCTGCCTCGCCCCGGCGGGGAGCGCGA
ACTGGGTATTCTGGTATCCCGACTGCACTCTAACCCCCTGGATTTTTCCCGCCCTCTTTGGGAATGCCACGTTATTGAAG
GCCTGGAGAATAACCGTTTTGCCCTTTACACCAAAATGCACCACTCGATGATTGACGGCATCAGCGGCGTGCGACTGATG
CAGAGGGTGCTCACCACCGATCCCGAACGCTGCAATATGCCACCGCCCTGGACGGTACGCCCACACCAACGCCGTGGTGC
AAAAACCGACAAAGAGGCCAGCGTGCCCGCAGCGGTTTCCCAGGCCATGGACGCCCTGAAGCTCCAGGCAGACATGGCCC
CCAGGCTGTGGCAGGCCGGCAATCGCCTGGTGCATTCGGTTCGACACCCGGAAGACGGACTGACCGCGCCCTTCACTGGA
CCGGTTTCGGTGCTCAATCACCGGGTTACCGCGCAGCGACGTTTTGCCACCCAGCATTATCAACTGGACCGGCTGAAAAA
CCTGGCCCATGCTTCCGGCGGTTCCTTGAACGACATCGTGCTTTACCTGTGTGGCACCGCATTGCGGCGCTTTCTGGCTG
AGCAGAACAATCTGCCAGACACCCCGCTGACGGCTGGTATACCGGTGAATATCCGGCCGGCAGACGACGAGGGTACGGGC
ACCCAGATCAGTTTCATGATTGCCTCGCTGGCCACCGACGAAGCTGATCCGTTGAACCGCCTGCAACAGATCAAAACCTC
GACCCCGACGGGCCAAGGAGCACCTGCAGAAACTTCCAAAAAGTGCCCTGACCCAGTACACCATGCTGCTGATGTCACCCT
ACATTCTGCAATTGATGTCAGGTCTCGGGGGGAGGATGCGACCAGTCTTCAACGTGACCATTTCCAACGTGCCCGGCCCG
GAAGGCACGCTGTATTATGAAGGAGCCCGGCTTGAGGCCATGTATCCGGTATCGCTAATCGCTCACGGCGGCGCCCTGAA
CATCACCTGCCTGAGCTATCCGGATCGCTGAATTTCGGTTTTACCGGCTGTCGGGATACGCTGCCGAGCATGCAGAAAC
TGGCCGGTTTATACCGGTGAAGCTCTGGATGAGCTGGAATCGCTGATTCTGCCACCCAAGAAGCGCGCCCGAACCCGCAAG
TAACCCAGGACGGGGTCAGTCGCTTTGCCAGTGACCAGCCCCGACAAAAATCATCTGCAGGAATCGGGTGGTGCGTTTTC
GCACCTGGCCGATCTGATAATCG

SEQUENCE LISTING

<160> NUMBER OF SEQ ID NOS: 21

<210> SEQ ID NO 1
<211> LENGTH: 1422
<212> TYPE: DNA
<213> ORGANISM: Marinobacter hydrocarbonoclasticus

<400> SEQUENCE: 1

```
atgaaacgtc tcggaaccct ggacgcctcc tggctggcgg ttgaatctga agacacccg      60
atgcatgtgg gtacgcttca gatttctca ctgccggaag gcgcaccaga aaccttcctg     120
cgtgacatgg tcactcgaat gaaagaggcc ggcgatgtgg caccaccctg gggatacaaa    180
ctggcctggt ctggtttcct cgggcgcgtg atcgcccgc cctggaaagt cgataaggat     240
atcgatctgg attatcacgt ccggcactca gccctgcctc gccccggcgg ggagcgcgaa    300
ctgggtattc tggtatcccg actgcactct aaccccctgg attttcccg ccctctttgg     360
gaatgccacg ttattgaagg cctggagaat aaccgttttg ccctttacac caaaatgcac    420
cactcgatga ttgacggcat cagcggcgtg cgactgatgc agagggtgct caccaccgat    480
cccgaacgct gcaatatgcc accgccctgg acggtacgcc cacaccaacg ccgtggtgca    540
aaaaccgaca aagaggccag cgtgcccgca gcggtttccc aggccatgga cgccctgaag    600
ctccaggcag acatggcccc caggctgtgg caggccggca atcgcctggt gcattcggtt    660
cgacacccgg aagacggact gaccgcgccc ttcactggac cggtttcggt gctcaatcac    720
cgggttaccg cgcagcgacg ttttgccacc cagcattatc aactggaccg gctgaaaaac    780
ctggcccatg cttccggcgg ttccttgaac gacatcgtgc tttacctgtg tggcaccgca    840
ttgcggcgct ttctggctga gcagaacaat ctgccagaca ccccgctgac ggctggtata    900
ccggtgaata tccggccggc agacgacgag ggtacgggca cccagatcag tttcatgatt    960
gcctcgctgg ccaccgacga agctgatccg ttgaaccgcc tgcaacagat caaaacctcg   1020
acccgacggg ccaaggagca cctgcagaaa cttccaaaaa gtgccctgac ccagtacacc   1080
atgctgctga tgtcaccta cattctgcaa ttgatgtcag gtctcggggg gaggatgcga   1140
ccagtcttca acgtgaccat ttccaacgtg cccggcccgg aaggcacgct gtattatgaa   1200
ggagcccggc ttgaggccat gtatccggta tcgctaatcg ctcacggcgg cgccctgaac   1260
atcacctgcc tgagctatgc cggatcgctg aatttcggtt ttaccggctg tcgggatacg   1320
ctgccgagca tgcagaaact ggcggtttat accggtgaag ctctggatga gctggaatcg   1380
ctgattctgc cacccaagaa gcgcgcccga acccgcaagt aa                     1422
```

<210> SEQ ID NO 2
<211> LENGTH: 473
<212> TYPE: PRT
<213> ORGANISM: Marinobacter hydrocarbonoclasticus

<400> SEQUENCE: 2

-continued

```
Met Lys Arg Leu Gly Thr Leu Asp Ala Ser Trp Leu Ala Val Glu Ser
1               5                   10                  15

Glu Asp Thr Pro Met His Val Gly Thr Leu Gln Ile Phe Ser Leu Pro
                20                  25                  30

Glu Gly Ala Pro Glu Thr Phe Leu Arg Asp Met Val Thr Arg Met Lys
            35                  40                  45

Glu Ala Gly Asp Val Ala Pro Pro Trp Gly Tyr Lys Leu Ala Trp Ser
        50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Trp Thr Val Arg Pro His Gln
                165                 170                 175

Arg Arg Gly Ala Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Ser Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Val Ser Leu Ile Ala His Gly
                405                 410                 415
```

```
Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
            435                 440                 445

Val Tyr Thr Gly Glu Ala Leu Asp Glu Leu Glu Ser Leu Ile Leu Pro
        450                 455                 460

Pro Lys Lys Arg Ala Arg Thr Arg Lys
465                 470
```

```
<210> SEQ ID NO 3
<211> LENGTH: 1677
<212> TYPE: DNA
<213> ORGANISM: Marinobacter hydrocarbonoclasticus

<400> SEQUENCE: 3
```

| | |
|---|---:|
| atggattttg agcagttcta tcaagacaaa tacccagctg catcccccg ggaaatcgat | 60 |
| ctcaataaat acaagaacat ggtggatgtt tttgagcagg cggtacagaa gtttgcagac | 120 |
| aagcctgcgt ttacagcagt tggcgttacc ctgacttatc gggatcttga tactcagagc | 180 |
| cgcaacttcg cggcctggct gcagaacaaa accgacctga accgggcga ccgcattgcg | 240 |
| gtgcagatgc cgaacgttac ccagtatccg gtggttgtgt cggagccat gcgcgctggt | 300 |
| ctgattgtgg tgaacaccaa ccccctgtac accactcgcg agatggagca ccagtttaac | 360 |
| gattctggcg caaaggctct ggttgttctg ccaatatgg ccgacaacgc ggagaaggtg | 420 |
| ttgcctcata ccggcatcga gcacgtgatc gtgaccgaga ttgccgatat gcattccccc | 480 |
| atcaagcgta ccctgatgaa tgccgcggtg aagcacctca gaagatggt tccggcgttc | 540 |
| aacattccgg gtgctcataa gctgccggcg gtactcagtg ccggtgcccg tgaaaagttt | 600 |
| accccggtcg acatcaagct ggatgacctg gccgtgctgc agtacaccgg tggtaccact | 660 |
| ggtgttgcca agggtgccat gctgactcac gccaacctgg tggccaacct gacacaagtc | 720 |
| cggccaatgc tggaagatca ggtggaagag ggcaaggaag tggtgattgc accgctgccg | 780 |
| ctgtaccaca tttactcctt caccctgaac tgcggcatta tgctggaagc aggtgcccat | 840 |
| aacgttctga ttccgaaccc gcgtgatatc cccggctttg ttaaagagct gcagaagcag | 900 |
| aagttctctg cctttattgg cctgaatacc ttgtttgtgg ccctgtgcaa caacgaggac | 960 |
| ttccaggatc tggacttctc tggcctcaag ctgactgcct ctggtggtat ggctctgacc | 1020 |
| agtgataccg cgaaaatgtg gcagcgtgtg accggttgcg aaatcagcga aggctacggt | 1080 |
| atgaccgaga cttctccggt ggttaccttc aatccccgca cgccatcca gatcggcacc | 1140 |
| atcggtctgc cgattccgtc cactgtggtc aaaaccattg acgacgacgg caacgaaacg | 1200 |
| ccggtcggcg agccgggcga actgtgcgtg aaaggcccgc aggtgatgcg cggttactgg | 1260 |
| cagcgtcccg atgataccca gaagtcgttc accgatgacg gtttcctgaa gaccggcgat | 1320 |
| gtggccctga tccaggaaga tggctatatc cgcattgtga tcgtaaaaa ggacatgatc | 1380 |
| attgtgtccg gttttaacgt gttcccgaac gaaatcgaag atgttgtgac cacacacccg | 1440 |
| aaagtggtgg agtgtgccgc cgtggggatc cccgatgcca gagcggcga agcggtgaag | 1500 |
| gtttatgtag tgcccaccaa agaaggtgta accgccaacg aactcaagga gttctgtcgg | 1560 |
| gagcgtctga ccgcctacaa ggtacccaag cactttgagt ccgtgatga actgccaaag | 1620 |
| agcaacgtgg gcaagatcct cgccgtgag ctgcgggacg aggcgaacgc caagtaa | 1677 |

```
<210> SEQ ID NO 4
<211> LENGTH: 558
```

```
<212> TYPE: PRT
<213> ORGANISM: Marinobacter hydrocarbonoclasticus

<400> SEQUENCE: 4

Met Asp Phe Glu Gln Phe Tyr Gln Asp Lys Tyr Pro Ala Gly Ile Pro
1               5                   10                  15

Arg Glu Ile Asp Leu Asn Lys Tyr Lys Asn Met Val Asp Val Phe Glu
            20                  25                  30

Gln Ala Val Gln Lys Phe Ala Asp Lys Pro Ala Phe Thr Ala Val Gly
        35                  40                  45

Val Thr Leu Thr Tyr Arg Asp Leu Asp Thr Gln Ser Arg Asn Phe Ala
    50                  55                  60

Ala Trp Leu Gln Asn Lys Thr Asp Leu Lys Pro Gly Asp Arg Ile Ala
65                  70                  75                  80

Val Gln Met Pro Asn Val Thr Gln Tyr Pro Val Val Phe Gly Ala
                85                  90                  95

Met Arg Ala Gly Leu Ile Val Val Asn Thr Asn Pro Leu Tyr Thr Thr
                100                 105                 110

Arg Glu Met Glu His Gln Phe Asn Asp Ser Gly Ala Lys Ala Leu Val
            115                 120                 125

Val Leu Ala Asn Met Ala Asp Asn Ala Glu Lys Val Leu Pro His Thr
        130                 135                 140

Gly Ile Glu His Val Ile Val Thr Glu Ile Ala Asp Met His Ser Pro
145                 150                 155                 160

Ile Lys Arg Thr Leu Met Asn Ala Ala Val Lys His Leu Lys Lys Met
                165                 170                 175

Val Pro Ala Phe Asn Ile Pro Gly Ala His Lys Leu Pro Ala Val Leu
            180                 185                 190

Ser Ala Gly Ala Arg Glu Lys Phe Thr Pro Val Asp Ile Lys Leu Asp
        195                 200                 205

Asp Leu Ala Val Leu Gln Tyr Thr Gly Gly Thr Thr Gly Val Ala Lys
    210                 215                 220

Gly Ala Met Leu Thr His Ala Asn Leu Val Ala Asn Leu Thr Gln Val
225                 230                 235                 240

Arg Pro Met Leu Glu Asp Gln Val Glu Glu Gly Lys Glu Val Val Ile
                245                 250                 255

Ala Pro Leu Pro Leu Tyr His Ile Tyr Ser Phe Thr Leu Asn Cys Gly
            260                 265                 270

Ile Met Leu Glu Ala Gly Ala His Asn Val Leu Ile Pro Asn Pro Arg
        275                 280                 285

Asp Ile Pro Gly Phe Val Lys Glu Leu Gln Lys Gln Lys Phe Ser Ala
    290                 295                 300

Phe Ile Gly Leu Asn Thr Leu Phe Val Ala Leu Cys Asn Asn Glu Asp
305                 310                 315                 320

Phe Gln Asp Leu Asp Phe Ser Gly Leu Lys Leu Thr Ala Ser Gly Gly
                325                 330                 335

Met Ala Leu Thr Ser Asp Thr Ala Lys Met Trp Gln Arg Val Thr Gly
            340                 345                 350

Cys Glu Ile Ser Glu Gly Tyr Gly Met Thr Glu Thr Ser Pro Val Val
        355                 360                 365

Thr Phe Asn Pro Arg Ser Ala Ile Gln Ile Gly Thr Ile Gly Leu Pro
    370                 375                 380

Ile Pro Ser Thr Val Val Lys Thr Ile Asp Asp Asp Gly Asn Glu Thr
385                 390                 395                 400
```

```
Pro Val Gly Glu Pro Gly Glu Leu Cys Val Lys Gly Pro Gln Val Met
            405                 410                 415
Arg Gly Tyr Trp Gln Arg Pro Asp Asp Thr Gln Lys Ser Phe Thr Asp
        420                 425                 430
Asp Gly Phe Leu Lys Thr Gly Asp Val Ala Leu Ile Gln Glu Asp Gly
            435                 440                 445
Tyr Ile Arg Ile Val Asp Arg Lys Lys Asp Met Ile Ile Val Ser Gly
    450                 455                 460
Phe Asn Val Phe Pro Asn Glu Ile Glu Asp Val Val Thr Thr His Pro
465                 470                 475                 480
Lys Val Val Glu Cys Ala Ala Val Gly Ile Pro Asp Ala Lys Ser Gly
                485                 490                 495
Glu Ala Val Lys Val Tyr Val Val Pro Thr Lys Glu Gly Val Thr Ala
            500                 505                 510
Asn Glu Leu Lys Glu Phe Cys Arg Glu Arg Leu Thr Ala Tyr Lys Val
        515                 520                 525
Pro Lys His Phe Glu Phe Arg Asp Glu Leu Pro Lys Ser Asn Val Gly
    530                 535                 540
Lys Ile Leu Arg Arg Glu Leu Arg Asp Glu Ala Asn Ala Lys
545                 550                 555
```

<210> SEQ ID NO 5
<211> LENGTH: 1623
<212> TYPE: DNA
<213> ORGANISM: Marinobacter hydrocarbonoclasticus

<400> SEQUENCE: 5

```
gatgggagcc caatcccggt tttgatcgtg tgcacctgcg gatatcagta tacttgcagg      60
aaacaaccaa aacacaaatg actggcgcag aatgacaagg aatgaaacgt ctcggaaccc     120
tggacgcctc ctggctggcg gttgaatctg aagacacccc gatgcatgtg ggtacgcttc     180
agattttctc actgccggaa ggcgcaccag aaaccttcct gcgtgacatg gtcactcgaa     240
tgaaagaggc cggcgatgtg gcaccaccct ggggatacaa actggcctgg tctggtttcc     300
tcgggcgcgt gatcgccccg gcctggaaag tcgataagga tatcgatctg gattatcacg     360
tccggcactc agccctgcct cgccccggcg gggagcgcga actgggtatt ctggtatccc     420
gactgcactc taacccccctg gattttttccc gccctctttg ggaatgccac gttattgaag     480
gcctggagaa taaccgtttt gcccctttaca ccaaaatgca ccactcgatg attgacggca     540
tcagcggcgt gcgactgatg cagagggtgc tcaccaccga tcccgaacgc tgcaatatgc     600
caccgccctg gacggtacgc ccacaccaac gccgtggtgc aaaaaccgac aaagaggcca     660
gcgtgcccgc agcggttcc caggccatgg acgccctgaa gctccaggca gacatggccc     720
ccaggctgtg gcaggccggc aatcgcctgg tgcattcggt tcgacacccg gaagacggac     780
tgaccgcgcc cttcactgga ccggtttcgg tgctcaatca ccgggttacc gcgcagcgac     840
gttttgccac ccagcattat caactggacc ggctgaaaaa cctggcccat gcttccggcg     900
gttccttgaa cgacatcgtg ctttacctgt gtggcaccgc attgcggcgc tttctggctg     960
agcagaacaa tctgccagac accccgctga cggctggtat accggtgaat atccggccgg    1020
cagacgacga gggtacgggc acccagatca gtttcatgat tgcctcgctg gccaccgacg    1080
aagctgatcc gttgaaccgc ctgcaacaga tcaaaaccct cgacccgacg gccaaggagc    1140
acctgcagaa acttccaaaa agtgccctga cccagtacac catgctgctg atgtcaccct    1200
```

-continued

```
acattctgca attgatgtca ggtctcgggg ggaggatgcg accagtcttc aacgtgacca    1260
tttccaacgt gcccggcccg gaaggcacgc tgtattatga aggagcccgg cttgaggcca    1320
tgtatccggt atcgctaatc gctcacggcg gcgccctgaa catcacctgc ctgagctatg    1380
ccggatcgct gaatttcggt tttaccggct gtcgggatac gctgccgagc atgcagaaac    1440
tggcggttta taccggtgaa gctctggatg agctggaatc gctgattctg ccacccaaga    1500
agcgcgcccg aacccgcaag taacccagga cggggtcagt cgctttgcca gtgaccagcc    1560
ccgacaaaaa tcatctgcag gaatcgggtg gtgcgttttc gcacctggcc gatctgataa    1620
tcg                                                                  1623

<210> SEQ ID NO 6
<211> LENGTH: 1878
<212> TYPE: DNA
<213> ORGANISM: Marinobacter hydrocarbonoclasticus

<400> SEQUENCE: 6
tgattttccc gagccgatcg gtcttggcaa acattacaa tcaggggggct tctgaaccca       60 tccggtagta ccccacagcg ccaatcagac aggagatggt gatggatttt gagcagttct      120
atcaagacaa atacccagct ggcatccccc gggaaatcga tctcaataaa tacaagaaca      180
tggtggatgt ttttgagcag gcggtacaga agtttgcaga caagcctgcg tttacagcag      240
ttggcgttac cctgacttat cgggatcttg atactcagag ccgcaacttc gcggcctggc      300
tgcagaacaa aaccgacctg aaaccggggcg accgcattgc ggtgcagatg ccgaacgtta      360
cccagtatcc ggtggttgtg ttcggagcca tgcgcgctgg tctgattgtg gtgaacacca      420
accccctgta caccactcgc gagatggagc accagtttaa cgattctggc gcaaaggctc      480
tggttgttct ggccaatatg gccgacaacg cggagaaggt gttgcctcat accggcatcg      540
agcacgtgat cgtgaccgag attgccgata tgcattcccc catcaagcgt accctgatga      600
atgccgcggt gaagcacctc aagaagatgg ttccggcgtt caacattccg ggtgctcata      660
agctgccggc ggtactcagt gccggtgccc gtgaaaagtt taccccggtc gacatcaagc      720
tggatgacct ggccgtgctg cagtacaccg gtggtaccac tggtgttgcc aagggtgcca      780
tgctgactca cgccaacctg gtggccaacc tgacacaagt ccggccaatg ctggaagatc      840
aggtggaaga gggcaaggaa gtggtgattg caccgctgcc gctgtaccac atttactcct      900
tcacccctga actgcggcatt atgctggaag caggtgccca taacgttctg attccgaacc      960
cgcgtgatat ccccggcttt gttaaagagc tgcagaagca gaagttctct gcctttattg     1020
gcctgaatac cttgtttgtg gccctgtgca caacgagga cttccaggat ctggacttct     1080
ctggcctcaa gctgactgcc tctggtggta tggctctgac cagtgatacc gcgaaaatgt     1140
ggcagcgtgt gaccggttgc gaaatcagcg aaggctacgg tatgaccgag acttctccgg     1200
tggttacctt caatccccgc agcgccatcc agatcggcac catcggtctg ccgattccgt     1260
ccactgtggt caaaaccatt gacgacgacg gcaacgaaac gccggtcggc gagccgggcg     1320
aactgtgcgt gaaaggcccg caggtgatgc gcggttactg gcagcgtccc gatgataccc     1380
agaagtcgtt caccgatgac ggtttcctga gaccggcga tgtggccctg atccaggaag     1440
atggctatat ccgcattgtg gatcgtaaaa aggacatgat cattgtgtcc ggttttaacg     1500
tgttcccgaa cgaaatcgaa gatgttgtga ccacacaccc gaaagtggtg gagtgtgccg     1560
ccgtggggat ccccgatgcc aagagcggcg aagcggtgaa ggtttatgta gtgcccacca     1620
aagaaggtgt aaccgccaac gaactcaagg agttctgtcg ggagcgtctg accgcctaca     1680
```

-continued

```
aggtacccaa gcactttgag ttccgtgatg aactgccaaa gagcaacgtg ggcaagatcc    1740
tgcgccgtga gctgcgggac gaggcgaacg ccaagtaaca ggcgaggccc gcagaccaac    1800
caaagaccct gcttcggcgg ggtctttgtg tttcttggct ccggttttcg ttagactgtt    1860
ttgccctgac gttccacc                                                 1878
```

```
<210> SEQ ID NO 7
<211> LENGTH: 458
<212> TYPE: PRT
<213> ORGANISM: Acinobacter baylyi

<400> SEQUENCE: 7

Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Gln Ile Pro
                20                  25                  30

Asp Asn Ala Pro Asp Thr Phe Ile Gln Asp Leu Val Asn Asp Ile Arg
            35                  40                  45

Ile Ser Lys Ser Ile Pro Val Pro Pro Phe Asn Asn Lys Leu Asn Gly
        50                  55                  60

Leu Phe Trp Asp Glu Asp Glu Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Arg Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
        275                 280                 285

Pro Ala Ser Ile Arg Asn Asp Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335
```

```
Arg Met Thr Ser Asp Gln Ile Leu Asn Tyr Ser Ala Val Val Tyr Gly
            340                 345                 350

Pro Ala Gly Leu Asn Ile Ile Ser Gly Met Met Pro Lys Arg Gln Ala
            355                 360                 365

Phe Asn Leu Val Ile Ser Asn Val Pro Gly Pro Arg Glu Pro Leu Tyr
            370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Ile Gln Leu Phe Glu Gly Val Ile
            435                 440                 445

Ala Lys Gln Glu Asp Ile Lys Thr Ala Asn
    450                 455
```

<210> SEQ ID NO 8
<211> LENGTH: 455
<212> TYPE: PRT
<213> ORGANISM: Marinobacter hydrocarbonoclasticus

<400> SEQUENCE: 8

```
Met Thr Pro Leu Asn Pro Thr Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Pro Asp Asp Tyr Val Ala Gln Leu Ala Asp Gln Leu Arg
        35                  40                  45

Gln Lys Thr Glu Val Thr Ala Pro Phe Asn Gln Arg Leu Ser Tyr Arg
    50                  55                  60

Leu Gly Gln Pro Val Trp Val Glu Asp Glu His Leu Asp Leu Glu His
65                  70                  75                  80

His Phe Arg Phe Glu Ala Leu Pro Thr Pro Gly Arg Ile Arg Glu Leu
                85                  90                  95

Leu Ser Phe Val Ser Ala Glu His Ser His Leu Met Asp Arg Glu Arg
            100                 105                 110

Pro Met Trp Glu Val His Leu Ile Glu Gly Leu Lys Asp Arg Gln Phe
        115                 120                 125

Ala Leu Tyr Thr Lys Val His His Ser Leu Val Asp Gly Val Ser Ala
    130                 135                 140

Met Arg Met Ala Thr Arg Met Leu Ser Glu Asn Pro Asp Glu His Gly
145                 150                 155                 160

Met Pro Pro Ile Trp Asp Leu Pro Cys Leu Ser Arg Asp Arg Gly Glu
                165                 170                 175

Ser Asp Gly His Ser Leu Trp Arg Ser Val Thr His Leu Leu Gly Leu
            180                 185                 190

Ser Asp Arg Gln Leu Gly Thr Ile Pro Thr Val Ala Lys Glu Leu Leu
        195                 200                 205

Lys Thr Ile Asn Gln Ala Arg Lys Asp Pro Ala Tyr Asp Ser Ile Phe
    210                 215                 220

His Ala Pro Arg Cys Met Leu Asn Gln Lys Ile Thr Gly Ser Arg Arg
225                 230                 235                 240

Phe Ala Ala Gln Ser Trp Cys Leu Lys Arg Ile Arg Ala Val Cys Glu
```

Ala Tyr Gly Thr Thr Val Asn Asp Val Val Thr Ala Met Cys Ala Ala
            245                 250                 255

Ala Leu Arg Thr Tyr Leu Met Asn Gln Asp Ala Leu Pro Glu Lys Pro
        260                 265                 270

Leu Val Ala Phe Val Pro Val Ser Leu Arg Arg Asp Asp Ser Ser Gly
    275                 280                 285

Gly Asn Gln Val Gly Val Ile Leu Ala Ser Leu His Thr Asp Val Gln
290                 295                 300

Asp Ala Gly Glu Arg Leu Leu Lys Ile His His Gly Met Glu Glu Ala
305                 310                 315                 320

Lys Gln Arg Tyr Arg His Met Ser Pro Glu Glu Ile Val Asn Tyr Thr
            325                 330                 335

Ala Leu Thr Leu Ala Pro Ala Ala Phe His Leu Leu Thr Gly Leu Ala
        340                 345                 350

Pro Lys Trp Gln Thr Phe Asn Val Val Ile Ser Asn Val Pro Gly Pro
    355                 360                 365

Ser Arg Pro Leu Tyr Trp Asn Gly Ala Lys Leu Glu Gly Met Tyr Pro
370                 375                 380

Val Ser Ile Asp Met Asp Arg Leu Ala Leu Asn Met Thr Leu Thr Ser
385                 390                 395                 400

Tyr Asn Asp Gln Val Glu Phe Gly Leu Ile Gly Cys Arg Arg Thr Leu
            405                 410                 415

Pro Ser Leu Gln Arg Met Leu Asp Tyr Leu Gln Gly Leu Ala Glu
        420                 425                 430

Leu Glu Leu Asn Ala Gly Leu
    435                 440                 445

450                 455

<210> SEQ ID NO 9
<211> LENGTH: 508
<212> TYPE: PRT
<213> ORGANISM: Marinobacter hydrocarbonoclasticus

<400> SEQUENCE: 9

Met Arg Gln Leu Ser Glu Leu Asp Ala Ser Phe Leu Tyr Leu Glu Ser
1               5                   10                  15

Asp Thr Thr Pro Met His Ile Gly Gly Ile Tyr Leu Phe Asp Ala Ser
            20                  25                  30

Gly Leu Ser Asn Pro Leu Ala Phe Ser Thr Phe Val Ala Tyr Leu Arg
        35                  40                  45

Ser Arg Leu His Val Val Pro Leu Phe Arg Gln Lys Leu Lys Glu Ile
    50                  55                  60

Pro Leu Arg Leu Gly Arg Pro Tyr Trp Val Asp Asp Ala Asp Phe Ser
65                  70                  75                  80

Ile Glu Arg His Leu Ala Tyr Val Asn Leu Gly Glu His Gly Lys Gln
                85                  90                  95

Ala Ser Leu Ile Ser Leu Ala Ser Lys Ile Leu Glu Glu Pro Leu Lys
            100                 105                 110

Arg Asp Arg Pro Leu Trp His Ile Thr Phe Val Asp Gly Phe Arg Ile
        115                 120                 125

Asp Asp Pro Glu Gly Glu Lys Glu Gly Phe Ala Ile Val Lys Leu
    130                 135                 140

His His Ala Ala Ile Asp Ala Phe Ser Gly Glu Glu Ile Met Gly Lys
145                 150                 155                 160

```
Leu Leu Glu Tyr Thr Pro Ser Pro Arg Thr Ile Thr Pro Arg Pro
            165                 170                 175

Trp Leu Pro Arg Gln Glu Pro Ser Glu Arg Val Phe Leu Gln Ala
            180                 185                 190

Gly Ala Asn Met Leu Lys Thr Pro Met Gln Leu Ala Ser Leu Ala Tyr
            195                 200                 205

Asn Ala Ala Glu Ala Thr Thr Arg Gly Leu Ile Gln Lys Gln Leu His
            210                 215                 220

Lys Leu Pro Leu Pro Leu Pro Leu Phe Thr Ala Pro His Ser Pro Phe
225                 230                 235                 240

Asn Arg Gln Ile Thr Ala Asn Arg Arg Ile Val Ser Thr Ser Val Asp
            245                 250                 255

Leu Ser Arg Leu Lys Ala Ile Lys Gly Ser Leu Val Asp Val Thr Leu
            260                 265                 270

Asn Asp Val Val Leu Gly Leu Cys Ala Glu Ser Leu Ala Arg Tyr Leu
            275                 280                 285

Ala Asn Gln Asn Ile Glu Thr Lys Ser Ser Leu Val Ala Met Thr Pro
            290                 295                 300

Ile Ser Val Arg Ser Ser Ser Leu Arg Lys Ala Thr Gly Asn Gln Met
305                 310                 315                 320

Ser Ala Met Leu Leu Asp Leu Ala Thr Ala Glu Pro Asn Pro Ala Ala
            325                 330                 335

Arg Ile Arg Arg Ile His Arg Asn Ala Val Glu Ser Glu Pro Tyr Arg
            340                 345                 350

Glu Ala Ile Ala Ala Asp Arg Leu Thr Glu Leu Leu Pro Ser Thr Leu
            355                 360                 365

Leu Ala Leu Ser Ala Arg Leu Tyr Ser Glu Leu Gln Val Ala Gln Arg
            370                 375                 380

Tyr Gln Pro Leu Phe Asn Val Pro Ile Thr Asn Val Pro Gly Pro Gln
385                 390                 395                 400

Val Pro Leu Tyr Leu Gln Gly Ala Arg Leu Val Arg Gln Tyr Asn Ser
            405                 410                 415

Ala Pro Leu Phe Asp Ser Leu Gly Leu Val Ile Val Ala Val Ser Tyr
            420                 425                 430

Gln Gly Gln Leu Thr Leu Asn Phe Thr Leu Cys Pro Asp Val Val Ala
            435                 440                 445

Asp Ser Asp Gln Leu Pro Glu Leu Val His Asp Ser Leu Glu Ala Ile
450                 455                 460

Glu Lys Ala Ala Ala Glu Leu Gly Pro Asp Gln Gly His Glu Gln Phe
465                 470                 475                 480

Pro Glu Pro Gln His Asn Met Thr Asp Asp Val Leu Ala Tyr Val Glu
            485                 490                 495

Lys Leu Leu Lys Gly Gly Leu Gly Lys Phe Arg Arg
            500                 505

<210> SEQ ID NO 10
<211> LENGTH: 472
<212> TYPE: PRT
<213> ORGANISM: Marinobacter hydrocarbonoclasticus
<220> FEATURE:
<221> NAME/KEY: SITE
<222> LOCATION: (350)..(350)
<223> OTHER INFORMATION: X is a stop codon

<400> SEQUENCE: 10

Met Ser Ala Lys Arg Thr Ala Met Thr Ser Val Asp Arg Ser Trp Leu
```

```
1               5                   10                  15
Arg Met Asp Thr Pro Glu Asn Pro Met Met Ile Ser Ala Val Leu Ala
                20                  25                  30
Phe Glu Gln Pro Ile Pro Leu Lys Arg Leu Lys Arg Thr Leu Glu Glu
                35                  40                  45
Arg Phe Leu Lys Phe Arg Arg Phe Arg Gln Arg Ile Val Asp Lys Gly
       50                  55                  60
Asp Lys Val Tyr Trp Glu Asp Pro Leu Phe Asp Leu Asp Asn His
65                  70                  75                  80
Leu His Thr Ile Ala Leu Pro Gly Asn Ala Gly Lys Arg Glu Leu Gln
                85                  90                  95
Ala Leu Ala Ser Asp Phe Asn Ser Thr Ala Leu Asp Phe Arg Arg Pro
               100                 105                 110
Leu Trp Gln Ile His Tyr Ile Asp Asn Tyr Glu Asn Gly Cys Ala Leu
               115                 120                 125
Leu Ile Arg Ile His His Cys Ile Ala Asp Gly Ile Ser Leu Val Arg
       130                 135                 140
Val Leu Leu Ser Leu Thr Asp Arg Thr Pro Glu Pro Lys Leu Glu Arg
145                 150                 155                 160
Val Ala His Pro Lys Leu Pro Thr Lys Pro Asn Gly Thr Ala Ala Ser
               165                 170                 175
Arg Phe Leu His Arg Ile Val Asp Ser Thr Gln Ala Ala Trp Gly Gln
               180                 185                 190
Ala Asn Leu Phe Val Asp Ser Ile Arg Lys Glu Pro Tyr Pro Leu
       195                 200                 205
Lys Leu Ala Thr Thr Ala Gly Gly Ile Val Leu Asp Leu Ala Lys Leu
       210                 215                 220
Gly Leu Ala Pro Phe Glu Pro Lys Thr Ser Leu Lys Ser Pro Leu Leu
225                 230                 235                 240
Gly Arg Lys Gln Val Ala Trp Ala Glu Pro Leu Glu Leu Glu Thr Val
               245                 250                 255
Lys Gln Cys Ala Arg Thr Leu Gly Gly Thr Val Asn Asp Val Leu Leu
       260                 265                 270
Cys Ala Ala Thr Gly Ala Leu Thr Arg His Phe Thr Glu His Gly Gln
       275                 280                 285
Ser Ile Pro Asp Cys Gly Ile Arg Val Ala Val Pro Phe Asn Leu Arg
       290                 295                 300
Pro Leu Asp Gln Pro Ile Glu Thr Leu Gly Asn Gln Phe Gly Leu Val
305                 310                 315                 320
Leu Val Cys Leu Pro Val Glu Val Thr Asp Pro Ile Met Cys Phe Arg
               325                 330                 335
Gln Val Gln Glu Asn Met Asn Arg Leu Lys Arg Ser Tyr Xaa Ala Gln
               340                 345                 350
Val Thr Tyr Ser Leu Leu Asp Leu Phe Gly Arg Gly Pro Asp Ile Leu
       355                 360                 365
Glu Arg Arg Ala Leu Asp Leu Leu Ser Asn Lys Ala Ser Ala Val Leu
       370                 375                 380
Thr Asn Val Pro Gly Pro Arg His Ala Val Tyr Leu Ala Gly Ser Lys
385                 390                 395                 400
Leu Val Gln Pro Met Phe Trp Val Pro Gln Ser Gly Asn Ile Gly Ile
               405                 410                 415
Gly Met Ser Ile Phe Ser Tyr Ala Gly Thr Val Gln Phe Gly Ile Thr
               420                 425                 430
```

Val Asp Lys Gly Ile Lys Ala Asp Pro Gly Glu Val Met Asp Tyr Phe
            435                 440                 445

Arg Asp Ser Phe Glu Asn Leu His Gln Ala Ala Leu Glu Lys Ala Gly
        450                 455                 460

Ala Gly Gly Phe Arg Gln Ala Ser
465                 470

<210> SEQ ID NO 11
<211> LENGTH: 565
<212> TYPE: PRT
<213> ORGANISM: Pseudomonas putida

<400> SEQUENCE: 11

Met Ile Glu Asn Phe Trp Lys Asp Lys Tyr Pro Ala Gly Ile Thr Ala
1               5                   10                  15

Glu Ile Asn Pro Asp Glu Phe Pro Asn Ile Gln Ala Val Leu Lys Gln
            20                  25                  30

Ser Cys Gln Arg Phe Ala Asp Lys Pro Ala Phe Ser Asn Leu Gly Lys
        35                  40                  45

Thr Ile Thr Tyr Gly Glu Leu Tyr Ala Leu Ser Gly Ala Phe Ala Ala
    50                  55                  60

Trp Leu Gln Gln His Thr Asp Leu Lys Pro Gly Asp Arg Ile Ala Val
65                  70                  75                  80

Gln Leu Pro Asn Val Met Gln Tyr Pro Val Ala Val Phe Gly Ala Met
                85                  90                  95

Arg Ala Gly Leu Ile Val Val Asn Thr Asn Pro Leu Tyr Thr Ala Arg
            100                 105                 110

Glu Met Glu His Gln Phe Asn Asp Ser Gly Ala Lys Ala Leu Val Cys
        115                 120                 125

Leu Ala Asn Met Ala His Leu Ala Glu Lys Val Val Pro Lys Thr Gln
    130                 135                 140

Val Arg His Val Ile Val Thr Glu Val Ala Asp Leu Leu Pro Pro Leu
145                 150                 155                 160

Lys Arg Leu Leu Ile Asn Ser Val Ile Lys Tyr Val Lys Lys Met Val
                165                 170                 175

Pro Ala Tyr Ser Leu Pro Gln Ala Val Arg Phe Asn Asp Ala Leu Ala
            180                 185                 190

Leu Gly Lys Gly Gln Pro Val Thr Glu Ala Asn Pro Gln Ala Asn Asp
        195                 200                 205

Val Ala Val Leu Gln Tyr Thr Gly Gly Thr Thr Gly Val Ala Lys Gly
    210                 215                 220

Ala Met Leu Thr His Arg Asn Leu Val Ala Asn Met Leu Gln Cys Arg
225                 230                 235                 240

Ala Leu Met Gly Ser Asn Leu His Glu Gly Cys Glu Ile Leu Ile Thr
                245                 250                 255

Pro Leu Pro Leu Tyr His Ile Tyr Ala Phe Thr Phe His Cys Met Ala
            260                 265                 270

Met Met Leu Ile Gly Asn His Asn Val Leu Ile Ser Asn Pro Arg Asp
        275                 280                 285

Leu Pro Ala Met Val Lys Glu Leu Gly Lys Trp Lys Phe Ser Gly Phe
    290                 295                 300

Val Gly Leu Asn Thr Leu Phe Val Ala Leu Cys Asn Asn Glu Ala Phe
305                 310                 315                 320

Arg Ala Leu Asp Phe Ser Ser Leu Lys Ile Thr Leu Ser Gly Gly Met

```
                    325                 330                 335
Ala Leu Gln Leu Ser Val Ala Glu Arg Trp Lys Ala Val Thr Gly Cys
                340                 345                 350

Ala Ile Cys Glu Gly Tyr Gly Met Thr Glu Thr Ser Pro Val Ala Ala
            355                 360                 365

Val Asn Pro Ala Glu Ala Asn Gln Val Gly Thr Ile Gly Ile Pro Val
370                 375                 380

Pro Ser Thr Leu Cys Lys Ile Ile Asp Asp Ala Gly Asn Glu Leu Pro
385                 390                 395                 400

Leu Gly Glu Val Gly Glu Leu Cys Val Lys Gly Pro Gln Val Met Lys
                405                 410                 415

Gly Tyr Trp Gln Arg Glu Asp Ala Thr Ala Glu Ile Leu Asp Ser Glu
            420                 425                 430

Gly Trp Leu Lys Thr Gly Asp Ile Ala Leu Ile Gln Ala Asp Gly Tyr
        435                 440                 445

Met Arg Ile Val Asp Arg Lys Lys Asp Met Ile Leu Val Ser Gly Phe
    450                 455                 460

Asn Val Tyr Pro Asn Glu Leu Glu Asp Val Leu Ala Ala Leu Pro Gly
465                 470                 475                 480

Val Leu Gln Cys Ala Ala Ile Gly Val Pro Asp Glu Lys Ser Gly Glu
                485                 490                 495

Val Ile Lys Val Phe Ile Val Lys Pro Gly Met Thr Val Thr Lys
            500                 505                 510

Glu Gln Val Met Glu His Met Arg Ala Asn Val Thr Gly Tyr Lys Val
        515                 520                 525

Pro Arg Leu Ile Glu Phe Arg Asp Ser Leu Pro Thr Thr Asn Val Gly
    530                 535                 540

Lys Ile Leu Arg Arg Glu Leu Arg Asp Glu Glu Leu Lys Lys Gln Gly
545                 550                 555                 560

Leu Lys Lys Ile Ala
                565

<210> SEQ ID NO 12
<211> LENGTH: 546
<212> TYPE: PRT
<213> ORGANISM: Pseudomonas putida

<400> SEQUENCE: 12

Met Leu Gly Gln Met Met Arg Asn Gln Leu Val Ile Gly Ser Leu Val
1               5                   10                  15

Glu His Ala Ala Arg Tyr His Gly Ala Arg Glu Val Val Ser Val Glu
                20                  25                  30

Thr Ser Gly Glu Val Thr Arg Ser Cys Trp Lys Glu Val Glu Leu Arg
            35                  40                  45

Ala Arg Lys Leu Ala Ser Ala Leu Gly Lys Met Gly Leu Thr Pro Ser
        50                  55                  60

Asp Arg Cys Ala Thr Ile Ala Trp Asn Asn Ile Arg His Leu Glu Val
65                  70                  75                  80

Tyr Tyr Ala Val Ser Gly Ala Gly Met Val Cys His Thr Ile Asn Pro
                85                  90                  95

Arg Leu Phe Ile Glu Gln Ile Thr Tyr Val Ile Asn His Ala Glu Asp
            100                 105                 110

Lys Val Val Leu Leu Asp Asp Thr Phe Leu Pro Ile Ile Ala Glu Ile
        115                 120                 125
```

```
His Gly Ser Leu Pro Lys Val Lys Ala Phe Val Leu Met Ala His Asn
    130                 135                 140

Asn Ser Asn Ala Ser Ala Gln Met Pro Gly Leu Ile Ala Tyr Glu Asp
145                 150                 155                 160

Leu Ile Gly Gln Gly Asp Asp Asn Tyr Ile Trp Pro Asp Val Asp Glu
                165                 170                 175

Asn Glu Ala Ser Ser Leu Cys Tyr Thr Ser Gly Thr Thr Gly Asn Pro
                180                 185                 190

Lys Gly Val Leu Tyr Ser His Arg Ser Thr Val Leu His Ser Met Thr
            195                 200                 205

Thr Ala Met Pro Asp Thr Leu Asn Leu Ser Ala Arg Asp Thr Ile Leu
210                 215                 220

Pro Val Val Pro Met Phe His Val Asn Ala Trp Gly Thr Pro Tyr Ser
225                 230                 235                 240

Ala Ala Met Val Gly Ala Lys Leu Val Leu Pro Gly Pro Ala Leu Asp
                245                 250                 255

Gly Ala Ser Leu Ser Lys Leu Ile Ala Ser Glu Gly Val Ser Ile Ala
                260                 265                 270

Leu Gly Val Pro Val Val Trp Gln Gly Leu Leu Ala Ala Gln Ala Gly
            275                 280                 285

Asn Gly Ser Lys Ser Gln Ser Leu Thr Arg Val Val Val Gly Gly Ser
    290                 295                 300

Ala Cys Pro Ala Ser Met Ile Arg Glu Phe Asn Asp Ile Tyr Gly Val
305                 310                 315                 320

Glu Val Ile His Ala Trp Gly Met Thr Glu Leu Ser Pro Phe Gly Thr
                325                 330                 335

Ala Asn Thr Pro Leu Ala His His Val Asp Leu Ser Pro Asp Glu Lys
                340                 345                 350

Leu Ser Leu Arg Lys Ser Gln Gly Arg Pro Pro Tyr Gly Val Glu Leu
            355                 360                 365

Lys Ile Val Asn Asp Glu Gly Ile Arg Leu Pro Glu Asp Gly Arg Ser
370                 375                 380

Lys Gly Asn Leu Met Ala Arg Gly His Trp Val Ile Lys Asp Tyr Phe
385                 390                 395                 400

His Ser Asp Pro Gly Ser Thr Leu Ser Asp Gly Trp Phe Ser Thr Gly
                405                 410                 415

Asp Val Ala Thr Ile Asp Ser Asp Gly Phe Met Thr Ile Cys Asp Arg
                420                 425                 430

Ala Lys Asp Ile Ile Lys Ser Gly Gly Glu Trp Ile Ser Thr Val Glu
            435                 440                 445

Leu Glu Ser Ile Ala Ile Ala His Pro His Ile Val Asp Ala Ala Val
    450                 455                 460

Ile Ala Ala Arg His Glu Lys Trp Asp Glu Arg Pro Leu Leu Ile Ala
465                 470                 475                 480

Val Lys Ser Pro Asn Ser Glu Leu Thr Ser Gly Glu Val Cys Asn Tyr
                485                 490                 495

Phe Ala Asp Lys Val Ala Arg Trp Gln Ile Pro Asp Ala Ala Ile Phe
                500                 505                 510

Val Glu Glu Leu Pro Arg Asn Gly Thr Gly Lys Ile Leu Lys Asn Arg
            515                 520                 525

Leu Arg Glu Lys Tyr Gly Asp Ile Leu Leu Arg Ser Ser Ser Ser Val
530                 535                 540

Cys Glu
```

545

<210> SEQ ID NO 13
<211> LENGTH: 555
<212> TYPE: PRT
<213> ORGANISM: Pseudomonas aeruginosa

<400> SEQUENCE: 13

Met Val Thr Ala Asn Arg Leu Pro Leu Glu Val Phe Phe Glu Arg Glu
1               5                   10                  15

Lys Arg His Pro Gln Arg Arg Tyr Leu Val Gln Pro Ile Gly Gly Gly
            20                  25                  30

Arg Val Glu Glu Leu Ser Trp Gly Glu Val Gly Asp Gln Ala Arg Arg
        35                  40                  45

Ala Ala Ala Trp Leu Arg Ser Leu Asp Leu Pro Ala Gly Ser Arg Ile
    50                  55                  60

Ala Ile Ile Ser Lys Asn Cys Ala His Trp Ile Val Thr Asp Leu Ala
65                  70                  75                  80

Ile Trp Met Ala Gly His Val Ser Val Pro Leu Tyr Pro Asn Leu Thr
                85                  90                  95

Ala Glu Ser Ala Arg Gln Val Leu Glu His Ser Glu Ser Ala Val Val
            100                 105                 110

Phe Val Gly Lys Leu Asp Asp Trp Pro Ala Met Ala Pro Gly Val Pro
        115                 120                 125

Glu Gly Ile Pro Thr Val Ala Met Pro Leu His Pro Glu Gly Arg Phe
    130                 135                 140

Asp Arg Gln Trp Ser Asp Leu Gln Ala Cys Ala Pro Leu Glu Gly Asp
145                 150                 155                 160

Thr Pro Thr Ala Ala Glu Gln Leu Ala Thr Leu Ile Tyr Thr Ser Gly
                165                 170                 175

Thr Thr Gly Val Pro Lys Gly Val Met His Asn Phe Ser Ser Phe Ala
            180                 185                 190

Phe Ala Ala Ser Arg Gly Val Glu Leu Phe Gly Thr Arg Glu Asp Asp
        195                 200                 205

Arg Met Leu Ser Tyr Leu Pro Leu Cys His Val Ala Glu Arg Met Phe
210                 215                 220

Val Glu Met Gly Ser Leu Tyr Gly Gly Thr Thr Val Phe Phe Ala Glu
225                 230                 235                 240

Ser Leu Asp Thr Phe Leu Glu Asp Met Lys Arg Ala Arg Pro Thr Leu
                245                 250                 255

Leu Phe Gly Val Pro Arg Ile Trp Thr Lys Phe Gln Met Gly Val Tyr
            260                 265                 270

Ser Lys Met Pro Ala Gln Lys Leu Asp Arg Leu Leu Lys Leu Pro Ile
        275                 280                 285

Leu Gly Arg Ile Val Gly Arg Lys Val Leu Ala Gly Leu Gly Leu Asp
    290                 295                 300

Ala Val Arg Tyr Ala Leu Cys Gly Ala Ala Pro Val Pro Glu Ala Leu
305                 310                 315                 320

Leu Leu Trp Tyr Arg Arg Leu Gly Leu Asp Val Leu Glu Val Tyr Gly
                325                 330                 335

Met Thr Glu Asn Ser Gly Tyr Ser His Val Cys Arg Pro Gly Arg Gln
            340                 345                 350

Lys Thr Gly Trp Ile Gly Gln Asn Ser Pro Gly Val Glu Val Arg Ile
        355                 360                 365

```
Ser Asp Glu Gly Glu Val Gln Val Arg Ser Gly Ala Thr Met Val Gly
    370                 375                 380

Tyr Tyr Lys Glu Pro Glu Lys Thr Ala Glu Val Leu Thr Ser Asp Gly
385                 390                 395                 400

Phe Leu Arg Thr Gly Asp Lys Gly Glu Gln Asp Ala Asp Gly Asn Leu
                405                 410                 415

Arg Leu Thr Gly Arg Met Lys Glu Ile Phe Lys Thr Ser Lys Gly Lys
            420                 425                 430

Tyr Val Ala Pro Ala Pro Ile Glu Asn Arg Leu Ala Val His Asp Arg
        435                 440                 445

Ile Glu Gln Val Cys Val Val Gly Gly Leu Ser Ala Pro Leu Gly
    450                 455                 460

Leu Cys Val Leu Ser Glu Val Gly Arg Arg Glu Ala Leu Asn Gly Thr
465                 470                 475                 480

Arg Gly Ala Leu Glu Ser Ser Leu Arg Ala His Leu Glu Gln Val Asn
                485                 490                 495

Gly Ala Leu Asp Lys His Glu Arg Leu Val Gly Leu Val Leu Val Gln
            500                 505                 510

Glu Thr Trp Ala Val Asp Asn Gly Phe Leu Thr Pro Thr Leu Lys Ile
        515                 520                 525

Lys Arg Asn Met Val Glu Gly Ala Tyr Gly Ser Arg Phe His Glu Trp
530                 535                 540

Val Glu Arg Arg Glu Ala Val Leu Trp His Glu
545                 550                 555
```

```
<210> SEQ ID NO 14
<211> LENGTH: 238
<212> TYPE: PRT
<213> ORGANISM: artificial
<220> FEATURE:
<223> OTHER INFORMATION: Consensus sequence
<220> FEATURE:
<221> NAME/KEY: MISC_FEATURE
<222> LOCATION: (14)..(14)
<223> OTHER INFORMATION: X is Asn, Asp, Gln, or Glu
<220> FEATURE:
<221> NAME/KEY: MISC_FEATURE
<222> LOCATION: (37)..(37)
<223> OTHER INFORMATION: X is Ile or Val
<220> FEATURE:
<221> NAME/KEY: MISC_FEATURE
<222> LOCATION: (46)..(46)
<223> OTHER INFORMATION: X is Asn, Asp, Gln, or Glu
<220> FEATURE:
<221> NAME/KEY: MISC_FEATURE
<222> LOCATION: (55)..(55)
<223> OTHER INFORMATION: X is Ile or Val
<220> FEATURE:
<221> NAME/KEY: MISC_FEATURE
<222> LOCATION: (67)..(67)
<223> OTHER INFORMATION: X is Asn, Asp, Gln, or Glu
<220> FEATURE:
<221> NAME/KEY: MISC_FEATURE
<222> LOCATION: (71)..(72)
<223> OTHER INFORMATION: X is Asn, Asp, Gln, or Glu
<220> FEATURE:
<221> NAME/KEY: MISC_FEATURE
<222> LOCATION: (88)..(88)
<223> OTHER INFORMATION: X is Leu or Met
<220> FEATURE:
<221> NAME/KEY: MISC_FEATURE
<222> LOCATION: (93)..(93)
<223> OTHER INFORMATION: X is Leu or Met
<220> FEATURE:
<221> NAME/KEY: MISC_FEATURE
<222> LOCATION: (96)..(96)
<223> OTHER INFORMATION: X is Asn, Asp, Gln, or Glu
```

```
<220> FEATURE:
<221> NAME/KEY: MISC_FEATURE
<222> LOCATION: (100)..(100)
<223> OTHER INFORMATION: X is Leu or Met
<220> FEATURE:
<221> NAME/KEY: MISC_FEATURE
<222> LOCATION: (102)..(102)
<223> OTHER INFORMATION: X is Ile or Val
<220> FEATURE:
<221> NAME/KEY: MISC_FEATURE
<222> LOCATION: (105)..(105)
<223> OTHER INFORMATION: X is Leu or Met
<220> FEATURE:
<221> NAME/KEY: MISC_FEATURE
<222> LOCATION: (133)..(133)
<223> OTHER INFORMATION: X is Leu or Met
<220> FEATURE:
<221> NAME/KEY: MISC_FEATURE
<222> LOCATION: (149)..(149)
<223> OTHER INFORMATION: X is Ile or Val
<220> FEATURE:
<221> NAME/KEY: MISC_FEATURE
<222> LOCATION: (150)..(150)
<223> OTHER INFORMATION: X is Asn, Asp, Gln, or Glu
<220> FEATURE:
<221> NAME/KEY: MISC_FEATURE
<222> LOCATION: (155)..(155)
<223> OTHER INFORMATION: X is Asn, Asp, Gln, or Glu
<220> FEATURE:
<221> NAME/KEY: MISC_FEATURE
<222> LOCATION: (171)..(171)
<223> OTHER INFORMATION: X is Asn, Asp, Gln, or Glu
<220> FEATURE:
<221> NAME/KEY: MISC_FEATURE
<222> LOCATION: (180)..(180)
<223> OTHER INFORMATION: X is Asn, Asp, Gln, or Glu
<220> FEATURE:
<221> NAME/KEY: MISC_FEATURE
<222> LOCATION: (189)..(189)
<223> OTHER INFORMATION: X is Asn, Asp, Gln, or Glu
<220> FEATURE:
<221> NAME/KEY: MISC_FEATURE
<222> LOCATION: (195)..(195)
<223> OTHER INFORMATION: X is Ile or Val
<220> FEATURE:
<221> NAME/KEY: MISC_FEATURE
<222> LOCATION: (204)..(204)
<223> OTHER INFORMATION: X is Ile or Val
<220> FEATURE:
<221> NAME/KEY: MISC_FEATURE
<222> LOCATION: (205)..(205)
<223> OTHER INFORMATION: X is Asn, Asp, Gln, or Glu
<220> FEATURE:
<221> NAME/KEY: MISC_FEATURE
<222> LOCATION: (208)..(208)
<223> OTHER INFORMATION: X is Ile or Val
<220> FEATURE:
<221> NAME/KEY: MISC_FEATURE
<222> LOCATION: (233)..(233)
<223> OTHER INFORMATION: X is Ile or Val

<400> SEQUENCE: 14

Gly Asn Leu Glu Arg Arg Val Pro Gly Val Leu Trp Gly Xaa Val Gln
1               5                   10                  15

Ala Arg Ala Ala Trp Leu Asp Leu Pro Gly Asp Arg Ile Ala Ile Asn
            20                  25                  30

Val Ala Ala Gly Xaa Val Asn Pro Leu Thr Ala Glu Val Xaa His Ser
        35                  40                  45

Glu Lys Val Val Pro Ile Xaa Glu Asp Pro Lys Val Pro Pro Asp Leu
    50                  55                  60

Ala Gly Xaa Thr Pro Ala Xaa Xaa Leu Ala Leu Tyr Thr Ser Gly Thr
65                  70                  75                  80

Thr Gly Val Pro Lys Gly Val Xaa His Ser Val Ser Xaa Gly Thr Xaa
```

|     |     |     |     | 85  |     |     |     | 90  |     |     |     | 95  |     |
| --- | --- | --- | --- | --- | --- | --- | --- | --- | --- | --- | --- | --- | --- |
| Leu | Leu | Pro | Xaa | His | Xaa | Phe | Met | Xaa | Gly | Val | Leu | Leu | Asp | Phe | Lys |
|     |     |     | 100 |     |     |     |     | 105 |     |     |     |     | 110 |

Ser Gly Val Pro Trp Leu Gln Leu Arg Leu Gly Gly Ala Leu Val Arg
        115                 120                 125

Ala Gly Tyr Gly Xaa Thr Glu Ser Pro Val Ala Asn Ala Gly Leu Glu
        130                 135                 140

Gly Pro Pro Lys Xaa Xaa Gly Pro Val Gly Xaa Leu Val Arg Gly Val
145                 150                 155                 160

Met Gly Tyr Pro Thr Ala Glu Leu Thr Ser Xaa Gly Phe Leu Thr Gly
                165                 170                 175

Asp Ala Ile Xaa Ala Asp Gly Arg Ile Asp Arg Lys Xaa Ile Ile Lys
                180                 185                 190

Ser Gly Xaa Pro Glu Ile Glu Leu Ala His Pro Xaa Xaa Ala Val Xaa
        195                 200                 205

Gly Ala Lys Gly Glu Val Leu Val Thr Gly Leu Arg Ala Leu Pro Lys
        210                 215                 220

His Phe Val Leu Pro Thr Gly Lys Xaa Leu Leu Arg Lys Ala
225                 230                 235

<210> SEQ ID NO 15
<211> LENGTH: 44
<212> TYPE: DNA
<213> ORGANISM: artificial
<220> FEATURE:
<223> OTHER INFORMATION: Oligonucleotide primer

<400> SEQUENCE: 15
agtcggatcc gccgccacca tggcaatgaa acgtctcgga accc                44

<210> SEQ ID NO 16
<211> LENGTH: 29
<212> TYPE: DNA
<213> ORGANISM: artificial
<220> FEATURE:
<223> OTHER INFORMATION: Oligonucleotide primer

<400> SEQUENCE: 16
agtcggtacc ttacttgcgg gttcgggcg                                 29

<210> SEQ ID NO 17
<211> LENGTH: 51
<212> TYPE: DNA
<213> ORGANISM: artificial
<220> FEATURE:
<223> OTHER INFORMATION: Oligonucleotide primer

<400> SEQUENCE: 17
ataagaatgc ggccgcacca tgagcgaaga aagcttattc gagtcttctc c         51

<210> SEQ ID NO 18
<211> LENGTH: 32
<212> TYPE: DNA
<213> ORGANISM: artificial
<220> FEATURE:
<223> OTHER INFORMATION: Oligonucleotide primer

<400> SEQUENCE: 18
gggccttaat taattatttc aaagtcttca ac                             32

<210> SEQ ID NO 19

-continued

```
<211> LENGTH: 20
<212> TYPE: DNA
<213> ORGANISM: artificial
<220> FEATURE:
<223> OTHER INFORMATION: Oligonucleotide primer

<400> SEQUENCE: 19
agagtttgat cmtggctcag                                            20

<210> SEQ ID NO 20
<211> LENGTH: 20
<212> TYPE: DNA
<213> ORGANISM: artificial
<220> FEATURE:
<223> OTHER INFORMATION: Oligonucleotide primer
<220> FEATURE:
<221> NAME/KEY: misc_feature
<222> LOCATION: (15)..(15)
<223> OTHER INFORMATION: n is a, c, g, or t

<400> SEQUENCE: 20
aaggaggtga tccanccrca                                            20

<210> SEQ ID NO 21
<211> LENGTH: 7
<212> TYPE: PRT
<213> ORGANISM: artificial
<220> FEATURE:
<223> OTHER INFORMATION: catalytic motif
<220> FEATURE:
<221> NAME/KEY: MISC_FEATURE
<222> LOCATION: (3)..(5)
<223> OTHER INFORMATION: X is any amino acid

<400> SEQUENCE: 21

His His Xaa Xaa Xaa Asp Gly
1               5
```

ISOPRENOID WAX ESTER SYNTHASES, ISOPRENOID ACYL COA-SYNTHETASES, AND USES THEREOF

CONTINUING APPLICATION DATA

This application claims the benefit of U.S. Provisional Application Ser. No. 60/966,272, filed Aug. 27, 2007, which is incorporated by reference herein.

BACKGROUND

The exhaustion of fossil fuels is an eminent concern facing the industrialized world. With an ever-growing energy demand, the need for sustainable alternative renewable fuels is greatly needed. In addition, there is the negative impact linking increased carbon emissions with the burning of petroleum products to global warming.

Renewable liquid hydrocarbon-based fuels such as biodiesel are a potential candidate to resolve these energy concerns due to its high energy density and maintaining a neutral carbon footprint. The use of biodiesel maintains a balanced carbon dioxide cycle, as the carbon is recycled through renewable biological materials without releasing additional carbon into the atmosphere as petroleum based fossil fuels. Biodiesel is a monoalkyl ester of fatty acids and is nontoxic; it does not contain sulfur, aromatic hydrocarbons, or other toxic side-products linked to pollution found in petroleum diesel. It can also act as a lubricant in diesel engines thus reducing wear on engine parts. Pure biodiesel or mixtures of biodiesel and petroleum-based diesel can be used in unmodified diesel engines without changing the current infrastructure to distribute it.

Current manufacturing methods of biodiesel use vegetable oils for production; the broad use of it is hindered by the extensive acreage required for sufficient production of oil-seed crops from such sources as palm oil in south East Asia, rapeseed in Europe, and soybean in North America (Kalscheuer et al., 2006. Microbiology 152:2529-36). Vegetable oil is a triacylglycerol (TAG) neutral lipid that can be burned in modified diesel engines, however, the viscosity is high and it doesn't burn completely thus leaving an oily residue. The current method for biodiesel production is alcoholysis of vegetable oil, which uses methanol to transesterify the glycerol group away from the fatty acid groups forming a fatty acid methylester (FAME). Additives can be combined with FAMEs to decrease viscosity and using desaturated fatty acids can make biodiesel less viscous at lower temperatures where saturated FAMEs would gel (using desaturated oils such as oleic acid).

Another biodiesel source being investigated is jojoba wax oil, which is composed of a long-chain fatty alcohol that is transesterified with methanol (Canoira et al., 2006. Biomass and Bioenergy 30:76-81; Verschuren and Nugteren. 1989. Food Chem Toxicol 27:45-8; Wisniak, 1977. Prog Chem Fats Other Lipids 15:167-218). However, jojoba oil is more expensive to harvest and process compared to vegetable oils (Kalscheuer et al., 2006. Appl Environ Microbiol 72:1373-9).

Enzymatic attempts at making biodiesel have also been investigated using lipases (Akoh et al., 2007. J Agric Food Chem 55:8995-9005). Lipases are alpha-beta hydrolases that break down neutral lipids such as TAGs. However, if lipases are in a solvent system (i.e. toulene), lipases will perform a transesterification reaction exchanging the glycerol for methyl alcohol functional groups. Lipases can either be immobilized or expressed in recombinant cells that are imbedded onto a matrix and are emulsified with vegetable oils and methanol to perform the transesterification synthesis.

However, current problems with the transesterification process include excessive accumulations of glycerol byproducts and the continued use of toxic, petroleum-derived methanol. The methanol used for FAME synthesis is produced from natural gas; therefore with the use of fossil fuel petroleum component, FAME-based biodiesel is not truly a renewable biofuel. In addition, the transesterification process and subsequent purification steps are more expensive and energy consuming, thus reducing the energy yield and increasing the costs to make biodiesel (Kalscheuer et al., 2006. Microbiology 152:2529-36).

The first microbial wax ester synthase/acyltransferase (WS/DGAT) was characterized from *Acinetobacter baylyi* ADP1 and showed substrate promiscuity (Stoveken et al., 2005. J Bacteriol 187:1369-76). WS/DGAT has also been heterologously expressed in microbial cell lines such as *Pseudomonas citronellolis* (Kalscheuer and Steinbüchel. 2003. J Biol Chem 278:8075-82) creating wax esters and fatty acid butyl esters (FABEs), which have also been synthesized in recombinant *Escherichia coli* (Kalscheuer et al., 2006. Microbiology 152:2529-36). WS/DGAT has also been expressed in eukaryotic hosts creating TAGs, fatty acid ethyl esters (FAEEs) and fatty acid isoamyl esters (FAIES) in recombinant *Saccharomyces cerevisiae* (Kalscheuer et al., 2004. Appl Environ Microbiol 70:7119-25). Furthermore, wax diesters and wax thioesters have been synthesized in mutant *A. baylyi* strain ADP1 acr1VKm (Kalscheuer and Steinbüchel. 2003. J Biol Chem 278:8075-82; Uthoff et al., 2005. Appl Environ Microbiol 71:790-6). In 2006, Kalscheuer et al created a FAEE termed 'microdiesel' where ethanol-producing genes from *Zymomonas mobilis* (Carvalhal et al., 1996. Revista De Microbiologia 27:263-267) and the acyltransferase, WS/DGAT enzyme from *Acinetobacter baylyi* ADP1, were heterologously expressed in *E. coli* strain harboring a plasmid with all three genes. FAME and FAEE are similar in their chemical and physical combustion properties (Antoni et al., 2007. Appl Microbiol Biotechnol 77:23-35; Kalscheuer et al., 2006. Microbiology 152:2529-36).

However, *E. coli* is often not a suitable host for the creation of the biodiesel. The FAEEs yields were below the requirements of a sustainable industrial process; therefore fatty acids had to be supplemented to the recombinant *E. coli* strain in the form of sodium oleate (Kalscheuer et al., 2006. Microbiology 152:2529-36). De novo fatty-acid biosynthesis in *E. coli* does not provide ample acyl substrates for the *Acinetobacter* WS/DGAT-mediated FAEE synthesis, which indicates that this microbe may not be the ideal host for biodiesel production.

Furthermore, the expression host determines the types of acyl esters synthesized by *Acinetobacter* WS/DGAT based upon the biochemical/physiological background and the access to substrates (i.e. ethanol) made available either by natural metabolism, medium supplementation, or genetic engineering.

Neutral lipid biosynthesis is ubiquitous in nature and occurs in animals, plants, and microbes. Microorganisms have been reported to synthesize TAGs (Wältermann et al., 2005. Mol. Microbiol. 55:750-763), polyhydroxyalkonates (PHAs) (Steinbüchel, 2001. Macromol. Biosci. 1:1-24), and wax esters (WEs) (Wältermann and Steinbüchel. 2005. J. Bacteriol. 187:3607-3619). Neutral lipids accumulate as inclusion bodies within the microbial cell, and their purpose is to serve as carbon and energy storage under growth-limiting conditions. PHAs are composed of aliphatic monomeric unit polyesters, which are the most abundant class of neutral lipids in microbial species (Steinbüchel, 2001. Macromol. Biosci. 1:1-24). It is believed that neutral lipid inclusion bodies not only serve as an energy storage but also remove fatty acids that may cause damage to the bacterial cell membrane (Alvarez et al., 2002. Microbiology 148:1407-1412). Until recently, only microbial PHA biosynthesis has been investigated, and their biochemistry and metabolism has been well described (Steinbüchel, 2001. Macromol. Biosci. 1:1-24). The enzymes involved in microbial TAG biosynthesis and WE have only very recently been identified (Daniel et al., 2004. J. Bacteriol. 186:5017-5030; Kalscheuer and Steinbüchel. 2003. J. Biol. Chem. 278:8075-8082; Wältermann et al., 2000. Microbiology 146:1143-1149; Wältermann et al., 2007. Biochemie 89:230-242).

Microbial WEs have been found in *Mycobacterium* (Daniel et al., 2004. J. Bacteriol. 186:5017-5030), *Rhodococcus* (Alvarez et al., 2002. Microbiology 148:1407-1412), *Acinetobacter* (Alvarez et al., 1997. Appl. Microbiol. Biotechnol. 47:132-139), and *Marinobacter* (Rontani et al., 2003. 69:4167-4176; Rontani et al., 1999. Appl. Environ. Microbiol. 65:221-230) strains that grow in environments where a carbon source (such as petroleum hydrocarbons [Ishige et al., 2003. Curr. Opin. Microbiol. 6:244-250] and gluconate [Kalscheuer and Steinbüchel. 2003. J. Biol. Chem. 278:8075-8082]) may be abundant relative to other nutrients such as phosphorous and nitrogen. Acyl WEs are synthesized from long-chain fatty alcohol and fatty acyl-coenzyme A (CoA) substrates. Another class of WEs is the isoprenoid WEs that are made from branched, long-chained isoprenoyl alcohol and isoprene fatty acid substrates. Isoprenoid WEs have been identified as a way to provide energy storage in *Marinobacter* species (Rontani et al., 2003. 69:4167-4176; Rontani et al., 1997. Appl. Environ. Microbiol. 63:636-643; Rontani et al., 1999. Appl. Environ. Microbiol. 65:221-230). *Marinobacter* species grow in marine sediment materials where there is an abundance of recalcitrant acyclic isoprenoid alcohols such as farnesol and phytol, which are derived from (bacterio) chlorophyll molecules (Rontani et al., 1997. Appl. Environ. Microbiol. 63:636-643; Rontani et al., 1999. Appl. Environ. Microbiol. 65:221-230).

A microbial WS/DGAT capable of catalyzing WE synthesis and, to a lesser degree, TAG synthesis was identified in the gamma proteobacterium *Acinetobacter baylyi* ADP1 (Kalscheuer and Steinbüchel. 2003. J. Biol. Chem. 278:8075-8082; Stöveken et al., 2005. J. Bacteriol. 187:1369-1376; Uthoff et al., 2005. Appl. Environ. Microbiol. 71:790-796). The *A. baylyi* ADP1 WS/DGAT contains the catalytic motif HHXXXDG (SEQ ID NO:21) that is involved in the acyl-transferase reaction (Pfam domain PF00668) (Kalscheuer and Steinbüchel. 2003. J. Biol. Chem. 278:8075-8082). This motif has been found in numerous sequenced genomes of microbial strains that are known to make WEs and/or TAGs and is also found in the condensation domain of some nonribosomal peptide synthetase (NRPS) modules. Mutations within this domain have been shown to abolish NRPS activity (Stachelhaus et al., 1998. J. Biol. Chem. 273:22773-22781; Wältermann et al., 2007. Biochemie 89:230-242). Two WS/DGAT homologues from the marine hydrocarbonoclastic bacterium *Alcanivorax borkumensis* (Kalscheuer et al., 2007. J. Bacteriol. 189:918-928) have been reported.

The gamma proteobacteria *Marinobacter hydrocarbonoclasticus* DSM 8798 has been shown to synthesize an isoprenoid WE when grown on phytol as the sole carbon source and under nitrogen-limiting conditions (Rontani et al., 2003. 69:4167-4176; Rontani et al., 1999. Appl. Environ. Microbiol. 65:221-230). It has been proposed that exogenous phytol is transported into the cell, where it is converted into an intermediate aldehyde (phytenal) that is then further oxidized into the isoprenic fatty acid phytenic acid, which may be hydrogenated into phytanic acid (Rontani et al., 1999. Appl. Environ. Microbiol. 65:221-230). Phytanic acid is then esterified with phytol to form an isoprenoid WE.

SUMMARY OF THE INVENTION

The present invention presents an advance in the art of producing esters. Prior to this invention, the enzymes involved in isoprenoid wax ester synthesis were not known. As disclosed herein, two enzymes have been identified that provide a pathway for the production of esters, including isoprenoid wax esters and fatty acid alkyl esters, such as fatty acid methyl esters and fatty acid ethyl esters.

The present invention provides isolated polynucleotides. Isolated polynucleotides include a nucleotide sequence encoding a polypeptide having isoprenoid wax ester synthase activity, wherein the amino acid sequence of the polypeptide and the amino acid sequence of SEQ ID NO:2 have at least 80% identity, or the full complement of the nucleotide sequence thereof; a nucleotide sequence encoding a polypeptide having isoprenoid wax ester synthase activity, wherein the nucleotide sequence of the isolated polynucleotide and the nucleotide sequence of SEQ ID NO:1 have at least 80% identity, or the full complement of the nucleotide sequence thereof; a nucleotide sequence encoding a polypeptide having isoprenoid acyl CoA-synthetase activity, wherein the amino acid sequence of the polypeptide and the amino acid sequence of SEQ ID NO:4 have at least 80% identity, or the full complement of the nucleotide sequence thereof; or a nucleotide sequence encoding a polypeptide having isoprenoid acyl CoA-synthetase activity, wherein the nucleotide sequence of the isolated polynucleotide and the nucleotide sequence of SEQ ID NO:3 have at least 80% identity, or the full complement of the nucleotide sequence thereof. An isolated polynucleotide may be operably linked to at least one regulatory sequence, and may include heterologous nucleotides.

The present invention further provides a vector that includes an isolated polynucleotide of the present invention. Also included in the present invention is a genetically modified microbe, such as a eukaryotic microbe, e.g., a yeast, or a prokaryotic microbe, that contains an exogenous polynucleotide, wherein the exogenous polynucleotide is an isolated polynucleotide of the present invention.

Also provided by the present invention are isolated polypeptides. In one aspect, an isolated polypeptide has isoprenoid wax ester synthase activity, wherein the polypeptide includes an amino acid sequence, wherein the amino acid sequence and the amino acid sequence of SEQ ID NO:2 have at least 80% identity. In another aspect, an isolated polypeptide has isoprenoid acyl CoA-synthetase activity, wherein the polypeptide includes an amino acid sequence, wherein the amino acid sequence and the amino acid sequence of SEQ ID NO:4 have at least 80% identity. The present invention also includes a genetically modified microbe containing an exogenous polypeptide, wherein the exogenous polypeptide is an isolated polypeptide of the present invention.

The present invention also provides methods for using the polynucleotides and polypeptides of the present invention. In one aspect, the methods include providing a genetically modified microbe, wherein the microbe includes an exogenous polynucleotide having a nucleotide sequence encoding a polypeptide having isoprenoid wax ester synthase activity, wherein the amino acid sequence of the polypeptide and the amino acid sequence of SEQ ID NO:2 have at least 80% identity, or the full complement of the nucleotide sequence thereof, and incubating the microbe under conditions suitable for the production of an ester. The microbe may be a eukaryotic microbe, such as a yeast, or a prokaryotic microbe. The method may further include isolating or purifying the ester. The esters produced may include a fatty acid ethyl ester, a fatty acid methyl ester, or a combination thereof. The esters produced may include a fatty acid-derived group of at least $C_8$, an alcohol-derived group of $C_1$ or $C_2$, or a combination thereof. The esters produced may include an isoprenoid-derived group of at least $C_8$, an alcohol-derived group of $C_1$ or $C_2$, or a combination thereof. The fatty acid-derived group and the isoprenoid-derived group may be unsaturated or saturated.

Optionally, the genetically modified microbe may also include a second exogenous polynucleotide having a nucleotide sequence encoding a polypeptide having isoprenoid acyl CoA-synthetase activity, wherein the amino acid sequence of the polypeptide and the amino acid sequence of SEQ ID NO:4 have at least 80% identity, or the full complement of the nucleotide sequence thereof.

As used herein, an "isolated" substance is one that has been removed from its natural environment, produced using recombinant techniques, or chemically or enzymatically synthesized. For instance, a polypeptide, a polynucleotide, an ester, or a CoA-activated compound can be isolated. Preferably, a substance is purified, i.e., is at least 60% free, preferably at least 75% free, and most preferably at least 90% free from other components with which they are naturally associated.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region" and "coding sequence" are used interchangeably and refer to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

A polynucleotide that includes a coding region may include heterologous nucleotides that flank one or both sides of the coding region. As used herein, "heterologous nucleotides" refer to nucleotides that are not normally present flanking a coding region that is present in a wild-type cell. For instance, a coding region present in a wild-type microbe and encoding an Acs polypeptide is flanked by homologous sequences, and any other nucleotide sequence flanking the coding region is considered to be heterologous. Examples of heterologous nucleotides include, but are not limited to regulatory sequences. Typically, heterologous nucleotides are present in a polynucleotide of the present invention through the use of standard genetic and/or recombinant methodologies well known to one skilled in the art. A polynucleotide of the present invention may be included in a suitable vector.

As used herein, an "exogenous polynucleotide" refers to a polynucleotide that is not normally or naturally found in a microbe. As used herein, the term "endogenous polynucleotide" refers to a polynucleotide that is normally or naturally found in a cell microbe. An "endogenous polynucleotide" is also referred to as a "native polynucleotide."

The terms "complement" and "complementary" as used herein, refer to the ability of two single stranded polynucleotides to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The term "substantial complement" and cognates thereof as used herein, refer to a polynucleotide that is capable of selectively hybridizing to a specified polynucleotide under stringent hybridization conditions. Stringent hybridization can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically substantially complementary to a second polynucleotide if hybridization occurs between the polynucleotide and the second polynucleotide. As used herein, "specific hybridization" refers to hybridization between two polynucleotides under stringent hybridization conditions.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, enzyme, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

As used herein, "isoprenoid wax ester synthase activity" refers to the ability of a polypeptide to catalyze the formation of an ester using a CoA-activated compound and an alcohol as substrates. An example of an ester is an isoprenoid wax ester, formed using phytanoyl-CoA and isoprenoid alcohols, such as phytol or farnesol, as substrates. In particular, "isoprenoid wax ester synthase activity" refers to the ability of a polypeptide to catalyze the formation of a fatty acid alkyl ester of a long chain fatty acid, preferably, oleic acid, with a short chain alcohol, preferably ethanol.

As used herein, "isoprenoid acyl CoA-synthetase activity" refers to the ability of a polypeptide to produce CoA-activated compound, such as a CoA-activated fatty acid or a CoA-activated isoprenoid. In particular, "isoprenoid acyl CoA-synthetase activity" refers to the ability of a polypeptide to catalytically convert phytanic acid into phytanoyl-CoA.

As used herein, "identity" refers to sequence similarity between two polypeptides or two polynucleotides. The sequence similarity between two polypeptides is determined by aligning the residues of the two polypeptides (e.g., a candidate amino acid sequence and a reference amino acid sequence, such as SEQ ID NO:2 or SEQ ID NO:4) to optimize the number of identical amino acids along the lengths of their sequences; gaps in either or both sequences are permitted in making the alignment in order to optimize the number of shared amino acids, although the amino acids in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as the BESTFIT algorithm in the GCG package (Madison Wis.), or the Blastp program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, sequence similarity between two amino acid sequences is determined using the Blastp program of the BLAST 2 search algorithm. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "identities."

The sequence similarity between two polynucleotides is determined by aligning the residues of the two polynucleotides (e.g., a candidate nucleotide sequence and a reference nucleotide sequence, such as SEQ ID NO:1 or SEQ ID NO:3) to optimize the number of identical nucleotides along the lengths of their sequences; gaps in either or both sequences are permitted in making the alignment in order to optimize the number of shared nucleotides, although the nucleotides in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as GCG FastA (Genetics Computer Group, Madison, Wis.), MacVector 4.5 (Kodak/IBI software package) or other suitable sequencing programs or methods known in the art. Preferably, sequence similarity between two nucleotide sequences is determined using the Blastn program of the BLAST 2 search algorithm, as described by Tatusova, et al. (1999, *FEMS Microbiol Lett.*, 174:247-250), and available through the World Wide Web, for instance at the internet site maintained by the National Center for Biotechnology Information, National Institutes of Health. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. In the comparison of two nucleotide sequences using the BLAST search algorithm, sequence similarity is referred to as "identities."

Conditions that "allow" an event to occur or conditions that are "suitable" for an event to occur, such as an enzymatic reaction, or "suitable" conditions are conditions that do not prevent such events from occurring. Thus, these conditions permit, enhance, facilitate, and/or are conducive to the event. Such conditions, known in the art and described herein, may depend upon, for example, the enzyme being used.

As used herein, a polypeptide "fragment" includes any polypeptide which retains at least some of the activity of the corresponding native polypeptide. Examples of fragments of polypeptides described herein include, but are not limited to, proteolytic fragments and deletion fragments.

As used herein, a "microbe" refers to a prokaryotic cell, including bacteria and archaea, and a eukaryotic cell, including fungi (such as yeast) and algae.

As used herein, "genetically modified microbe" refers to a microbe into which has been introduced an exogenous polynucleotide, e.g., an expression vector. For example, a microbe is a genetically modified microbe by virtue of introduction into a suitable microbe of an exogenous polynucleotide that is foreign to the microbe. "Genetically modified microbe" also refers to a microbe that has been genetically manipulated such that endogenous nucleotides have been altered. For example, a microbe is a genetically modified microbe by virtue of introduction into a suitable microbe of an alteration of endogenous nucleotides. For instance, an endogenous coding region could be deleted or mutagenized. Such mutations may result in a polypeptide having a different amino acid sequence than was encoded by the endogenous polynucleotide. Another example of a genetically modified microbe is one having an altered regulatory sequence, such as a promoter, to result in increased or decreased expression of an operably linked endogenous coding region.

As used herein, an antibody that can "specifically bind" or is "specific for" a polypeptide is an antibody that interacts only with an epitope of the antigen that induced the synthesis of the antibody, or interacts with a structurally related epitope.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2 shows a multiple protein sequence alignment of *Acinetobacter* WS/DGAT (ADP1) with four putative WS coding regions cloned from *M. hydrocarbonoclasticus* strain 8798 (WS1 to -4). Identical and similar amino acids are marked black and gray, respectively. The WS4 gene contains a stop codon signified with an "X" at position 350 (denoted with an asterisk). The region outlined by a black box corresponds to the putative conserved acyltransferase catalytic domain, HHXXXDG (SEQ ID NO:21; Kalscheuer and Steinbüchel. 2003. J. Biol. Chem. 278:8075-8082). ADP1, SEQ ID NO:7; WS1, SEQ ID NO:8; WS2, SEQ ID NO:2; WS3, SEQ ID NO:9; WS4, SEQ ID NO:10.

FIG. 3 shows two alkane metabolism operons identified in the *M. aquaeolei* VT8 final draft genome sequence. Co-ordinates of open reading frames (ORFs) identified in the *Marinobacter aquaeolei* VT8 genome sequence (released by the DOE Joint Genome Institute (available on the world wide web)). Alkane gene clusters 1 and 2 on the completed chromosome (4,326,849 bp) encode putative enzymes for alkane hydrocarbon metabolism. The medium-chain acyl CoA synthetase (Acs1) is found in gene cluster 1. A second, putative medium-chain CoA synthetase was annotated in the final draft (marked Acs?). Arrows correspond to 3' end of the contigs. ORF0163 and ORF435 in gene cluster 1 are repeated transposase sequences with 100% sequence identity on reverse complemented strands. The symbol, //, corresponds to breaks in the coordinates of genes in relation to alkane metabolizing genes. Due to the observed high DNA sequence identity of the WS genes cloned from strain 8798 (>90%, see Table 1), it is assumed that the *M. hydrocarbonoclasticus* 8798 genome may contain the same gene arrangement.

FIG. 11 shows the heterologous expression of WS2 in TAG deficient yeast strain. TLC plate of chloroform extracts from strain H1246, which has a TAG-negative phenotype, expressing WS2 (labeled WS2) and without (labeled ---) was spiked with 0.1% oleic acid and 5% ethanol grown in 500 ml flask 250 ml of 8% glucose SD-Uracil minimal media FAEE was observed with WS2 compared to an ethyloleate standard (labeled Std).

FIG. 14 shows an assay of WS2 kinetics on ethanol and oleoyl-CoA. Steady state analysis of WS2 using 10 μM-250 μM of ethanol and 500 μM of oleoyl-CoA. The double reciprocal plot (bottom) was used to calculate the $K_m$, which was measured to be 17 μM and a $V_{max}$ 1250 μmol (mg/min)$^{-1}$.

FIG. 15 shows an assay of WS2 Kinetics on oleoyl-CoA and ethanol. Steady state analysis of WS2 using a range 10 μM-250 μM of oleoyl-CoA and 500 μM of ethanol. Double reciprocal plot (bottom) may indicate that interfacial activation is seen when higher concentrations of oleoyl-CoA (>100 μM) are used thus quickly accelerating turn-over of ethyloleate. The $K_m$ was calculated to be 23 μM and $V_{max}$ of 1667 μmol (mg/min)$^{-1}$.

FIG. 19. Multiple protein alignment of SEQ ID NO:4 (Acs2), with *Pseudomonas putida* FadD (FadD_Pp, SEQ ID NO:11), *P. putida* AlkK (AlkK_Pp, SEQ ID NO:12), and *P. aeruginosa* FadD (FadD_Pa, SEQ ID NO:13). Identical and conserved amino acids are marked in black and grey, respectively. The consensus for the four proteins is also shown (SEQ ID NO:14). Consensus symbols: ! is I or V; $ is L or M; % is F or Y; and # is N, D, Q, or E.

FIG. 20. A. The nucleotide sequence of an open reading frame encoding an Acs polypeptide. The open reading frame is nucleotides 101-1777 (beginning at the ATG and ending at the last nucleotide of the stop codon), and is designated SEQ ID NO:3 (Genbank accession: EF219373). The entire nucleotide sequence depicted is SEQ ID NO:6. Nucleotides 1-100 and 1778-1877 are homologous sequences present in the *M. hydrocarbonoclasticus* strain DSM8798 flanking the Acs open reading frame. B. The nucleotide sequence of an open reading frame encoding a WS polypeptide. The open reading frame is nucleotides 101-1522 (beginning at the ATG and ending at the last nucleotide of the stop codon), and is designated SEQ ID NO:1 (Genbank accession: EF219377). The entire nucleotide sequence depicted is SEQ ID NO:5. Nucleotides 1-100 and 1523-1623 are homologous sequences present in the *M. hydrocarbonoclasticus* strain DSM8798 flanking the WS open reading frame. See Hisanaga et al., (J. Biol. Chem., 2004 Jul. 23; 279(30):31717-26).

DETAILED DESCRIPTION OF ILLUSTRATIVE EMBODIMENTS

Figure 1:
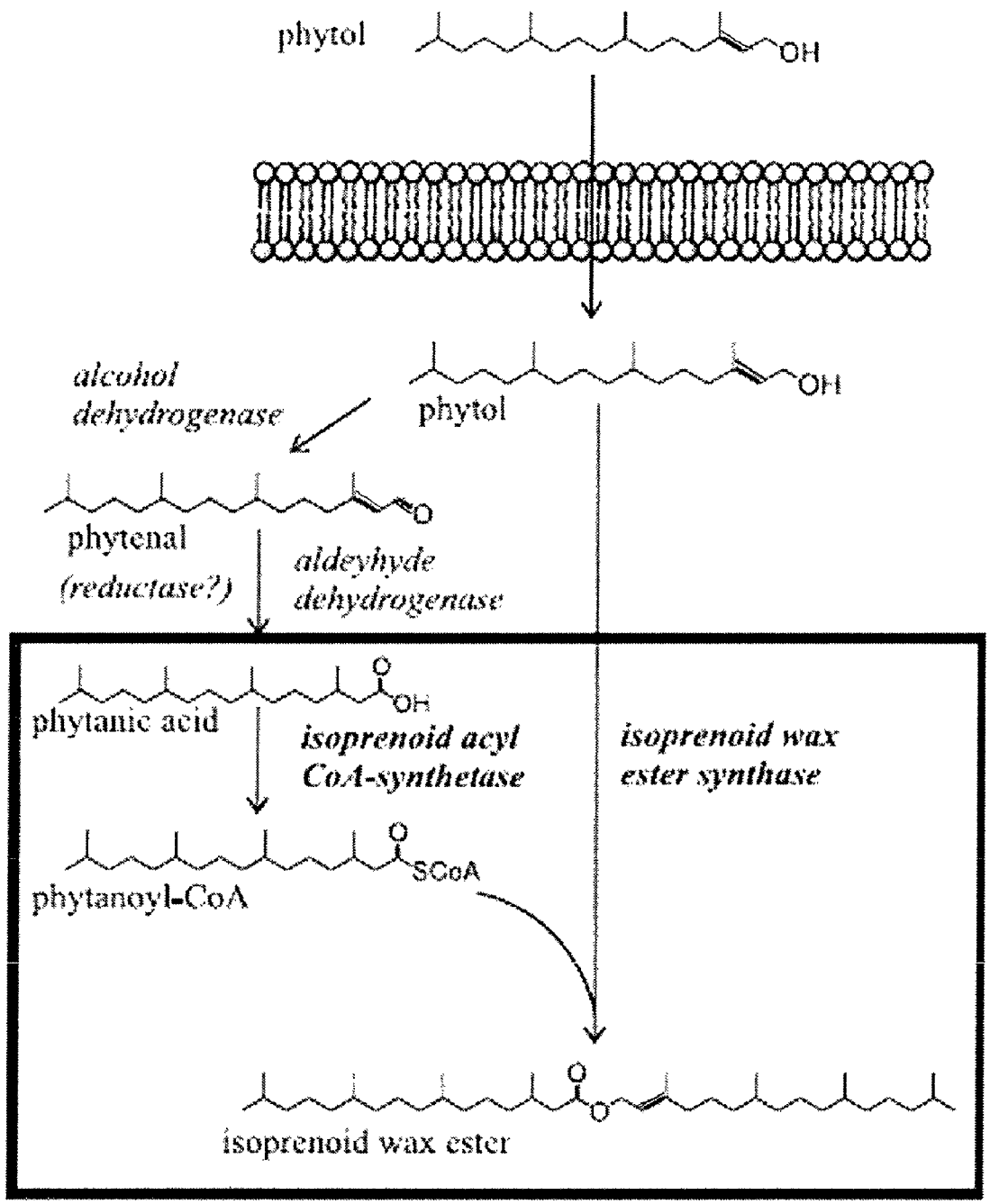
FIG. 1 shows a proposed pathway for isoprenoid WE biosynthesis. Phytol is transported into *M. hydrocarbonoclasticus* by an unknown system and is reduced to phytenal by an alcohol dehydrogenase. Phytenal is further oxidized into phytenic acid by an aldehyde dehydrogenase. Concurrently, phytanic acid (saturated by an unknown reductase (indicated as "reductase?," a saturated form of phytenic acid) is activated to phytanoyl-CoA by an isoprenoid/acyl-CoA synthetase. Phytanoyl-CoA and phytol are substrates for WS to form the isoprenoid WE product.

The present invention includes isolated polypeptides having isoprenoid acyl CoA-synthetase activity. A polypeptide having isoprenoid acyl CoA-synthetase activity catalytically converts phytanic acid into phytanoyl-CoA under suitable conditions. A polypeptide having isoprenoid acyl CoA-synthetase activity may also catalyze the CoA-activation of fatty acid substrates with chain lengths of at least $C_2$. For instance, a fatty acid substrate may have a chain length of at least $C_2$, at least $C_4$, at least $C_6$, at least $C_8$, at least $C_{10}$, or at least $C_{12}$. For instance, a fatty acid substrate may have a chain length of no greater than $C_{12}$, no greater than $C_{14}$, no greater than $C_{16}$, no greater than $C_{18}$, no greater than $C_{20}$, or no greater than $C_{22}$. Such fatty acids may be saturated or unsaturated, and may be branched or unbranched. A polypeptide having isoprenoid acyl CoA-synthetase activity may also catalyze the CoA-activation of isoprenoid substrates with chain lengths of at least $C_5$. For instance, an isoprenoid substrate may have a chain length of at least $C_5$ or at least $C_{10}$. For instance, an isoprenoid substrate may have a chain length of no greater than $C_{15}$ or no greater than $C_{20}$. Such isoprenoids may be saturated or unsaturated, and may be linear or cyclic.

Whether a polypeptide has isoprenoid acyl CoA-synthetase activity may be determined by in vitro assays. Preferably, an in vitro assay is carried out as described previously (Trivedi et al., 2004, Nature, 428:441-445) with some modifications. Briefly, a reaction includes 50 mM Tris-HCl buffer (pH 7.5), 0.1% Triton X-100, 10 mM MgCl2, 5 mM TCEP, 0.1 U of inorganic pyrophosphatase, and as substrates 10 mM phytanic or fatty acids, preferably phytanic acid, 10 mM reduced coenzyme A (CoASH), 10 mM ATP, and 0.5 μg of the polypeptide being assayed for isoprenoid acyl CoA-synthetase activity. Preferably, the substrate is phytanic acid. The reaction is incubated for 20 minutes at 37° C. and stopped with 25 μl of 5% acetic acid, followed by HPLC analysis and/or liquid chromatography-mass spectrometry of the reaction products.

A polypeptide having isoprenoid acyl CoA-synthetase activity is referred to herein as an Acs polypeptide. An example of an Acs polypeptide is depicted at SEQ ID NO:4. Other examples of Acs polypeptides of the present invention include those having sequence similarity with the amino acid sequence of SEQ ID NO:4. An Acs polypeptide having sequence similarity with the amino acid sequence of SEQ ID NO:4 has isoprenoid acyl CoA-synthetase activity. An Acs polypeptide may be isolated from a microbe, such as a member of the genera *Marinobacter*, preferably *M. hydrocarbonoclasticus*, or may be produced using recombinant techniques, or chemically or enzymatically synthesized using routine methods.

Figure 19:
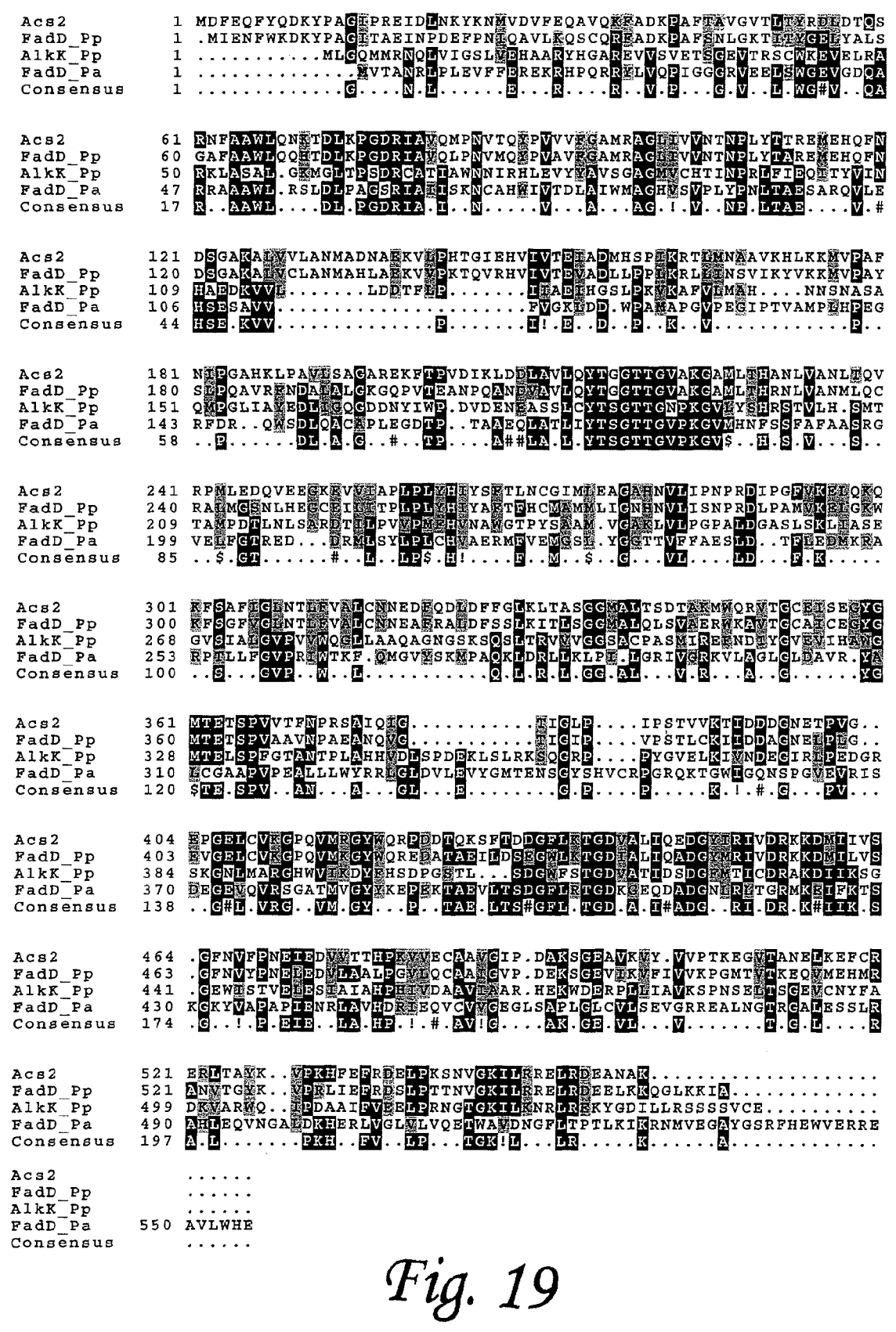

The amino acid sequence of an Acs polypeptide having sequence similarity to SEQ ID NO:4 may include conservative substitutions of amino acids present in SEQ ID NO:4. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) may generally be substituted for another amino acid without substantially altering the secondary and/or tertiary structure of a polypeptide. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids. SEQ ID NO:4 is shown in FIG. 19 in a multiple protein alignment with three other proteins having acyl-CoA synthetase activity. Identical and conserved amino acids are marked in black and grey, respectively.

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a polypeptide sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

The present invention also includes isolated polynucleotides encoding a polypeptide of the present invention, e.g., a polypeptide having isoprenoid acyl CoA-synthetase activity. A polynucleotide encoding a polypeptide having isoprenoid acyl CoA-synthetase activity is referred to herein as an Acs polynucleotide. Acs polynucleotides may have a nucleotide sequence encoding a polypeptide having the amino acid sequence shown in SEQ ID NO:4. An example of the class of nucleotide sequences encoding such a polypeptide is SEQ ID NO:3. It should be understood that a polynucleotide encoding an Acs polypeptide represented by SEQ ID NO:4 is not limited to the nucleotide sequence disclosed at SEQ ID NO:3, but also includes the class of polynucleotides encoding such polypeptides as a result of the degeneracy of the genetic code. For example, the naturally occurring nucleotide sequence SEQ ID NO:3 is but one member of the class of nucleotide sequences encoding a polypeptide having the amino acid sequence SEQ ID NO:4. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid.

An Acs polynucleotide of the present invention may have sequence similarity with the nucleotide sequence of SEQ ID NO:3. Acs polynucleotides having sequence similarity with the nucleotide sequence of SEQ ID NO:3 encode an Acs polypeptide. An Acs polynucleotide may be isolated from a microbe, such as a member of the genera *Marinobacter*, preferably *M. hydrocarbonoclasticus*, or may be produced using recombinant techniques, or chemically or enzymatically synthesized. An Acs polynucleotide of the present invention may further include heterologous nucleotides flanking the open reading frame encoding the Acs polynucleotide. Typically, heterologous nucleotides may be at the 5' end of the coding region, at the 3' end of the coding region, or the combination thereof. The number of heterologous nucleotides may be, for instance, at least 10, at least 100, or at least 1000.

The present invention also includes isolated polypeptides having isoprenoid wax ester synthase activity. A polypeptide having isoprenoid wax ester synthase activity catalyzes under suitable conditions the formation of esters. For instance, a polypeptide having isoprenoid wax ester synthase activity catalyzes isoprenoid wax ester formation using phytanoyl-CoA and isoprenoid alcohols, such as phytol or farnesol, as substrates. A polypeptide having isoprenoid wax ester synthase activity typically has a specific activity of at least 20 mmol mg$^{-1}$ min$^{-1}$, at least 40 mmol mg$^{-1}$ min$^{-1}$, or at least 60 mmol mg$^{-1}$ min$^{-1}$ when measured with palmitoyl-CoA and hexadecanol as substrates using the methods described in Example 1.

A polypeptide having isoprenoid wax ester synthase activity also catalyzes the formation of fatty acid alkyl esters using a CoA-activated fatty acid and an alcohol. The CoA-activated fatty acids that may be used as substrates may have chain lengths of at least $C_2$. For instance, a CoA-activated fatty acid substrate may have a chain length of at least $C_2$, at least $C_4$, at least $C_6$, at least $C_8$, at least $C_{10}$, or at least $C_{12}$. For instance, a CoA-activated fatty acid substrate may have a chain length of no greater than $C_{12}$, no greater than $C_{14}$, no greater than $C_{16}$, no greater than $C_{18}$, no greater than $C_{20}$, or no greater than $C_{22}$. Such CoA-activated fatty acids may be saturated or unsaturated, and may be branched or unbranched. The alcohol substrate used by a polypeptide having isoprenoid wax ester synthase activity may have chain length of at least $C_1$. For instance, an alcohol substrate may have a chain length of at least $C_1$, at least $C_2$, at least $C_3$, at least $C_4$, at least $C_5$, at least $C_6$, at least $C_7$, at least $C_8$, at least $C_9$, at least $C_{10}$, at least $C_{11}$, or at least $C_{12}$. For instance, an alcohol substrate may have a chain length of no greater than $C_{12}$, no greater than $C_{13}$, no greater than $C_{14}$, no greater than $C_{15}$, no greater than $C_{16}$, no greater than $C_{17}$, no greater than $C_{18}$, no greater than $C_{19}$, or no greater than $C_{20}$. The alcohol may be linear or cyclic. In some aspects, an alcohol substrate used by a polypeptide having isoprenoid wax ester synthase activity may use an alcohol such as methanol, ethanol, propanol, isopropanol, butanol, isobutanol, or hexanol as a substrate. Advantageously, a polypeptide of the present invention having isoprenoid wax ester synthase activity does not have any significant diacylglycerol acyltransferase activity, and thus the formation of fatty acid alkyl esters by such a polypeptide of the present invention typically results in low, preferably undetectable levels of triacylglycerols. Preferably, the amount of triacylglycerols produced by a polypeptide of the present invention having isoprenoid wax ester synthase activity and expressed in a microbe is no greater than 0.5%, no greater than 1%, no greater than 2%, no greater than 4%, no greater than 6%, no greater than 8%, or no greater than 10% of the cellular dry weight.

Whether a polypeptide has isoprenoid wax ester synthase activity may be determined by in vitro assays. Preferably, the assay is an in vitro/coupled assay using a polypeptide being assayed for isoprenoid wax ester synthase activity and an Acs polypeptide of the present invention, preferably SEQ ID NO:4. Preferably, the assay measures the ability of a polypeptide to catalytically add an alcohol to a fatty acid substrate. Preferably the alcohol is ethanol, and preferably the fatty acid substrate is oleic acid. Briefly, a stock solution of the fatty acid used in the assay may be prepared in 50 mM Tris-HCl buffer (pH 8) containing 1% gum arabic, 12.5 g bovine serum albumin/ml, 0.1% taurocholate, and 100 mM of fatty acid. The assay may be carried out in 500 μL reactions containing 50 mM Tris-HCl buffer pH 8.0, 10 mM MgCl2, 10 mM CoASH, 10 mM ATP, 5 mM TCEP, 0.1 U of inorganic pyrophosphatase, 0.25 µg of an Acs polypeptide and 0.5 µg of the polypeptide being tested for isoprenoid wax ester synthase activity, 12.5 µL of fatty acid stock solution and addition of alcohol solution, for instance, ethyl alcohol. The final concentration of each substrate is 250 µM. The assay is incubated at 37° C. overnight. The assay samples are extracted with 500 µL of chloroform:methanol (1:1 [vol/vol]), and the extracts analyzed by thin-layer chromatography (TLC) with Whatman normal phase silica gel 60 plates. The reaction products are separated using hexane:diethyl ether:acetic acid (90:10:1 [vol/vol/vol]). Reaction products can be compared to an appropriate standard. For instance, when oleate and ethanol are used as the substrate, the appropriate standard is ethyloleate.

A polypeptide having isoprenoid wax ester synthase activity is referred to herein as a WS polypeptide. An example of a WS polypeptide is depicted at SEQ ID NO:2. Other examples of WS polypeptides of the present invention include those having sequence similarity with the amino acid sequence of SEQ ID NO:2. A WS polypeptide having sequence similarity with the amino acid sequence of SEQ ID NO:2 has isoprenoid wax ester synthase activity. A WS polypeptide may be isolated from a microbe, such as a member of the genera *Marinobacter*, preferably *M. hydrocarbonoclasticus*, or may be produced using recombinant techniques, or chemically or enzymatically synthesized using routine methods.

The amino acid sequence of a WS polypeptide having sequence similarity to SEQ ID NO:2 may include conservative substitutions of amino acids present in SEQ ID NO:2. Conservative substitutions and guidance on making phenotypically silent amino acid substitutions are described above. SEQ ID NO:2 is shown in FIG. 2 (referred to as WS2 in the figure) in a multiple protein alignment with three other polypeptides, two of which have isoprenoid wax ester synthase activity (WS1 and WS2). Identical and conserved amino acids are marked in black and grey, respectively.

The present invention also includes isolated polynucleotides encoding a polypeptide of the present invention, e.g., a polypeptide having isoprenoid wax ester synthase activity. A polynucleotide encoding a polypeptide having isoprenoid wax ester synthase activity is referred to herein as a WS polynucleotide. WS polynucleotides may have a nucleotide sequence encoding a polypeptide having the amino acid sequence shown in SEQ ID NO:2. An example of the class of nucleotide sequences encoding such a polypeptide is SEQ ID NO:1. It should be understood that a polynucleotide encoding a WS polypeptide represented by SEQ ID NO:2 is not limited to the nucleotide sequence disclosed at SEQ ID NO:1, but also includes the class of polynucleotides encoding such polypeptides as a result of the degeneracy of the genetic code. For example, the naturally occurring nucleotide sequence SEQ ID NO:1 is but one member of the class of nucleotide sequences encoding a polypeptide having the amino acid sequence SEQ ID NO:2. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid.

A WS polynucleotide of the present invention may have sequence similarity with the nucleotide sequence of SEQ ID NO:1. WS polynucleotides having sequence similarity with the nucleotide sequence of SEQ ID NO:1 encode an WS polypeptide. A WS polynucleotide may be isolated from a microbe, such as a member of the genera *Marinobacter*, preferably *M. hydrocarbonoclasticus*, or may be produced using recombinant techniques, or chemically or enzymatically synthesized. A WS polynucleotide of the present invention may further include heterologous nucleotides flanking the open reading frame encoding the WS polynucleotide. Typically, heterologous nucleotides may be at the 5' end of the coding region, at the 3' end of the coding region, or the combination thereof. The number of heterologous nucleotides may be, for instance, at least 10, at least 100, or at least 1000.

The present invention also includes fragments of the polypeptides described herein, and the polynucleotides encoding such fragments, Acs polypeptides and WS polypeptides, such as SEQ ID NOs:2 and 4, respectively, as well as those polypeptides having structural similarity to SEQ ID NO:2 or SEQ ID NO:4. A polypeptide fragment may include a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 amino acid residues.

A polypeptide of the present invention or a fragment thereof may be expressed as a fusion polypeptide that includes a polypeptide of the present invention or a fragment thereof and an additional amino acid sequence. For instance, the additional amino acid sequence may be useful for purification of the fusion polypeptide by affinity chromatography. Various methods are available for the addition of such affinity purification moieties to proteins. Representative examples may be found in Hopp et al. (U.S. Pat. No. 4,703,004), Hopp et al. (U.S. Pat. No. 4,782,137), Sgarlato (U.S. Pat. No. 5,935,824), and Sharma Sgarlato (U.S. Pat. No. 5,594,115). In another example, the additional amino acid sequence may be a carrier polypeptide. The carrier polypeptide may be used to increase the immunogenicity of the fusion polypeptide to increase production of antibodies that specifically bind to a polypeptide of the invention. The invention is not limited by the types of carrier polypeptides that may be used to create fusion polypeptides. Examples of carrier polypeptides include, but are not limited to, keyhole limpet hemacyanin, bovine serum albumin, ovalbumin, mouse serum albumin, rabbit serum albumin, and the like.

A polynucleotide of the present invention may be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, Molecular Cloning: A Laboratory Manual., Cold Spring Harbor Laboratory Press (1989). A vector may provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and artificial chromosome vectors. Examples of viral vectors include, for instance, adenoviral vectors, adeno-associated viral vectors, lentiviral vectors, retroviral vectors, and herpes virus vectors. Typically, a vector is capable of replication in a microbial host, for instance, a fungus, such as *S. cerevisiae*, or a prokaryotic bacterium, such as *E. coli*. Preferably the vector is a plasmid.

Selection of a vector depends upon a variety of desired characteristics in the resulting construct, such as a selection marker, vector replication rate, and the like. In some aspects, suitable host cells for cloning or expressing the vectors herein include eukaryotic cells. Suitable eukaryotic cells include fungi, such as *S. cerevisiae* and *P. pastoris*. In other aspects, suitable host cells for cloning or expressing the vectors herein include prokaryotic cells. Suitable prokaryotic cells include eubacteria, such as gram-negative microbes, for example, *E. coli* and *Acinetobacter baylyi*, and members of the actinomycete group. Vectors may be introduced into a host cell using methods that are known and used routinely by the skilled person. For example, calcium phosphate precipitation, electroporation, heat shock, lipofection, microinjection, and viral-mediated nucleic acid transfer are common methods for introducing nucleic acids into host cells.

Polynucleotides of the present invention may be obtained from microbes, for instance, members of the genus *Marinobacter*, or produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known. Likewise, polypeptides of the present invention may be obtained from microbes, or produced in vitro or in vivo.

An expression vector optionally includes regulatory sequences operably linked to the coding region. The invention is not limited by the use of any particular promoter, and a wide variety of promoters are known. Promoters act as regulatory signals that bind RNA polymerase in a cell to initiate transcription of a downstream (3' direction) coding region. The promoter used may be a constitutive or an inducible promoter. It may be, but need not be, heterologous with respect to the host cell.

An expression vector may optionally include a ribosome binding site and a start site (e.g., the codon ATG) to initiate translation of the transcribed message to produce the polypeptide. It may also include a termination sequence to end translation. A termination sequence is typically a codon for which there exists no corresponding aminoacetyl-tRNA, thus ending polypeptide synthesis. The polynucleotide used to transform the host cell may optionally further include a transcription termination sequence.

A vector introduced into a host cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Examples of a marker sequence are sequences that confer resistance to kanamycin, ampicillin, chloramphenicol, tetracycline, and neomycin.

Polypeptides and fragments thereof useful in the present invention may be produced using recombinant DNA techniques, such as an expression vector present in a cell. Such methods are routine and known in the art. The polypeptides and fragments thereof may also be synthesized in vitro, e.g., by solid phase peptide synthetic methods. The solid phase peptide synthetic methods are routine and known in the art. A polypeptide produced using recombinant techniques or by solid phase peptide synthetic methods may be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity.

The present invention also includes antibodies that specifically bind a polypeptide of the present invention. An antibody that specifically binds an Acs polypeptide of the present invention, preferably, SEQ ID NO:4 or a fragment thereof, does not bind to a polypeptide having the amino acid sequence described at SEQ ID NO:13. An antibody that specifically binds a WS polypeptide of the present invention, preferably, SEQ ID NO: 2 or a fragment thereof, does not bind to the polypeptide having the amino acid sequence described at SEQ ID NO:8.

Antibody may be produced using a polypeptide of the present invention, or a fragment thereof. The antibody may be polyclonal or monoclonal. Laboratory methods for producing, characterizing, and optionally isolating polyclonal and monoclonal antibodies are known in the art (see, for instance, Harlow E. et al. *Antibodies: A laboratory manual* Cold Spring Harbor Laboratory Press, Cold Spring Harbor (1988). For instance, a polypeptide of the present invention may be administered to an animal, preferably a mammal, in an amount effective to cause the production of antibody specific for the administered polypeptide. Optionally, a polypeptide may be mixed with an adjuvant, for instance Freund's incomplete adjuvant, to stimulate the production of antibodies upon administration. Whether an antibody of the present invention specifically binds to a polypeptide of the present invention may be determined using methods known in the art. For instance, specificity may be determined by testing antibody binding to SEQ ID NO:2 and the amino acid sequence SEQ ID NO:8. Other examples include testing the kinetics of antibody binding to different polypeptides, and testing competition in binding using as competitors known polypeptides containing or not containing an epitope against which the antibody is directed.

The present invention also includes genetically modified microbes that have a polynucleotide encoding a WS polypeptide of the present invention, an Acs polypeptide of the present invention, or a combination thereof. Compared to a control microbe that is not genetically modified according to the present invention, a genetically modified microbe may exhibit production of a WS polypeptide of the present invention or a fragment thereof, production of an Acs polypeptide of the present invention or a fragment thereof, or the combination thereof. A polynucleotide encoding a WS polypeptide of the present invention, an Acs polypeptide of the present invention, or a combination thereof, may be present in the microbe as a vector or integrated into a chromosome.

Examples of eukaryotic cells include, but are not limited to, *Pichia* (such as *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica*), *Saccharomyces* (such as *Saccharomyces cerevisiae, Hansenula polymorpha, Kluyveromyces* (such as *Kluyveromyces lactis*), *Candida albicans, Aspergillus* (such as *Aspergillus nidulans, Aspergillus niger, Aspergillus oryzae*), *Trichoderma reesei, Chrysosporium lucknowense, Fusarium* (such as *Fusarium gramineum, Fusarium venenatum*), *Neurospora crassa, Yarrowia lipolyticum*, and *Chlamydomonas reinhardtii*, and the like.

Examples of bacteria include, but are not limited to, *Acinetobacter* (such as *Acinetobacter baylyi*), *Agrobacterium, Alicyclobacillus, Anabaena, Anacystis, Arthrobacter, Azobacter, Bacillus* (such as *Bacillus subtilis, Bacillus amyloliquefacines*), *Brevibacterium* (such as *Brevibacterium ammoniagenes, Brevibacterium immariophilum*), *Chromatium, Clostridium* (such as *Clostridium beigerinckii*), *Corynebacterium, Enterobacter* (such as *Enterobacter sakazakii*), *Erwinia, Escherichia* (such as *Escherichia coli*), *Lactobacillus, Lactococcus* (such as *Lactococcus lactis*), *Mesorhizobium* (such as *Mesorhizobium loti*), *Methylobacterium, Microbacterium, Phormidium, Pseudomonas* (such as *Pseudomonas aeruginosa, Pseudomonas citronellolis,*

*Pseudomonas mevalonii, Pseudomonas pudica*), *Rhodobacter* (such as *Rhodobacter capsulatus, Rhodobacter sphaeroides*), *Rhodopseudomonas, Rhodospirillum* (such as *Rhodospirillum rubrum*), *Rhodococcus, Salmonella* (such as *Salmonella enterica, Salmonella typhi, Salmonella typhimurium*), *Scenedesmun, Serratia, Shigella* (such as *Shigella dysenteriae, Shigella flexneri, Shigella sonnei*), *Staphylococcus* (such as *Staphylococcus aureus*), *Streptomyces, Synnecoccus, Zymomonas*, and the like.

Examples of archaea include, but are not limited to *Aeropyrum* (such as *Aeropyrum pernix*), *Archaeglobus* (such as *Archaeoglobus fulgidus*), *Halobacterium, Methanococcus* (such as *Methanococcus jannaschii*), *Methanobacterium* (such as *Methanobacterium thermoautotrophicum*), *Pyrococcus* (such as *Pyrococcus abyssi, Pyrococcus horikoshii*), *Sulfolobus*, and *Thermoplasma* (such as *Thermoplasma acidophilum, Thermoplasma volcanium*), and the like.

A genetically modified microbe of the present invention may include other modifications in addition to a polynucleotide encoding a WS polynucleotide of the present invention or a fragment thereof, an Acs polynucleotide of the present invention or a fragment thereof, or a combination thereof. Such modifications may provide for increased production of substrates used by a WS polypeptide of the present invention or an Acs polypeptide of the present invention. For instance, modifications may provide for increased levels in a cell of isoprenoids, fatty acids, alcohols (including, for instance, ethanol, fatty alcohols, and isoprenoid alcohols), Coenzyme A (CoA), and acyl-CoA. Modifications may provide for increased levels substrates by, for instance, increasing production of enzymes in biosynthetic pathways, reducing feedback inhibition at different locations in biosynthetic pathways, increasing importation of substrates and/or compounds used in biosynthetic pathways to make substrates, decreasing catabolism of substrates and/or compounds used in biosynthetic pathways to make substrates.

Preferably, a genetically modified microbe produces high levels of substrates needed for biodiesel production, for example high levels of ethanol and/or acyl-CoA. Biodiesel refers to fatty acid alkyl esters of long-chain fatty acids with short-chain alcohols. The long-chain fatty acid may be at least $C_8$. For example, the long-chain fatty acid may be at least $C_8$, at least $C_{10}$, at least $C_{12}$, or at least $C_{14}$, and no greater than $C_{16}$, no greater than $C_{18}$, no greater than $C_{20}$, or no greater than $C_{22}$. Such long-chain fatty acids may be saturated or unsaturated, and may be branched or unbranched. The short-chain alcohol may be from, for instance, at least $C_1$, at least $C_2$, at least $C_3$, at least $C_4$, at least $C_5$, or at least $C_6$. Preferably, the alcohol is $C_1$ or $C_2$, more preferably, $C_2$.

Methods for modifying microbes to increase these and other compounds are routine and known in the art (Keasling et al., WO07/136,762, and Keasling et al., US Published Patent Application 20080171378). For instance, isoprenoids in a genetically modified microbe of the present invention may be increased by, for instance, increasing production of one or more mevalonate pathway enzymes, increasing production of one or more non-mevalonate pathway enzymes, increasing production of prenyl transferase, and/or decreasing production of squalene synthase. Fatty acids in a genetically modified microbe of the present invention may be increased by, for instance, increasing production of fatty acid synthases, increasing production of thioesterases, increasing production of acyl carrier protein, and increasing production of malonyl-CoA. A genetically modified microbe of the present invention may also include modifications that provide fatty acids of various lengths. Fatty alcohols in a genetically modified microbe of the present invention may be increased by, for instance, the use of a fatty acyl-CoA reductase (Kalscheuer et al., Appl. Environ. Microbiol., 2006, 72:1373-1379). Creating a larger pool of acyl-CoA substrates from glucose using the acetyl-CoA carboxylase (Acc1) may allow larger amounts of fatty acid ethyl esters to be produced solely from glucose.

A genetically modified microbe of the present invention may include other modifications that provide for increased ability to use renewable resources, such as lignocellulosic biomass, as an energy source. Such modifications may provide for increased production of enzymes useful in the breakdown of lignocellulosic materials, such as hydrolytic enzymes, saccharolytic enzymes, and/or pectinolytic enzymes. Other modifications include those that provide for export of an ester or a CoA-activated compound out of a genetically modified microbe.

One advance of the present invention relates to methods for the production of biodiesel compounds from renewable resources. Biodiesel compounds are typically produced by transesterification of triglycerides, but significant levels of triacylglycerols are also produced and must be separated from the biodiesel prior to its use as a fuel. The present invention includes the advantage of producing biodiesel compounds from renewable resources with little to no production of contaminating triacylglycerols. There is significant demand for alternative fuels, and the present invention may help to meet that demand. Another advance of the present invention relates to methods for the production of wax esters with low production of contaminating triacylglycerols. There is strong demand for large-scale production of wax esters, such as jojoba-like wax esters, which have multiple commercial uses. By variation of the substrates used by the polypeptides of the present invention, one may vary the composition of the esters produced. The invention provides the basis, for example, for microbial biotechnological production of biodiesel compounds, and wax esters, including jojoba-like wax esters.

In one aspect, the methods of the present invention may include providing a genetically modified microbe that contains an Acs polynucleotide of the present invention and expresses an Acs polpeptide or a fragment thereof, and incubating the microbe under conditions suitable for the production of CoA-activated compound, such as CoA-activated fatty acids and CoA-activated isoprenoids. In another aspect, the methods may include providing a genetically modified microbe that contains a WS polynucleotide of the present invention and expresses a WS polypeptide or a fragment thereof, and incubating the microbe under conditions suitable for the production of an ester. Optionally, a cell useful in this aspect includes an Acs polynucleotide, preferably an Acs polynucleotide of the present invention. Optionally, a CoA-activated compound or ester may be isolated, preferably purified. Separation of CoA-activated compounds and esters may be readily achieved by routine methods known in the art.

One of skill in the art will understand that an ester produced by a WS polypeptide of the present invention includes an A side and a B side. As described herein, the A side includes, for instance, a fatty acid-derived group or an isoprenoid-derived group. The A side may result from the use of a CoA-activated compound as the substrate. Preferably, the CoA-activated compound is a CoA-activated fatty acid or a CoA-activated isoprenoid, preferably catalyzed by an Acs polypeptide of the present invention. The fatty acid or isoprenoid used to produce the CoA-activated fatty acid or a CoA-activated isoprenoid may be produced de novo by the microbe or imported. As described herein, the B side includes, for instance, an alcohol-derived group. The B side may result from the use of an alcohol. Thus, one of skill in the art will appreciate that a variety of esters may be produced using the methods of the present invention by varying the substrates used by a WS polypeptide for the A side and the B side of the resulting ester. It is expected that any combination of CoA-activated compound and alcohol may be used by a WS polypeptide of the present invention. Accordingly, the A side of an ester produced by the methods may be derived from, for instance, a fatty acid with a chain length of at least $C_2$ to no greater than $C_{22}$ as described above, preferably at least $C_{12}$ to no greater than $C_{22}$, that is saturated or unsaturated and linear or branched, or an isoprenoid with a chain length of at least $C_5$ to no greater than $C_{20}$ as described above, preferably at least $C_{15}$ to no greater than $C_{20}$, that is saturated or unsaturated and linear or cyclic. Likewise, the B side may be an alcohol of at least $C_1$ to no greater than $C_{22}$.

Preferred examples of esters made using the methods described herein useful as biodiesels include, but are not limited to, ethyl oleate ($C_{18:1}$-ethyl ester) and ethyl palmitate ($C_{16}$-ethyl ester). Preferred examples of esters made using the methods described herein useful as waxes include, but are not limited to, palmityl oleate, $C_{32:1}$, $C_{34:1}$, and $C_{36:2}$ wax esters (see, for instance, Klascheuer et al., 2006, Appl. Env. Microbiol. 72:1373-1379).

In some aspects, a genetically modified microbe exhibits an increase in ester or CoA-activated compound production, where ester or CoA-activated compound production is increased by at least 5%, at least 10%, at least 15%, at least 20%, at least 25%, at least 30%, at least 35%, at least 40%, at least 45%, at least 50%, at least 60%, at least 70%, at least 80%, at least 90%, at least 2-fold, at least 2.5-fold, at least 5-fold, at least 10-fold, at least 20-fold, at least 30-fold, at least 40-fold, at least 50-fold, at least 75-fold, at least 100-fold, at least 200-fold, at least 300-fold, at least 400-fold, at least 500-fold, or at least $10^3$-fold, or more, in the genetically modified microbe, compared to the level of ester or CoA-activated compound produced in a control microbe that is not genetically modified as described herein. Ester or CoA-activated compound production is readily determined using well-known methods, e.g., gas chromatography-mass spectrometry, liquid chromatography-mass spectrometry, ion chromatography-mass spectrometry, pulsed amperometric detection, UV/VIS spectroscopy, and the like.

In some aspects, a genetically modified microbe provides for increased production of ester or CoA-activated compound per cell, e.g., the amount of ester or CoA-activated compound produced is at least 5%, at least 10%, at least 15%, at least 20%, at least 25%, at least 30%, at least 35%, at least 40%, at least 45%, at least 50%, at least 60%, at least 70%, at least 80%, at least 90%, at least 2-fold, at least 2.5-fold, at least 5-fold, at least 10-fold, at least 20-fold, at least 30-fold, at least 40-fold, at least 50-fold, at least 75-fold, at least 100-fold, at least 200-fold, at least 300-fold, at least 400-fold, or at least 500-fold, or $10^3$-fold, or more, higher than the amount of the ester or CoA-activated compound produced by a control microbe that is not genetically modified as described herein. Amount of cells may be measured by measuring dry cell weight or measuring optical density of the cell culture.

In other aspects, a genetically modified microbe provides for increased production of ester or CoA-activated compound per unit volume of cell culture, e.g., the amount of ester or CoA-activated compound produced using a genetically modified microbe is at least 5%, at least 10%, at least 15%, at least 20%, at least 25%, at least 30%, at least 35%, at least 40%, at least 45%, at least 50%, at least 60%, at least 70%, at least 80%, at least 90%, at least 2-fold, at least 2.5-fold, at least 5-fold, at least 10-fold, at least 20-fold, at least 30-fold, at least 40-fold, at least 50-fold, at least 75-fold, at least 100-fold, at least 200-fold, at least 300-fold, at least 400-fold, or at least 500-fold, or $10^3$-fold, or more, higher than the amount of the ester or CoA-activated compound produced by a control microbe that is not genetically modified as described herein, on a per unit volume of cell culture basis.

In general, a genetically modified microbe is cultured in a suitable medium. Which medium is suitable depends on the genetically modified microbe used, and such media are routine and known in the art. In some aspects, a genetically modified microbe is cultured in a suitable medium, and the culture medium is overlaid with an organic solvent forming an organic layer. The ester or CoA-activated compound produced by the genetically modified microbe may partition into the organic layer, from which it may be isolated. In some aspects, where one or more coding region is operably linked to an inducible promoter, an inducer may be added to the culture medium and, after a suitable time, the ester or CoA-activated compound may be isolated from the organic layer overlaid on the culture medium or from the genetically modified microbe if the ester or CoA-activated compound is not exported from the cell.

The present invention provides compositions that include a genetically modified microbe. A composition may include components in addition to the genetically modified microbe, which components are selected based in part on the intended use of the genetically modified microbe. Suitable components include, but are not limited to, salts; buffers; stabilizers; protease-inhibiting agents; hydrolytic enzymes, saccharolytic enzymes, pectinolytic enzymes; cell membrane- and/or cell wall-preserving compounds, e.g., glycerol, dimethylsulfoxide, etc.; nutritional media appropriate to the cell; and the like.

The present invention also provides compositions that include CoA-activated compounds or esters. A preferred example of a composition includes biodiesel, where the composition includes less of the impurities typically present in biodiesel produced using chemical processing methods such as the transesterification of triglycerides. Such impurities include glycerol byproducts such as triacylglycerols. Preferably, the composition includes less than 0.05%, less than 0.1%, less than 0.5%, less than 1.0% of glycerol byproducts, preferably triacylglycerols.

The present invention is illustrated by the following examples. It is to be understood that the particular examples, materials, amounts, and procedures are to be interpreted broadly in accordance with the scope and spirit of the invention as set forth herein.

EXAMPLES

Example 1

Biosynthesis of Isoprenoid Wax Ester in *Marinobacter hydrocarbonoclasticus* DSM 8798: Identification and Characterization of Isoprenoid Coenzyme A Synthetase and Wax Ester Synthases

*Marinobacter hydrocarbonoclasticus* DSM 8798 has been reported to synthesize isoprenoid wax ester storage compounds when grown on phytol as the sole carbon source under limiting nitrogen and/or phosphorous conditions. We hypothesized that isoprenoid wax ester synthesis involves (i) activation of an isoprenoid fatty acid by a coenzyme A (CoA) synthetase and (ii) ester bond formation between an isoprenoid alcohol and isoprenoyl-CoA catalyzed, most likely, by an isoprenoid wax ester synthase similar to an acyl wax ester synthase, wax ester synthase/diacylglycerol acyltransferase (WS/DGAT), recently described from *Acinetobacter* sp. strain ADP1. We used the recently released rough draft genome sequence of a closely related strain, *M. aquaeolei* VT8, to search for WS/DGAT and acyl-CoA synthetase candidate genes. The sequence information from putative WS/DGAT and acyl-CoA synthetase genes identified in this strain was used to clone homologues from the isoprenoid wax ester synthesizing *Marinobacter* strain. The activities of the recombinant enzymes were characterized, and two new isoprenoid wax ester synthases capable of synthesizing isoprenoid ester and acyl/isoprenoid hybrid ester in vitro were identified along with an isoprenoid-specific CoA synthetase. One of the *Marinobacter* wax ester synthases displays several orders of magnitude higher activity toward acyl substrates than any previously characterized acyl-WS and may reflect adaptations to available carbon sources in their environments.

The enzymes involved in isoprenoid WE synthesis, however, are not known. We hypothesized that isoprenoid WE synthesis would, as in acyl WE synthesis, involve the condensation of a CoA-activated isoprenoid acid with an isoprenoid alcohol. Based on this hypothesis, we describe here the isolation and characterization of an isoprenoid CoA-synthetase, as well as of two isoprenoid WE synthetases from strain 8798 (Gauthier et al., 1992. Int. J. Syst. Bacteriol. 42:568-576) that are capable of producing an isoprenoid wax from phytanoyl-CoA and phytol.

Materials and Methods

Chemicals and Materials.

CoA trilithium salts were purchased from Roche (Indianapolis, Ind.). Tris (2-carboxyethyl) phosphine (TCEP) was purchased from EMB Biosciences (La Jolla, Calif.). Phytanic acid, palmitoyl-CoA ($C_{16:0}$), stearoyl-CoA ($C_{18:0}$), arachidoyl-CoA ($C_{20:0}$), $C_{18}$ linolenoyl-CoA ($C_{18:3}$), myristoyl-CoA ($C_{14:0}$), lauroyl ($C_{12:0}$) and 5,5'-dithio-bis(2-nitrobenzoic acid) (DNTB), inorganic pyrophosphatase, Triton X-100, triolein, and ATP were purchased from Sigma (St. Louis, Mo.). Tergitol NP-11 was obtained from Dow Chemical Co. (Midland, Mich.). Gum arabic, sodium taurocholate, and all solvents (high-pressure liquid chromatography [HPLC] grade) were purchased from Fisher Scientific (Pittsburgh, Pa.). HPLC-grade water was purchased from Mallinckrodt Chemicals (Phillipsburg, N.J.). Restriction endonucleases, polynucleotide kinase, and T4 ligase were purchased from New England Biolabs (Boston, Mass.).

Strains and Growth Conditions.

*Marinobacter hydrocarbonoclasticus* strain DSM 8798 was obtained from the German Collection of Microorganisms and Cell Cultures (DSMZ). *Acinetobacter baylyi* ADP1 was kindly provided to us by Nicholas Ornston at Yale University (New Haven, Conn.). *Pseudomonas putida* strain U was kindly given to us by José M. Luengo at the University of Léon (Léon, Spain). Cloning and heterologous gene expression was carried out in *Escherichia coli* strains DH5α and JM109. *M. hydrocarbonoclasticus* DSM 8798 was grown in Luria-Bertani (LB) medium with sterile, synthetic seawater (Ricca Chemical Company, Arlington, Tex.) instead of distilled water. *E. coli, A. baylyi*, and *P. putida* were grown in LB medium at 30° C. unless otherwise specified.

Gene Cloning.

Genomic DNA was isolated from *A. baylyi* ADP1, *M. hydrocarbonoclasticus* DSM 8798, and *P. putida* U using standard phenol-chloroform DNA extraction techniques described in Sambrook et al. (Sambrook et al., 1989. Molecular cloning: a laboratory manual, 2nd ed. Cold Spring Harbor Laboratory, Cold Spring Harbor, N.Y.). Degenerate rRNA oligonucleotides (TPU1, 5'-AGAGTTTGATCMTGGCT-CAG (SEQ ID NO:19); RTU8,5'-AAGGAGGTGATCCAN-CCRCA (SEQ ID NO:20) [Funke et al., 2004. J. Clin. Microbiol. 42:3366-3368]) were used to amplify the 16S rRNA gene sequences from *M. hydrocarbonoclasticus* DSM 8798 (referred to as strain 8798). Gene-specific oligonucleotides for cloning of genes from strain 8798 were designed based on gene sequences identified in the rough-draft genome annotation of *Marinobacter aquaeolei* strain VT8 released by the DOE Joint Genome Institute (available on the world wide web at jgi.doe.gov).

Cloning and DNA manipulations were carried out in *E. coli* DH5α using the standard molecular biology techniques described by Sambrook et al. (1989. Molecular cloning: a laboratory manual, 2nd ed. Cold Spring Harbor Laboratory, Cold Spring Harbor, N.Y.). Genes encoding WS1, WS2, WS3, Acs1, Acs2, Acs3, and Acs4 were PCR amplified from strain 8798 genomic DNA by using gene-specific oligonucleotides that introduce XbaI and NotI restriction sites. The XbaI/NotI-digested inserts were ligated into plasmid pUC-mod for constitutive expression from a modified lac promoter (Schmidt-Dannert et al., 2000. Nat. Biotechnol. 18:750-753). Histidine tags were added to the isolated genes: putative acyl-CoA synthetase genes contain a C-terminal His6 tag, and WS genes have an N-terminal His6 tag. Cloned gene sequences were verified by sequencing. The stop codon in the WS4 sequence was verified by sequencing several clones and also the PCR amplification product.

Protein Expression and Purification.

Cultures (100 ml) of *E. coli* JM109 transformed with pUC-mod expressing putative His6-tagged CoA synthetases or WSs were grown in LB media supplemented with 100 μg of ampicillin/ml at 30° C. overnight in 500-ml unbaffled flasks. Cells were harvested by centrifugation and resuspended in 10 ml of 50 mM Tris-HCl buffer (pH 8) for CoA synthetase enzymes and in 125 mM sodium phosphate buffer (pH 7.4) for WS enzymes. The cells were lysed by sonication (Branson, Danbury, Conn.) on ice using a 30% duty cycle consisting of 10 s on and 30 s off for 10 cycles. Cell lysates were spun down at a centrifugal force of 13,763×g in 50-ml Oakridge tubes in a Beckman J2-HS floor centrifuge equipped with a JA-17 rotor for 30 min at 4° C. The supernatant was applied to immobilized metal affinity chromatography using Talon resin (Clontech, Mountain View, Calif.) and washed with 10 mM imidazole in 50 mM Tris-HCl buffer (pH 8) or 125 mM sodium phosphate buffer (pH 7.4). The purified proteins were eluted with 300 mM imidazole in either 50 mM Tris-HCl buffer (pH 8) or 125 mM sodium phosphate buffer (pH 7.4). Elutants were desalted with (Amersham, Piscataway, N.J.) PD-10 resin columns to remove excess imidazole. The purified proteins were concentrated to 1 ml using Vivaspin (Vivascience, Hannover, Germany) 10,000-Da columns. Protein concentrations were determined by using the bicinchoninic acid protein assay method with bovine serum albumin as a protein standard (Pierce Biotechnology, Inc., Rockford, Ill.).

CoA Synthetase Assay.

In vitro reactions were performed as described previously (Trivedi et al., 2004, Nature, 428:441-445) with some modifications. CoA synthetase assays were carried out in 250-μl reaction volumes containing 50 mM Tris-HCl buffer (pH 7.5), 0.1% Triton X-100, 10 mM MgCl2, 5 mM TCEP, 0.1 U of inorganic pyrophosphatase, and as substrates 10 mM phytanic or fatty acids, 10 mM reduced coenzyme A (CoASH), 10 mM ATP, and 0.5 μg of purified Acs (either 1, 2, 3, or 4) protein. The reactions were incubated for 20 min at 37° C. and stopped with 25 µl of 5% acetic acid, followed by HPLC analysis of the reaction products.

HPLC and LC/ESI-MS Analysis of CoA Synthetase Reactions.

CoA-synthetase assay samples (25 µl) were resolved on an Agilent 1100 HPLC (Agilent Technologies, Palo Alto, Calif.) equipped with a photodiode array detector set to 259 nm. Samples were separated on a reversed-phase Eclipse XDB-C8 column (Agilent Technologies) at a flow rate of 1 ml min$^{-1}$. Solvent A consisted of 20 mM ammonium acetate (pH 5.4) in HPLC-grade water, and solvent B contained acetonitrile and methanol (85:15 [vol/vol]). Acyl-CoA and phytanoyl-CoA products were eluted using the following conditions: solvent A-solvent B at 65:35 from 0 to 5 min, followed by a gradient from solvent A-solvent B at 65:35 to 100% solvent B in 30 min. Liquid chromatography-mass spectrometry (LC-MS) analyses of reaction products were done with an LCQ mass spectrophotometer equipped with an electrospray ionization source (ESI) (Thermo Finnigan). Mass fragmentation spectra were monitored in a mass range of m/z 400 to 1,500 with a negative ESI interface.

Preparation of Phytanoyl-CoA.

Commercially unavailable phytanoyl-CoA for WS assays was synthesized enzymatically with Acs2 under the CoA synthetase assay conditions described above with phytanic acid as the substrate. Enzymatically derived phytanoyl-CoA was purified by preparative HPLC: 100 µl in vitro reaction samples were separated under essentially the same conditions described above for the HPLC analysis of CoA products. Phytanoyl-CoA fractions were collected and dried under nitrogen gas. Phytanoyl-CoA was quantified by comparison to UV/visual (UV/Vis) spectra of lauroyl-CoA, assuming comparable extinction coefficients of the CoA chromophores in phytanoyl- and lauroyl-CoA.

Profiling of WS Substrate Ranges Using a Coupled Enzyme Assay.

Stock solutions of various substrates were prepared in 50 mM Tris-HCl buffer (pH 8) containing 1% gum arabic, 12.5 µg bovine serum albumin ml$^{-1}$, 0.1% taurocholate, and either 100 mM fatty acid, isoprenoid acid, fatty alcohol, or isoprenoid alcohol. Stock solutions were sonicated to disperse the substrates. Substrate profiles of the three WS were tested using coupled enzyme in vitro reactions in which the CoA synthetases Acs1 and Acs2 are added to synthesize the CoA-activated fatty acid phytanic acid substrates from corresponding acid precursors for the WS reactions. Assays were carried out in 500-µl reactions containing in 50 mM Tris-HCl buffer (pH 8.0), 12.5 µl of each acid, and alcohol substrate stock solution (final concentrations of each substrate of 250 µM), 10 mM MgCl2, 10 mM CoASH, 10 mM ATP, 5 mM TCEP, 0.1 U of inorganic pyrophosphatase, 0.25 µg of Acs1 and Acs2 CoA synthetase, and 0.5 µg of WS to be tested. Assays were incubated at 37° C. overnight before thin-layer chromatography (TLC) analysis of the reaction products.

TLC.

In vitro WS assay samples were extracted with 500 µl of chloroform:methanol (1:1 [vol/vol]), and extracts were analyzed by TLC with Whatman normal phase silica gel 60 plates and developed using hexane-diethyl ether-acetic acid (90:10:1 [vol/vol/vol]). TLC plates were stained with either iodine vapor or anisaldehyde solution as described earlier (Jork et al., 1990. Thin-layer chromatography reagents and detection methods, vol. 1a. Physical and chemical detection methods: fundamentals, reagents. VHC, Weinheim, Germany). Palmitoyl palmitate and triolein were used as WE and TAG reference compounds, respectively.

DGAT Assay.

The DGAT activity of WS enzymes was measured using the coupled WS enzyme assay conditions described above with oleic acid as acyl donor and 1,2 dipalmitoyl-sn glycerol as the acyl acceptor (final concentration of each substrate of 250 µM) and 0.25 µg of Acs2 isoprenoid/acyl-CoA synthetase to generate CoA activated oleic acid.

GC-MS analysis of WE.

GC electron impact MS analyses were performed with a Hewlett-Packard 6890 series gas chromatograph connected to an HP 5973 mass spectrometer. GC conditions consisted of a column (30 m by 0.25 mm [inner diameter] by 1.5 µm coated with 5% phenylmethyl silicone) with the injector temperature set to 250° C. The oven was set to a temperature gradient of 30° C. min$^{-1}$ from 60 to 130° C., followed by slowing of the gradient from 130 to 300° C. at 4° C. min$^{-1}$ using helium as a carrier gas. The MS conditions used an electron energy of 70 eV and a source temperature set to 170° C. Mass spectra were scanned in a range of m/z 40 to 600 at 1-s intervals.

Kinetic WS Assay.

WS activity was determined by monitoring CoA release using Ellman's reagent [5,5'-dithio-bis(2-nitrobenzoic acid); DTNB] at 412 nm ($\epsilon$=13,600 M$^{-1}$ cm$^{-1}$) (Ellman, 1959. Arch. Biochem. Biophys. 82:70-77). Kinetic in vitro assays were performed in triplicate in 125 mM sodium phosphate buffer (pH 7.4) containing 0.1% Tergitol NP-11 detergent, 10 mM MgCl2, 1 mM DNTB, 250 µM palmitoyl-CoA, 1 to 250 µM hexadecanol, and 0.5 µg of WS enzyme. Assay reactions were preincubated at 37° C. for 5 min before the reactions were started by the addition of enzyme. Heat-denatured enzyme (99° C. for 15 min) was used as a negative control.

Measurement of Acyl-CoA and Fatty/Isoprenoid Alcohol Specificity.

Acyl-CoA and fatty/isoprenoid alcohol specificity of WS2 was determined in the same manner as described for the kinetic WS assay with assumed saturating conditions containing both the fatty/isoprenoid alcohol and acyl-CoA substrates at a concentration of 1 mM. Acyl-CoA specificity was measured with hexadecanol as acyl acceptor, whereas palmitoyl-CoA was used as acyl donor to determine alcohol specificity. Isoprenoid WS activity of WS2 was determined with 250 µM HPLC purified phytanoyl-CoA and 250 µM phytol as substrates.

Results

Identification and Cloning of Putative Isoprenoid WE Biosynthetic Genes.

*M. hydrocarbonoclasticus* DSM 8798 (strain 8798) was shown previously to synthesize isoprenoid WE from phytol. Based on the recent characterization of a fatty acid WS (WS/DGAT) from *Acinetobacter baylyi* ADP1 that condenses a CoA activated fatty acid and a fatty alcohol to make fatty acid WE storage compounds, we reasoned that isoprenoid WE synthesis may follow a similar pathway with an isoprenoid specific acyl-CoA synthetase and WS as key enzymes (FIG. 1). Because no sequence information is available for strain 8798, we used a recent draft genome sequence (released by the DOE Joint Genome Institute [available on the world wide web at the DOE Joint Genome Institute website] in October 2005) of the alkane hydrocarbon metabolizing *M. aquaeolei* VT8 strain (Huu et al., 1999. Int. J. Syst. Bacteriol. 49:367-375; Marquez and Ventosa. 2005. Int. J. Syst. Evol. Microbiol. 55:1349-1351) (referred to as strain VT8 below) for the identification and cloning of isoprenoid WE biosynthetic genes in strain 8798. Sequence analysis of the 16S rRNA gene of strain 8798 showed it to be 99.4% identical to that of strain VT8, suggesting a high degree of genomic conservation between the two strains.

A BLAST homology search of the draft VT8 genome sequence (released in October 2005) using the known WS/DGAT amino acid sequence from *A. baylyi* ADP1 identified four putative WS homologues (WS1, -2, -3, and -4) (Table 1 and FIG. 2). Two of the homologues, WS1 and WS2, were located in two putative alkane degradation gene clusters that share some sequence similarity with a known alkane degradation cluster described from *P. oleovorans* (van Beilen et al., 1992. Mol. Microbiol. 6:3121-3136). However, while the present study was under review, the sequence of *Marinobacter aquaeolei* VT8 genome was reassembled, and a final draft of the genome sequence was released 28 Dec. 2006. In the previous annotation, WS1 was associated with gene cluster 1, which is no longer the case in the new genome assembly. Now, WS1 is located approximately 250 kb upstream of this cluster (FIG. 3, which maintains the gene organization in the first genome assembly but now also shows the new gene localizations). WS1 and alkane gene cluster 1 are each flanked by inverted transposase sequences (of which there are three 100% conserved copies in the genome), resulting in a contiguous assembly in the first draft. Similarly, we hypothesized that WS2 was also associated with an alkane degradation operon (FIG. 3, gene cluster 2) since both were located near a physical sequence gap. This gap has now been closed, and WS2 is not associated with any alkane degradation gene cluster. If the current genome sequence is correct, none of the WS homologues are clustered any longer with any obvious alkaneutilizing metabolic operons.

ing of the homologues from strain 8798. PCR products were obtained for Acs1 to -4 and WS1 to -4 ORFs and cloned into pUCmod for sequencing. The putative acyl-CoA synthase of gene cluster 2, for which only a partial sequence was available until very recently (see above), could not be amplified using a C-terminal oligonucleotide derived from the Acs1 sequence. All cloned WS and Acs genes from strain 8798 share a >97% peptide sequence identity with those identified in the genome sequence of strain VT8 (Table 1). The peptide sequence identities of the cloned WS homologues to the experimentally characterized WS/DGAT from *A. baylyi* range from 27 to 45%, with WS4 being the least similar and WS1 having the highest identity (Table 1). However, the cloned WS4 from strain 8798 is a pseudogene with a stop codon that truncates its ORF, whereas the corresponding ORF of WS4 from strain VT8 appears to be intact based on the released draft genome sequence. Acs1 to Acs4 show greater than 50% peptide sequence identity to experimentally characterized medium and long-chain acyl-CoA synthetases from different *Pseudomonas* strains (Table 1).

Identification of *Marinobacter* Isoprenoid CoA Synthetase.

To determine the substrate specificities and to test whether any of the cloned putative acyl-CoA synthetases can catalyze CoA activation of isoprenoid acids, purified recombinant enzymes (Acs1, -2, -3, and -4) were assayed with various saturated fatty acid substrates containing different acyl chain lengths ($C_{10}$, $C_{12}$, $C_{14}$, $C_{16}$, $C_{18}$, and $C_{20}$) and with the isoprenoid phytanic acid. HPLC analysis of the reaction products confirmed Acs1 to be a medium-chain acyl-CoA synthetase that accepts fatty acids with chain lengths ranging from $C_{10}$ to $C_{16}$, while Acs2, -3, and -4 were found to be long-chain acyl-CoA synthetases that act on fatty acids with chain lengths ranging from $C_{12}$ to $C_{20}$ (data not shown). The

TABLE 1

Cloned *M. hydrocarbonoclasticus* DSM 8798 acyl-CoA synthetase and WE synthetases[a]

| Enzyme | Peptide length (amino acids) | GenBank accession no. | ORF no. in strain VT8 (% ID)[b] | Peptide sequence identity to related enzymes | |
|---|---|---|---|---|---|
| | | | | % ID | Strain (source or reference) |
| WS1 | 455 | EF219376 | 168 (99) | 45 | *A. baylyi* ADP1 WS/DGAT (11) |
| WS2 | 473 | EF219377 | 3067 (99) | 38 | *A. baylyi* ADP1 WS/DGAT (11) |
| WS3 | 508 | EF219378 | 851 (99) | 27 | *A. baylyi* ADP1 WS/DGAT (11) |
| WS4 | 349 | EF219379 | 3371 (98) | 25 | *A. baylyi* ADP1 WS/DGAT (11) |
| Acs1 | 544 | EF219372 | 438 (99) | 62 | *P. putida* AlkK (GenBank no. AJ245436) |
| Acs2 | 558 | EF219373 | 1593 (99) | 64 | *P. putida* FadD (13) |
| Acs3 | 555 | EF219374 | 1090 (99) | 55 | *P. aeruginosa* FadD (GenBank no. ABJ10798.1) |
| Acs4 | 560 | EF219375 | 2888 (97) | 51 | *P. aeruginosa* FadD (GenBank no. ABJ10798.1) |

[a]The peptide sequence identities of cloned enzymes to homologues in *M. aquaeolei* strain VT8 and other related enzymes are shown.
[b]Homologous ORFs in *M. aquaeolei* VT8 genome sequence and the percent peptide sequence identity (% ID) to corresponding enzymes clone from *M. hydrocarbonoclasticus* DSM 8798.

Figure 4:
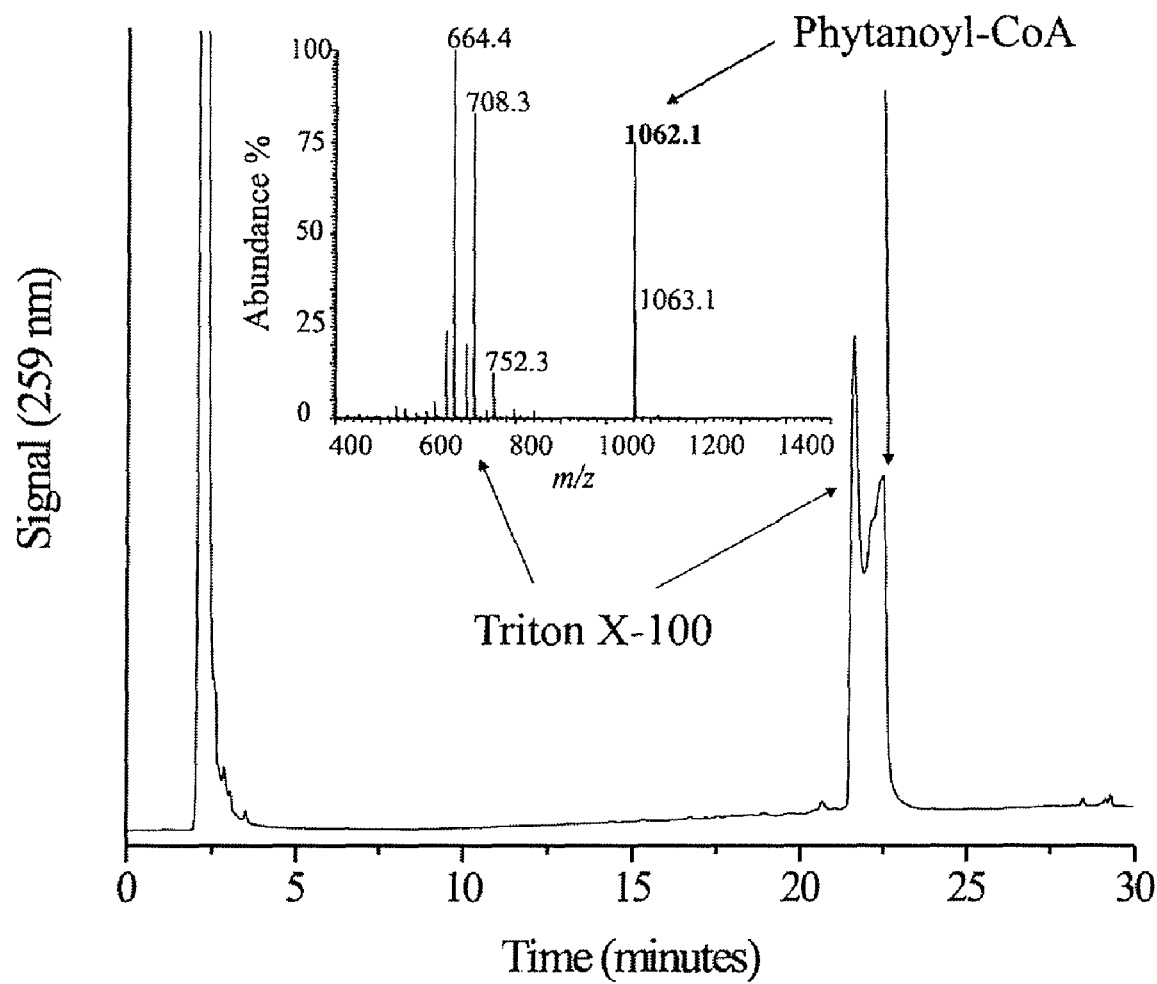
FIG. 4 shows HPLC-MS analysis of Acs2 in vitro reaction with phytanic acid and CoA as substrates. HPLC chromatogram of in vitro reaction showing the phytanoyl-CoA product with a retention time of 22.5 min and the corresponding mass spectrum of the product peak (inset). The observed parent ion (1,062 m/z) is consistent with that of the calculated mass of phytanoyl-CoA. Ions of 664, 708, and 752 m/z correspond to Triton X-100 detergent present in the reaction mixture.

We searched the draft genome sequence for putative acyl-CoA synthetases and identified four open reading frames (ORFs) annotated as medium-chain (Acs1) and long-chain (Acs2, -3, and -4) acyl-CoA synthetases (Table 1). Acs2, -3, and -4 are not clustered with any obvious gene functions. Acs1 is part of one of the putative alkane degradation gene cluster 1 (FIG. 3), previously annotated to also include WS1. Gene cluster 2 contained in the first draft genome sequence a partial acyl-CoA synthetase ORF flanking the physical gap. As stated above, this gap has been closed in the new genome assembly, and this ORF is now annotated as a medium-chain CoA synthetase. Oligonucleotides were designed from the VT8 sequences of the putative WS and Acs genes found in the genome annotation and used for PCR amplification and clonlong-chain acyl-CoA synthetases (Acs2, -3, and -4) showed the most activity when palmitic acid ($C_{16}$) was the substrate. Only Acs2 converted phytanic acid into phytanoyl-CoA, a finding confirmed by LC-MS (FIG. 4). This enzyme, now referred to as isoprenoid/acyl-CoA synthetase, shows 63% peptide sequence identity with a previously described acyl-CoA synthetase (FadD) found in *P. putida* that accepts aromatic alkanoic acids (Marquez and Ventosa. 2005. Int. J. Syst. Evol. Microbiol. 55:1349-1351). The broad substrate range of FadD prompted us to investigate whether this enzyme would also accept phytanic acid. We cloned FadD and assayed the purified recombinant protein with phytanic acid. However, unlike the *Marinobacter* enzyme, FadD does not synthesize phytanoyl-CoA (data not shown).

Substrate Profiles of *Marinobacter* WSs.

Figure 5:
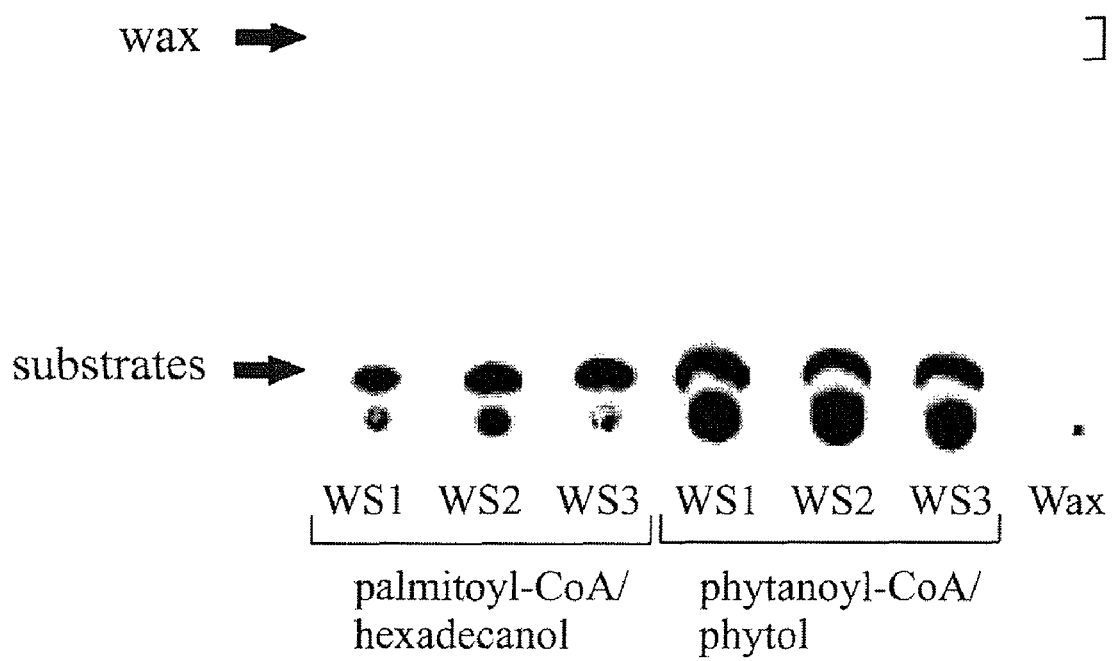
FIG. 5 shows a TLC plate with iodine-stained WE products. TLC analysis of coupled in vitro reactions containing isoprenoid CoA synthetase (Acs2) and WS (WS1, -2, or -3) and either palmitic acid-hexadecanol or phytanic acid-phytol as substrates. A wax standard consisting of palmitoyl palmitate (marked "wax") shows the position of the expected acyl and isoprenoid WE products (marked with an arrow). Products were observed only with WS1 and WS2; no products were observed with WS3.

The activities of the three cloned putative WS with various CoA-activated fatty acids, phytanic acid, and primary alcohols, including the isoprenoid alcohols farnesol and phytol, were investigated by using a coupled enzyme assay. A total of 54 in vitro reactions containing fatty acids and alcohols with various degrees of saturation and carbon chain lengths were arrayed for each WS enzyme. Purified WS proteins and *Marinobacter* CoA synthetases were incubated with CoA and different combinations of acid and alcohol substrates, and product formation was analyzed by TLC. CoA activation of medium-chain fatty acids ($C_{10}$ to $C_{14}$) in these assays was conducted with Acs1, while longchain fatty acids ($C_{16}$ to $C_{20}$) and phytanic acid were esterified with CoA by Acs2. The identification of Acs2 as an isoprenoid/acyl-CoA synthetase made it possible to synthesize commercially unavailable phytanoyl-CoA from available phytanic acid as a substrate for testing with WS1, -2, and -3. Table 2 summarizes WE product formation detected on TLC plates for the tested putative WSs from strain 8798. The TLC substrate profiles show that WS1 and WS2 catalyzed ester bond formation between various activated fatty acids and fatty alcohols or isoprenoid alcohols. FIG. 5 shows representative TLC results for reactions with palmitic acid and hexadecanol and with phytanic acid and phytol. WS2 appears to have a broader substrate range and a higher preference for longerchain fatty alcohols than WS1. WE products derived from short chain acyl-CoA ($C_{10}$ and $C_{12}$) substrates were only detected using the overnight assay conditions. No WE formation was detected using WS3 with any of the substrate combinations tested.

phytanic acid and phytol as substrates. A product peak with a retention time of 41 min and a mass of 590 m/z was detected that was not present in a control using heat-denatured WS2. Its mass and fragmentation pattern match those of the isoprenoid WE previously isolated from strain 8798 by Rontani et al. (Rontani et al., 1999. Appl. Environ. Microbiol. 65:221-230). Together, these results suggest that WS1 and WS2, along with Acs1, are involved in the synthesis of isoprenoid WE storage compounds in *M. hydrocarbonoclasticus* DSM 8798. Because the two *Marinobacter* WSs displayed novel WS activity, the previously described *Acinetobacter* WS/DGAT was also tested but did not show isoprenoid WE formation using phytanic acid and phytol as substrates.

WS/DGAT Activity of *Marinobacter* WSs.

Figure 8:
FIG. 8 shows a diacylglycerol acyltransferase (DGAT) assay of *Marinobacter* DSM 8798 WS1, WS2, and WS3 with oleoyl-CoA as the acyl-donor and dipalmitoyl-glycerol as the acyl acceptor. (O) is an oleic acid standard, (T) is triolein standard and WS1, WS2, and WS3 are in vitro reactions with corresponding enzymes forming TAG reaction products. Only WS1 shows DGAT activity indicated by the formation of a triacylglycerol (TAG) product (arrow).

It has been reported that *Acinetobacter* WS/DGAT has DGAT activity (Kalscheuer and Steinbüchel. 2003. J. Biol. Chem. 278:8075-8082). To test whether any of the three *Marinobacter* WSs can catalyze this reaction, WS1, WS2, and WS3 were tested with oleoyl-CoA as the acyl donor and dipalmitoyl-glycerol as the acyl acceptor, and the products were resolved on TLC plates. TAG products were only detected for WS1, whereas WS2 did not show DGAT activity (FIG. 8).

Kinetic Measurement of WS Activities.

A spectrophotometric assay was developed to determine the kinetic properties of WS1 and WS2. The concentration of sulfhydryl groups of CoA released during the condensation reaction between fatty/isoprenoid CoA activated acids and alcohols was determined by using Ellman's reagent (DTNB)

TABLE 2

Substrate profiles of WS1 and WS2

| | WS profile[a] | | | | | | | | | | | |
|---|---|---|---|---|---|---|---|---|---|---|---|---|
| | WS1 | | | | | | WS2 | | | | | |
| Acid | $C_{10}$ | $C_{12}$ | $C_{14}$ | $C_{16}$ | Phytol | Farnesol | $C_{10}$ | $C_{12}$ | $C_{14}$ | $C_{16}$ | Phytol | Farnesol |
| $C_{20}$ | + | + | + | + | ++ | ++ | − | − | + | + | + | + |
| $C_{18\Delta cis9, 12, 15}$ | − | + | + | − | − | + | + | + | + | + | + | − |
| $C_{18\Delta cis9}$ | + | ++ | +++ | ++ | ++ | ++ | +++ | ++ | +++ | +++ | ++ | ++ |
| $C_{18}$ | ++ | + | ++ | + | ++ | ++ | + | + | + | + | + | ++ |
| $C_{16\Delta cis9}$ | + | ++ | ++ | ++ | +++ | ++ | ++ | ++ | +++ | +++ | ++ | ++ |
| $C_{16}$ | + | ++ | + | +++ | + | ++ | + | + | ++ | +++ | + | ++ |
| $C_{14}$ | − | − | ++ | + | + | ++ | ++ | + | ++ | + | + | ++ |
| $C_{12}$ | − | + | + | + | − | +++ | + | + | + | + | + | ++ |
| $C_{10}$ | + | + | − | + | − | +++ | + | + | − | + | + | + |
| Phytanic acid | − | − | − | − | + | + | − | − | − | − | ++ | ++ |

[a]WE formation was determined by TLC after 12 h at 37° C. for reactions containing different combinations of fatty acids or phytanic acid and fatty alcohols, phytol, or farnesol. The spot intensity of wax ester products on TLC plates was used for qualitative description of WS activities: ranging from no activity (−) to most active (+++).

Figure 6:
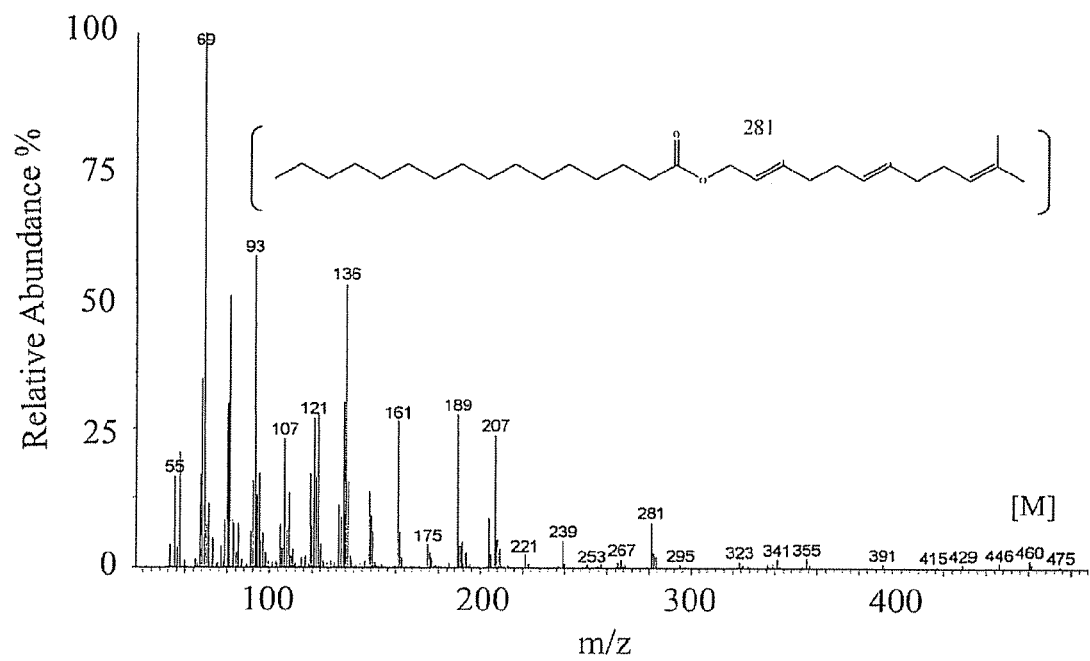
FIG. 6 shows a mass spectrum of an acyl-isoprenoid hybrid wax ester product ([M]=460 m/z) synthesized by WS2 when using palmitoyl-CoA and farnesol as substrates.

WS1 and WS2 also esterified activated fatty acids with isoprenoid alcohols (phytol, farnesol), thereby producing hybrid acyl-isoprenoid WEs (FIG. 6). However, fatty alcohols were not condensed to phytanoyl-CoA by either enzyme. Synthesis of hybrid isoprenoid WE was therefore only possible between an activated fatty acid and an isoprenoid alcohol. Notably, both enzymes produced isoprenoid WEs from phytanoyl-CoA and the isoprenoid alcohols phytol and farnesol, although WS2 was considerably more active with these substrates.

Figure 7:
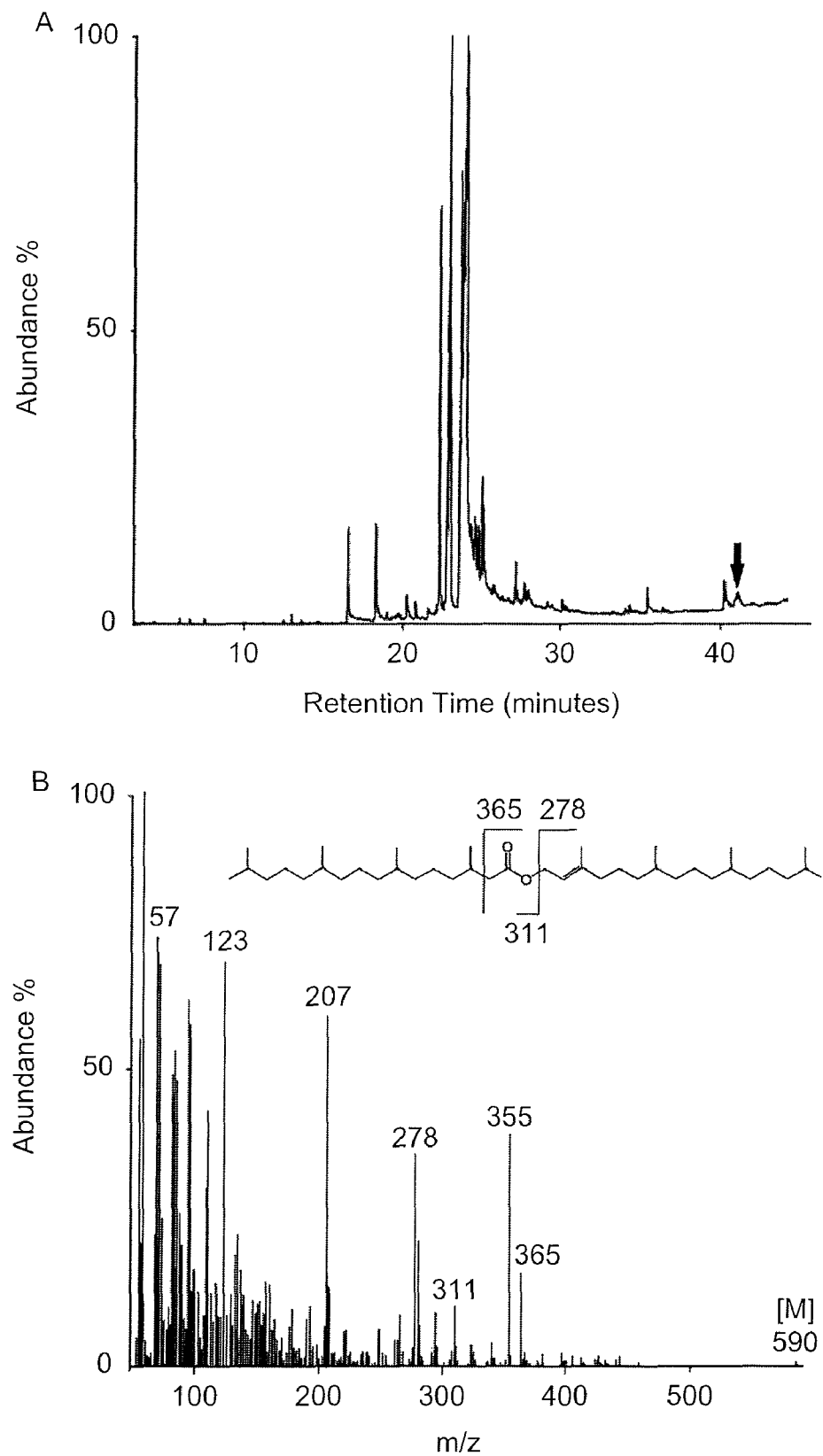
FIG. 7 shows a GC-MS analysis of isoprenoid WE product synthesized in a coupled enzyme reaction with isoprenoid CoA-synthetase Acs2 and WS2 containing phytanic acid and phytol as substrates. (A) Total ion chromatogram showing isoprenoid WE product peak at a retention time of 41.9 min (arrow). (B) Electron impact mass spectrum of isoprenoid WE product peak. The masses of the parent ion at 590 m/z and fragment ions (365, 311, and 278 m/z) match those reported for the phytanoyl-phytol ester (Rontani et al., 1999. Appl. Environ. Microbiol. 65:221-230).

The structure of the synthesized isoprenoid WE was confirmed by GC-MS. FIG. 7 shows the results of the GC-MS analysis of chloroform extracts of a reaction with WS2 and (Ellman, 1959. Arch. Biochem. Biophys. 82:70-77). The specific activities of WS1, WS2, and *Acinetobacter* WS/DGAT were measured with palmitoyl-CoA and hexadecanol, palmitoyl-CoA and phytol, and phytanoyl-CoA and phytol. Phytanoyl-CoA for these assays was enzymatically synthesized from phytanic acid and CoA using the above-characterized isoprenoid/acyl-CoA synthetase Acs2. Approximately 5 mM phytanoyl-CoA was purified by preparative HPLC, which was used to determine the specific activity of the most active *Marinobacter* enzyme WS2 (Table 3). Because the *Acinetobacter* WS/DGAT did not show activity with phytanic acid and phytol in the coupled enzyme assay, its specific activity with phytanoyl-CoA and phytol was not measured.

TABLE 3

Spectrophotometric analysis of the specific activities of *Marinobacter* sp. strain 8798 WS1 and WS2 and *Acinetobacter* WS/DGAT

| | Mean sp act (mmol min$^{-1}$ mg$^{-1}$) ± SD of: | | |
|---|---|---|---|
| | *Marinobacter* | | *Acinetobacter* |
| Substrate | WS1 | WS2 | WS/DGAT |
| Palmitoyl-CoA (C$_{16}$) + hexadecanol (C$_{16}$) | 1.338 ± 0.5 | 61.323 ± 1.79 | 0.389 ± 0.039 |
| Palmitoyl-CoA (C$_{16}$) + phytol | 0.152 ± 0.011 | 28.872 ± 2.13 | 0.138 ± 0.003 |
| Phytanoyl-CoA + phytol | ND$^a$ | 0.397 ± 0.099 | ND |

$^a$ND, not determined.

As shown in Table 3, WS2 was more active than either of the other two enzymes tested. The specific activity of WS2 measured with palmitoyl-CoA and hexadecanol as substrates was 61 mmol mg$^{-1}$ min$^{-1}$ versus 1.3 mmol mg$^{-1}$ min$^{-1}$ for WS1 and 0.38 mmol mg$^{-1}$ min$^{-1}$ for *Acinetobacter* WS/DGAT. WS2 was 20-fold more active than WS1 or *Acinetobacter* WS/DGAT in creating the hybrid WE using palmitoyl-CoA and the isoprenoid alcohol phytol as substrates. WS2 activity with phytanoyl-CoA and phytol was determined to be 0.397 mmol mg$^{-1}$ min$^{-1}$.

The kinetic constants of WS2 with palmitoyl-CoA and hexadecanol as substrates were determined under saturating palmitoyl-CoA conditions (at 250 µM) and various concentrations of hexadecanol. WS2 activity followed typical Michaelis-Menten kinetics with a K$_m$ of 44 µM, a V$_{max}$ of 10 mmol mg$^{-1}$ min$^{-1}$, and a k$_{cat}$ of 4,794 s$^{-1}$ (FIGS. 9A and B).

Acyl-CoA and Fatty/Isoprenoid Alcohol Specificity of WS2.

Acyl-CoA and fatty/isoprenoid alcohol specificity of WS2 was determined by using the developed spectrophotometric assay. Acyl-CoA specificity of this enzyme was investigated using acyl-CoAs with various acyl chain lengths (C$_{12}$ to C$_{20}$) and hexadecanol as substrates (FIG. 9C). Long-chain fatty acyl-CoA derivatives arachidoyl-CoA (C$_{20}$) and stearoyl-CoA (C$_{18:0}$) were readily accepted as substrates by WS2, as was the polyunsaturated acyl-CoA linolenoyl-CoA (C$_{18:3}$). Also, WS2 showed a clear preference for palmitoyl-CoA (C16), whereas the shorter acyl-chain substrate myristoyl-CoA (C14) was poorly converted and lauroyl-CoA (C$_{12}$) was not accepted at all by the enzyme.

Figure 9:
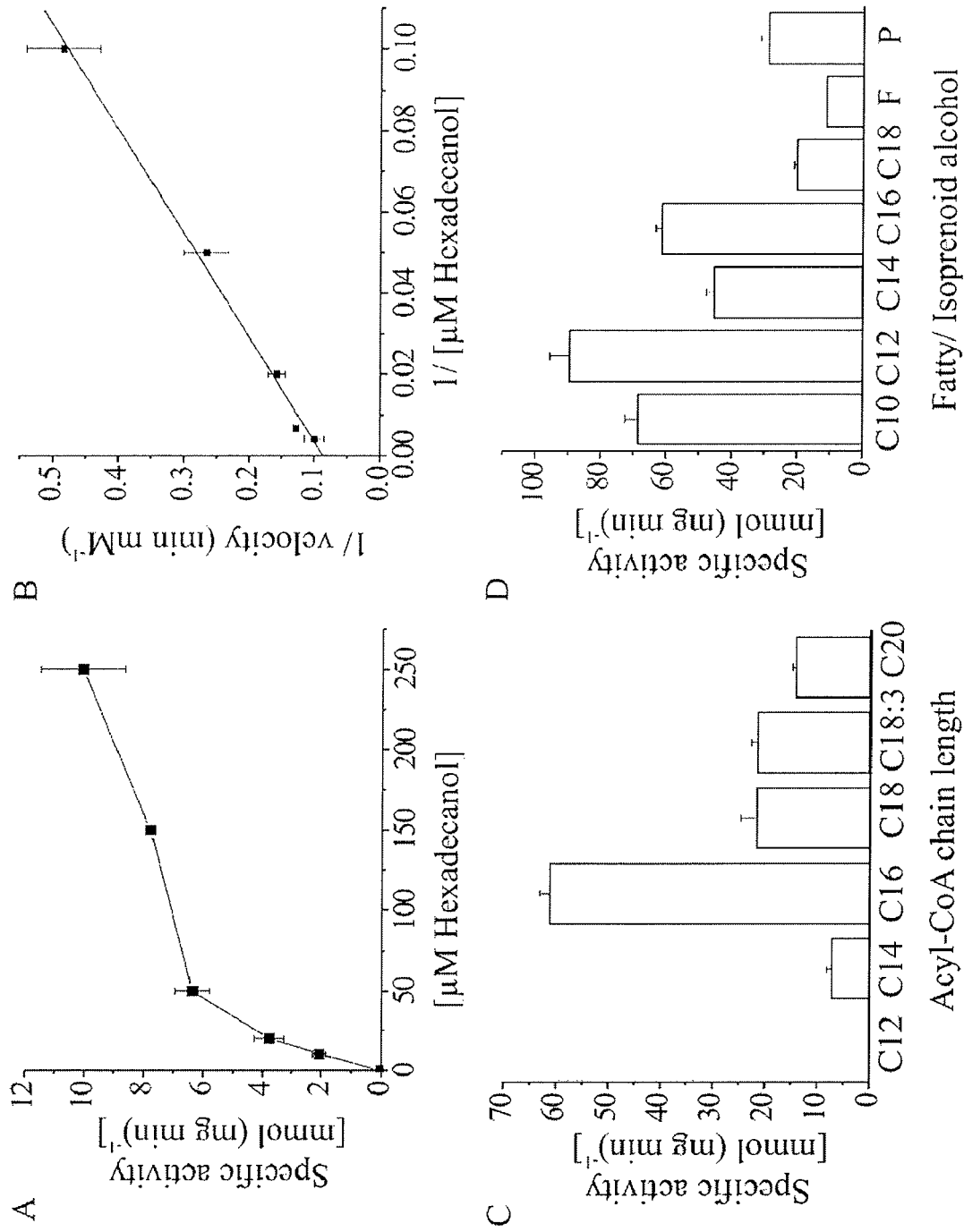
FIG. 9 shows the kinetic measurement of WS2 activity using a spectrophotometric assay. (A and B) Plot of reaction velocity versus hexadecanol concentration (0, 10, 25, 50, 150, and 250_M) with palmitoyl-CoA (250_M) (A) and corresponding double reciprocal plot of WS2 activity (B). (C and D) Comparison of WS2 specific activities for various chain lengths of CoA-activated fatty acids ($C_{12}$ to $C_{20}$) and hexadecanol (C) and various fatty/isoprenoid alcohols ($C_{10}$ to $C_{18}$; F, farnesol, P, phytol) and palmitoyl-CoA (D). Values are averages of three experiments; error bars correspond to one standard deviation.

The relative substrate activity of WS2 was also tested against various fatty/isoprenoid alcohols and palmitoyl-CoA as substrates (FIG. 9D). Compared to WS2's preference for acyl-CoA substrates with medium and long chains, the enzyme displayed a broad activity with alcohols of various chain lengths. Decanol and dodecanol were more readily taken up for WE synthesis than the equivalent-chain-length acyl-CoA carbon chain.

Discussion

*M. hydrocarbonoclasticus* DSM8798 has previously been shown to accumulate isoprenoid WE storage compounds when grown on phytol (Rontani et al., 1999. Appl. Environ. Microbiol. 65:221-230). We hypothesized that the biosynthesis of isoprenoid WE would involve two key enzymes: an isoprenoid acid CoA synthetase and the isoprenoid WS shown in FIG. 1. In the present study, using the draft genome sequence of the very closely related *M. aquaeolei* VT8 (Huu et al., 1999. Int. J. Syst. Bacteriol. 49:367-375; Marquez and Ventosa. 2005. Int. J. Syst. Evol. Microbiol. 55:1349-1351) strain, we identified an isoprenoid-specific CoA synthetase (Acs2) and two isoprenoid WSs (WS1 and WS2) in strain 8798 and characterized their enzymatic activities. These previously undescribed enzymes can synthesize bulky isoprenoid lipids that are chemically similar to their acyl constituents associated with lipid WE biosynthesis (Wältermann and Steinbüchel. 2005. J. Bacteriol. 187:3607-3619).

Isolation of an isoprenoid specific isoprenoid/acyl-CoA synthetase (Acs2) was crucial in the characterization of the isoprenoid WSs since it enabled the synthesis of the commercially unavailable phytanoyl-CoA as a substrate for in vitro enzyme assays. Bulky isoprenoids are usually not accepted as substrates by known acyl-CoA synthetases. Microbial long-chain fatty acid CoA synthetases have been described that utilize unusual acyl acid substrates (Arora et al., 2005. J. Am. Chem. Soc. 127:9388-9389; Olivera et al., 2001. Mol. Microbiol. 39:863-874). For example, a CoA synthetase (FadD6) from a *Mycobacterium* sp. was shown to activate fatty acid derivatives with methyl groups at α or β positions (Arora et al., 2005. J. Am. Chem. Soc. 127:9388-9389; Olivera et al., 2001. Mol. Microbiol. 39:863-874), whereas another enzyme from *Pseudomonas putida* (FadD1) efficiently activates n-phenylalkanoic acids (Arora et al., 2005. J. Am. Chem. Soc. 127:9388-9389; Olivera et al., 2001. Mol. Microbiol. 39:863-874). However, FadD1 from *P. putida*, which among experimentally characterized acyl-CoA synthetases is most similar to Acs2, did not activate phytanic acid, suggesting that Acs2 has an unusual specificity for isoprenoid acids. To our knowledge, CoA activation of phytanic acid only has been described for very-longchain acyl-CoA synthetases from rat and human sources, where they are involved in the metabolism of phytol (Steinberg et al., 2000. J. Biol. Chem. 275: 35162-35169; Watkins et al., 1996. J. Lipid Res. 37:2288-2295).

Two of the three WSs cloned from *M. hydrocarbonoclasticus* (i.e., WS1 and WS2) were capable of synthesizing isoprenoid WE, whereas WS3 did not show activity with any of the acyl or isoprenoid substrates tested. In the first draft genome sequence, WS1 and WS2 were located in two putative alkane degradation gene clusters. In the final genome assembly released while the present study was under review, none of the WS genes are clustered with these alkane-utilizing genes (FIG. 3). This new gene organization is the result of a new assembly of contigs flanked by 100% conserved, inverted transposase sequences. However, it would require PCR amplifications with oligonucleotides specific to regions flanking these transposase sequences and sequencing of the resulting amplification products to decide whether this new assembly is indeed correct. Furthenaore, regions flanked by these transposase sequences may naturally be prone to genomic rearrangements causing strain variations. WS3 is not clustered with any obvious gene functions and may either have an entirely different set of substrates not involved with WE or TAG synthesis or be nonfunctional. The highly conserved acyltransferase domain HHXXXDG (SEQ ID NO:21; Wältermann et al., 2007. Biochemie 89:230-242) found in ADP1 DGAT/WS, WS1, and WS2 and in NRPSs is modified in WS3 (see FIG. 2); substitution of the conserved glycine with alanine may affect the activity of WS3.

Both WS1 and WS2 were found to synthesize isoprenoid WE from phytanoyl-CoA and farnesol or phytol. Long-chain acyl-CoAs (longer than C$_{14}$) were preferred by both enzymes and were esterified with a wide range of fatty alcohols and also isoprenoid alcohols (Table 1). The bulky phytanoyl-CoA, however, was only esterified with equally bulky isoprenoid alcohols. An explanation for the observed unidirectional formation of hybrid ester only from acyl-CoA and isoprenoid alcohol substrates will require details on catalytic mechanism and structure of this only recently characterized class of enzymes.

WS2 displays several orders of magnitude higher activity toward acyl substrates than previously characterized acyl-WS (Daniel et al., 2004. J. Bacteriol. 186:5017-5030; Kalscheuer and Steinbüchel. 2003. J. Biol. Chem. 278:8075-8082; Kalscheuer et al., 2007. J. Bacteriol. 189:918-928; Wältermann et al., 2007. Biochemie 89:230-242) (Table 3). Its specific activity with isoprenoid substrates is comparable to specific activities measured for WS/DGAT ADP1 with acyl substrates, suggesting that WS2 under cellular conditions is able to efficiently synthesize isoprenoid WE storage compounds. Only WS1, which has the highest peptide sequence identity to the characterized ADP1 WS/DGAT, has DGAT activity. WS1 also shows similar activity levels and substrate preferences than ADP1 WS/DGAT (Kalscheuer and Steinbüchel. 2003. J. Biol. Chem. 278:8075-8082; Stöveken et al., 2005. J. Bacteriol. 187:1369-1376) (Table 3).

The differences in substrate selectivities and activities seen in the isoprenoid WSs described here, reported from *Acinetobacter baylyi* ADP1 (Kalscheuer and Steinbüchel. 2003. J. Biol. Chem. 278:8075-8082; Stöveken et al., 2005. J. Bacteriol. 187:1369-1376; Uthoff et al., 2005. Appl. Environ. Microbiol. 71:790-796), and more recently reported from *Alcanivorax borkumensis* (Kalscheuer et al., 2007. J. Bacteriol. 189:918-928) may reflect adaptations to available carbon sources in their respective environments (Rontani et al., 2003. 69:4167-4176; Rontani et al., 1997. Appl. Environ. Microbiol. 63:636-643; Rontani et al., 1999. Appl. Environ. Microbiol. 65:221-230). Identification of additional microbial WE biosynthetic genes will likely yield enzymes with new and interesting substrate selectivities. For example, *Rhodococcus opacus* is known to synthesize WE from phenyldecanoic acid (Alvarez et al., 2002. Microbiology 148:1407-1412) and therefore likely possesses WS and CoA synthetase activity for bulky substrates. Characterization of these enzyme functions not only is important for understanding metabolic processes in microorganisms but also could yield useful enzymes for biocatalytic applications such as the synthesis of novel WE polymers.

Example 2

In Vitro Production of a Fatty Acid Alkyl Ester

Materials and Methods

Protein expression and purification—Cultures (100 ml) of *E. coli* JM109 transformed with pUCmod expressing putative His6-tagged CoA synthetase (Acs2) or Wax ester synthase (WS2) were grown in LB media supplemented with 100 µg of ampicillin/ml at 30° C. overnight in 500-ml unbaffled flasks. The His6 tags were present on the C-terminal end of each protein. Cells were harvested by centrifugation and resuspended in 10 ml of 50 mM Tris-HCl buffer (pH 8). The cells were lysed by sonication (Branson, Danbury, Conn.) on ice using a 30% duty cycle consisting of 10 seconds on and 30 seconds off for 10 cycles. Cell lysates were spun down at a centrifugal force of 13,763 g in 50-ml Oakridge tubes in a Beckman J2-HS floor centrifuge equipped with a JA-17 rotor for 30 min at 4° C. The supernatant was applied to immobilized metal affinity chromatography Talon resin (Clontech, Mountain View, Calif.) and washed with 10 mM imidazole in 50 mM Tris-HCl buffer (pH 8). The purified proteins were eluted with 300 mM imidazole 50 mM Tris-HCl buffer (pH 8). Elutants were desalted with (Amersham, Piscataway, N.J.) PD-10 resin columns to remove excess imidazole. The purified proteins were concentrated to 1 ml using Vivaspin (Vivascience, Hannover, Germany) 10,000-Da columns. Protein concentrations were determined by using the bicinchoninic acid protein assay method with bovine serum albumin as a protein standard (Pierce Biotechnology, Inc., Rockford, Ill.).

In vitro coupled assays/TLC analysis—Stock solutions of various fatty acid substrates (oleic acid) were prepared in 50 mM Tris-HCl buffer (pH 8) containing 1% gum arabic, 12.5 g bovine serum albumin/ml, 0.1% taurocholate, and 100 mM of fatty acid. WS/Acs enzyme coupled assays were carried out in 500 µL reactions containing 50 mM Tris-HCl buffer pH 8.0, 12.5 µL of fatty acid stock solution and addition of ethyl alcohol solution (final concentrations of each substrate 250 µM), 10 mM MgCl2, 10 mM CoASH, 10 mM ATP, 5 mM TCEP, 0.1 U of inorganic pyrophosphatase, 0.25 µg of Acs2 (acyl CoA synthetase) and 0.5 µg of WS2 (wax ester synthase). Assays were incubated at 37° C. overnight before thin-layer chromatography (TLC) analysis of reaction products. In vitro WS assay samples were extracted with 500 µL of chloroform:methanol (1:1 [vol/vol]), and chloroform:methanol extracts were analyzed by TLC with Whatman normal phase silica gel 60 plates where products were separated using hexane:diethyl ether:acetic acid (90:10:1 [vol/vol/vol]). Products were compared to an ethyloleate standard. Resolved TLC plates were stained with iodine vapor.

Results

Figure 18:
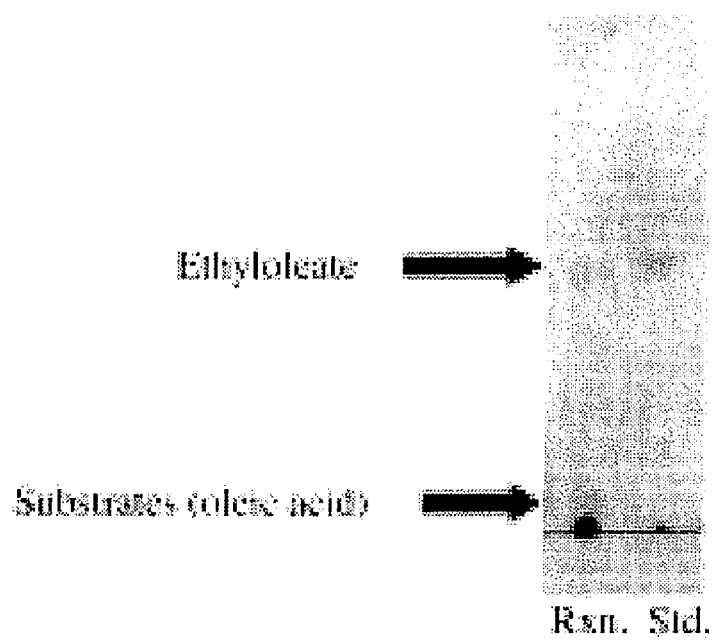
FIG. 18. TLC plate with iodine-stained fatty acid ethyl ester (ethyloleate) products. TLC plate of acs2/WS2-coupled assay reacted with oleic acid and ethanol (rxn; left) compared to an ethyloleate standard (std; right).

A TLC plate of Acs2/WS2-coupled assay reacted with oleic acid and ethanol when compared to an ethyloleate standard (FIG. 18).

Conclusions

Oleic acid was chosen for an in vitro fatty acid substrate because it is one of the major lipids present in *Saccharomyces cerevisiae* yeast. Previous experiments with heterologous expression of a homologous *Acinetobacter* bifunctional WS/DGAT enzyme have shown the production of fatty acid ethyl ester (ethyloleate) in vivo in yeast. In addition, the bifunctional *Acinetobacter* WS/DGAT enzyme also produces triacylglycerols (TAGs) which are unnecessary for producing pure fatty acid ethyl esters as glycerol from TAGs are a waste product in the traditional methods of producing biodiesel. The *Marinobacter* WS2 was also determined to be approximately 150 times more active, in vitro, in producing acyl ester products than *Acinetobacter* WS/DGAT and is expected to have similar activity levels in yeast when substrate production levels are increased.

Example 3

Heterologous Expression of *M. hydrocarbonoclasticus* Wax Ester Synthase (WS2) in *Saccharomyces cerevisiae* YGL035c for the Biosynthesis of the Fatty Acid Ethyl Ester, Ethyloleate Biodiesel is currently being developed as an alternative energy source. It is chemically similar to petroleum-based diesel fuel. The current methods to produce it are by transesterification of triacylglycerols from plant oils. These molecules are monoalkyl esters of long-chain fatty acids with short-chain alcohols such as fatty acid methyl esters (FAMEs) and fatty acid ethyl esters (FAEEs). However, regardless of the numerous environmental benefits, a broader use of biodiesel is held back by excessive farmland required for sufficient production of vegetable oil crops.

Figure 10:
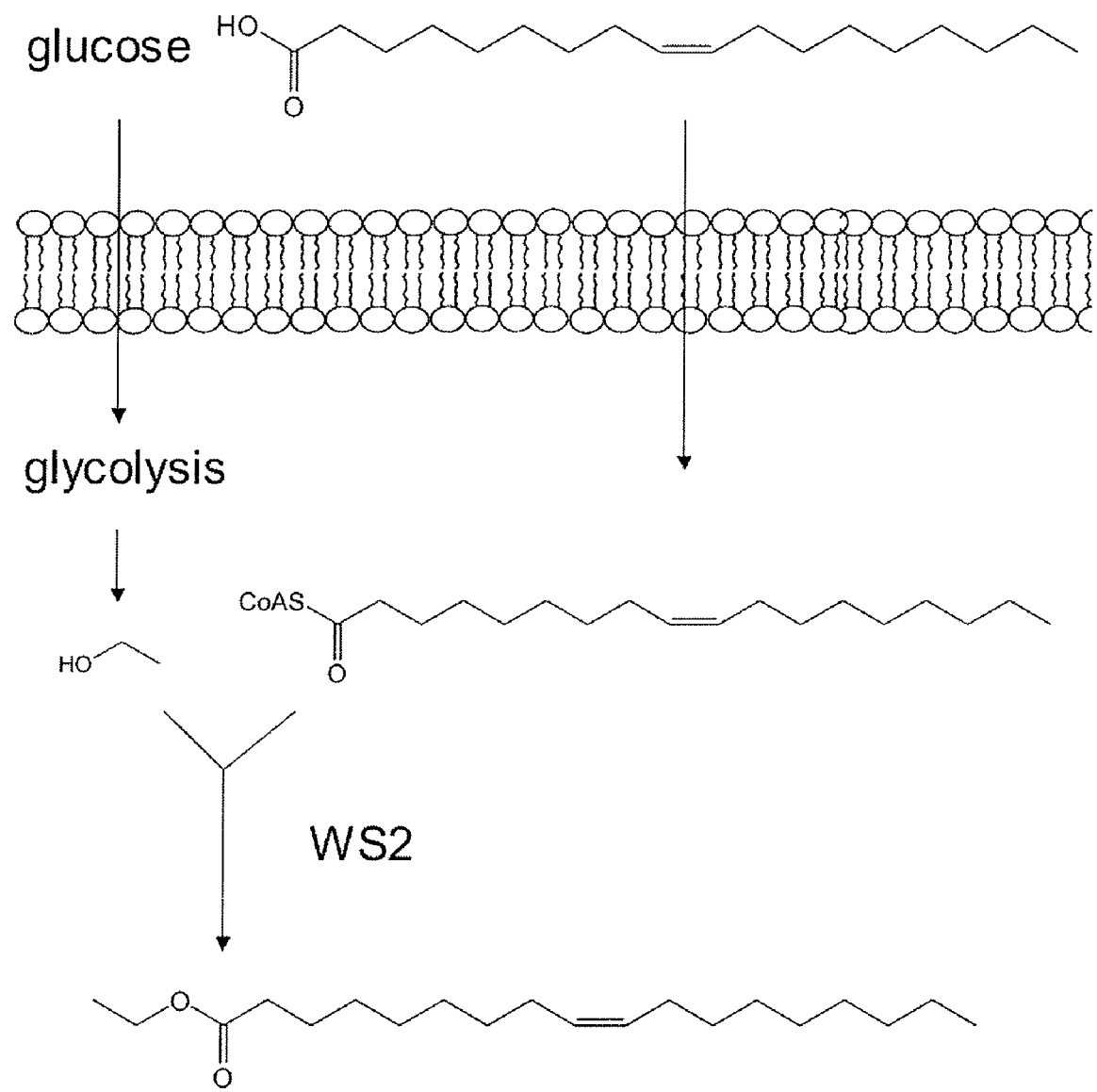
FIG. 10 shows a pathway scheme for synthesis of FAEEs in *S. cerevisiae*. Heterologous expression of wax ester synthase (WS2) in *S. cerevisiae* when given glucose, which is catabolized into ethanol via glycolysis, and oleic acid, which is CoA-activated into oleoyl-CoA, for the production of biodiesel/fatty acid ethyl ester product ethyloleate (bottom).

Therefore, biotechnological processes are needed to enable biodiesel production from more readily available bulk plant materials like sugars or cellulose. In previous work,

*E.coli* that were heterologously expressing ADP1 acyltransferase along with ethanol synthesis genes from *Zymomonas mobilis* were grown on glucose and oleic acid. *Saccharomyces cerevisiae* that are heterologously expressing the acyltransferase from *Marinobacter hydrocarbonoclasticus*, WS2, was grown on glucose and was shown to be more active in vitro and make only wax ester products. Using this approach, FAEEs were formed by *S.cerevisiae* through subsequent esterification of ethanol with coenzyme A-activated oleic acid substrates (FIG. 10). The yeast cells were cultivated under anaerobic conditions fed with glucose and oleic acid. Ethyloleate was the major constituent of FAEE produced. A FAEE content of 5.5% of the cellular dry mass were achieved by flask fermentation.

In this example, the *S. cerevisiae* MIG1 deletion-strain expressed the WS2 acyltransferase downstream from a GAL1 promoter that uses galactose for gene induction. Ethanol is used for an acyl acceptor and oleoyl-CoA as the acyl donor. The expression of WS2 is mediated under the presence of the monosaccharide galactose that would normally be suppressed in a wild type *S. cerevisiae* strain. With glucose present, large pools of pyruvate through the glycolytic pathway are available for the creation of ethanol needed for FAEE synthesis. With high expression of WS2 downstream of GAL1 promoter, a *Saccharomyces cerevisiae* is an efficient host to maximize FAEE production and for optimizing the metabolic reactions involved in manufacturing biodiesel from a cheap, abundant, and renewable sources.

Materials and Methods

*S. cerevisiae* YGL035c BY4742 with following genotype: MATalpha his3Δ1 leu2Δ0 lys2Δ0 ura3Δ0 ΔMIG1 was purchased from ATCC (American Tissue Type Collection; Manassas, Va.). *S. cerevisiae* YGL035c was cultivated for electro transformation in YPG (Yeast peptone glucose) medium at 30° C. overnight. 100 μL of washed yeast cell pellets were electroporated with 5 μL of pESC_URA for the negative control or 5 μL of pESC URA WS2, which expresses acyltransferase gene constructs. Cells were rescued with 800 μL 1M sorbitol and 200 μL were plated onto synthetic minimal media drop out agar plates without uracil. Colonies were seen after 2 days and were picked and grown in nitrogen base medium (Difco Detroit Mich.) 6.7% (wt/vol), and 0.13% (wt/vol), synthetic dropout medium supplement without uracil, and 2% (wt/vol) glucose. One hundred milliliter yeast cultures were grown aerobically overnight at 30° C. in 250 ml flask with synthetic dropout uracil growth media with glucose. Cells were spun down and resuspended in 200 mL of fresh dropout media with 2% glucose, 0.1% potassium oleate, and 2% galactose to induce expression of heterologous protein. Cultures were capped with a rubber stopper with syringe needle piercing the top of the rubber stopper to allow gas (carbon dioxide) to exit during the 72 hours anaerobic growth. Cells were harvested and resuspended in 1 mL of chloroform and approximately 0.5 grams of glass beads. Total lipid composition of yeast was determined from cells harvested from a 200-ml liquid culture, broken with glass-beads in a 50-mL Falcon tube, and extracted into 1.5 mL of chloroform.

Cells were vortexed vigorously for 5 minutes to lyse open cells and chloroform was removed and evaporated under nitrogen gas. 15 mL sample of 250 mL cultures were centrifuged and lysed with glass beads, the yeast lysates were resuspended in 1 ml chloroform for GC/MS analysis and TLC analysis.

TABLE 4

Strains and plasmids used in this study

| Strain or plasmid | Relevant properties | Reference |
|---|---|---|
| *S. cerevisiae* H1246 | MATα are1-Δ::HIS3 are2-Δ::LEU2 dga1-Δ::KanMX4 lro1-Δ:: TRP1 ADE2 ura3 TAG- SE- | Sandager et al. (2002. J. Biol. Chem. 277: 6478-6482) |
| *S. cerevisiae* YGL035c | MATα his3Δ leu2Δ lys2Δ ura3Δ ΔMIG1 | on the world wide web at the *Saccharomyces* Genome database website |
| JM109 | RecA1 supE44 endA1 hsdR17 (r$_K^-$m$_K^+$) gyrA96 relA1 thiΔ (lac-proAB)[F'traD36 proAB+ lacIq lacZΔM15] | Yanisch-Perron et al. (1985. Gene 33: 103-119) |
| pUCmod HisWS2 | Cloning vector Constitutive lac promoter(27), Amp$^r$ N-terminal histidine tagged WS2 | Holtzapple et al. (2007. J Bacteriol 189: 3804-12) |
| PESC-URA::WS2 | *E. coli- S. cerevisiae* shuttle vector; URA3 | Stratagene |

Cloning of WS2 into pESC Vector

For WS2 expression in yeast, the WS2 gene copy was subcloned from pUCmod WS2 using the following primers:

5'-AGTC GGATCCGCCGCCACCATGGCAATGAAACGTCTCGG AACCC-3' (SEQ ID NO:15) introducing a BamHI site (underlined) upstream of the start codon (bold). Reverse primer sequence 5'-AGTCGGTACCTTACTTGCGGGT-TCGGGCG-3' (SEQ ID NO:16) introducing a KpnI site (underlined). The PCR product was subcloned into BamHI-KpnI digested vector pESC-URA collinear to GAL1 promoter inducible by galactose. ATAAGAAT GCGGCCGCACCATGAGCGAAGAAAGCTTATTCGAG TCTTCTCC (SEQ ID NO:17) And PacI site introduced downstream on the reverse oligonucleotide GGGCC TTAATTAATTATTTCAAAGTCTTCAAC (SEQ ID NO:18).

Purification of Recombinant WS2 for In Vitro Assays—

For WS2 protein purification, 100 mL cultures of *E. coli* JM109 transformed with pUCmod expressing N-terminal 6Xhis-WS2 were grown in LB media supplemented with 100 μg/mL of ampicillin at 30° C. overnight in 500 mL unbaffled flasks. Cells were harvested by centrifugation and resuspended in 10 mL of 125 mM sodium phosphate buffer pH 7.2. The cells were lysed by sonication (Branson, Danbury, Conn.) on ice using a 30% duty cycle consisting of 10 seconds on and 30 seconds off for 10 cycles. Cell lysates were spun down at a centrifugal force of 13,763×g in 50 ml Oakridge tubes in a Beckman J2-HS floor centrifuge equipped with a JA-17 rotor for 30 minutes at 4° C. The supernatant was applied to immobilized metal affinity chromatography (IMAC) using Talon Resin (Clontech, Mountain View, Calif.) and washed with 15 mM imidazole in 125 mM sodium phosphate buffer pH 7.2. The purified proteins were eluted with 300 mM imidazole in 125 mM sodium phosphate buffer pH 7.2. Elutants were desalted with (Amersham, Piscataway, N.J.) PD-10 resin columns to remove excess imidazole. The purified proteins were concentrated to 1 mL using Vivaspin (Vivascience, Hannover, Germany) 10,000 Da columns. Protein concentrations were determined using the BCA (bicinchoninic acid) protein assay method using bovine serum albumin (BSA) as a protein standard (Pierce Biotechnology Inc., Rockford, Ill.).

Determination of WS2 Kinetics on Ethanol and Oleoyl-CoA

WS2 activity was measured in a total volume of 200 µL of 125 sodium phosphate buffer (pH 7.2) containing 250 µM ethanol for determination of the WS activity was determined by monitoring CoA release using Ellman's reagent (5,5'-dithio-bis(2-nitrobenzoic acid), DTNB) at 412 nm (e=13,600 $M^{-1} cm^{-1}$). Kinetic in vitro assays were performed in triplicate in 125 mM sodium phosphate buffer pH 7.2 containing, 10 mM $MgCl_2$, 1 mM DNTB, 250 µM oleoyl-CoA, 1-250 mM ethanol and 0.5 µg of WS enzyme. Assay reactions were pre-incubated at 37° C. for 5 minutes before the reactions were started by the addition of enzyme. Substrate concentrations were reversed to measure the kinetics of WS2 with oleoyl-CoA using 250 µM ethanol and 1-250 µM oleoyl-CoA.

Lipid Analysis

Fifteen milliliters of grown yeast were centrifuged for 10 minutes at 4000 rpm. The cell pellets were vortexed vigorously with glass beads for 5 minutes to lyse open cells and extracted with 1 mL chloroform of which 5 µL were spotted on TLC with Whatman normal phase silica gel 60 plates and developed using hexane:diethyl ether:acetic acid (90:10:1, v/v/v). TLC plates were stained with either iodine vapor.

GC and GC/MS Analysis of FAEEs

For quantification of ethyloleate, chloroform extractions of three known amounts (1.5 nmoles, 15 nmoles, and 30 nmoles) of ethyloleate standard were injected into the gas chromatograph (GC) in which the peak areas were integrated to calculate the amounts of ethyloleate produced by YGL035c expressing WS2. Three microliters of chloroform extracts from the samples were injected and analyzed on a gas chromatography electron impact mass spectrometry that were performed with a Hewlett Packard 6890 series gas chromatograph connected to an HP 5973 mass spectrometer. GC conditions consisted of a column (30 m by 0.25 mm ID by 1.5 µm coated with 5% phenyl methyl silicone) with the injector temperature set to 250° C. The oven was set to a temperature gradient of 120° C. for 5 minutes; with an increase of 3° C. $min^{-1}$ to 180° C. increase of 10° C. $min^{-1}$ to 220° C., 220° C. for 30 minutes. Identification of mass fragments FAEE products were compared to an ethyloleate standard (parent ion 310 m/z).

Results

Expression of WS2 in Yeast.

Oleic acid was supplemented to the growth media for the production of FAEE. Production was seen after 48 hours of aerobic growth. Although the ethanol can be aerobically produced in S. cerevisiae from the glucose (called the Crabtree effect), no FAEE product was seen in the cellular extracts from H1246 harboring a constitutively expressed WS2 grown in the presence of oxygen. The constitutive vector contains an ATPAse promoter found on pDR196 vector system. Unfortunately, no FAEE were observed when yeast cultures containing WS2 were grown anaerobically. The constitutive ATPase promoter was thought to be unexpressed when grown anaerobically. To test this theory, green fluorescent protein (GFP) was cloned into the pDR196 constitutive plasmid system and yeast cultures were grown anaerobically for 48 hours after 24 aerobic growth period. Yeast culture were centrifuged and resuspended in 10 mL of PBS pH 7.

Figure 11:
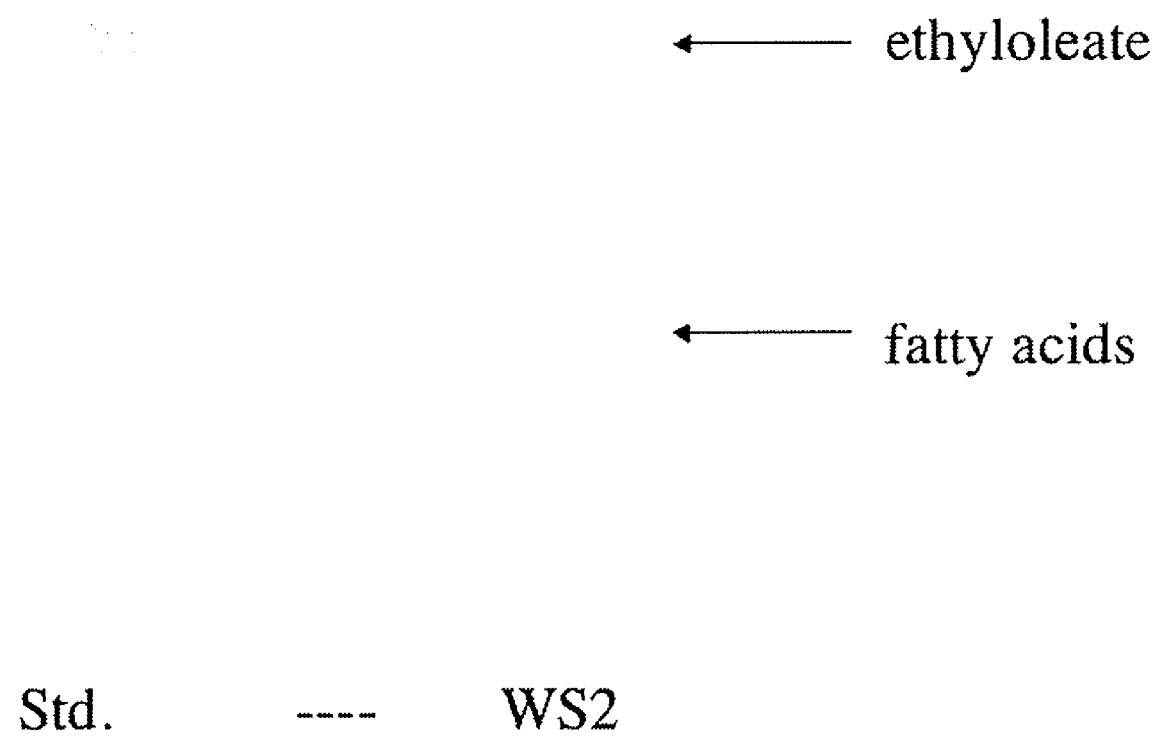
Figure 12:
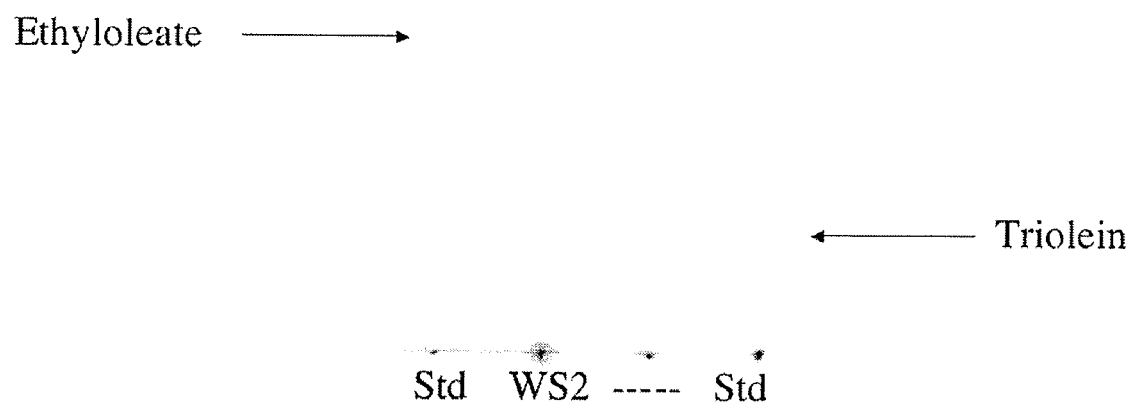
FIG. 12 shows WS2 expression in MIG1 deletion strain of yeast. TLC plate showing the production of the FAEE, ethyloleate, in YGL035c MIG1 deletion *S. cerevisiae* spiked with 0.1% potassium oleate with WS2 gene (labeled WS2) and no ethyloleate produced with empty vector (labeled -----).
Figure 13:
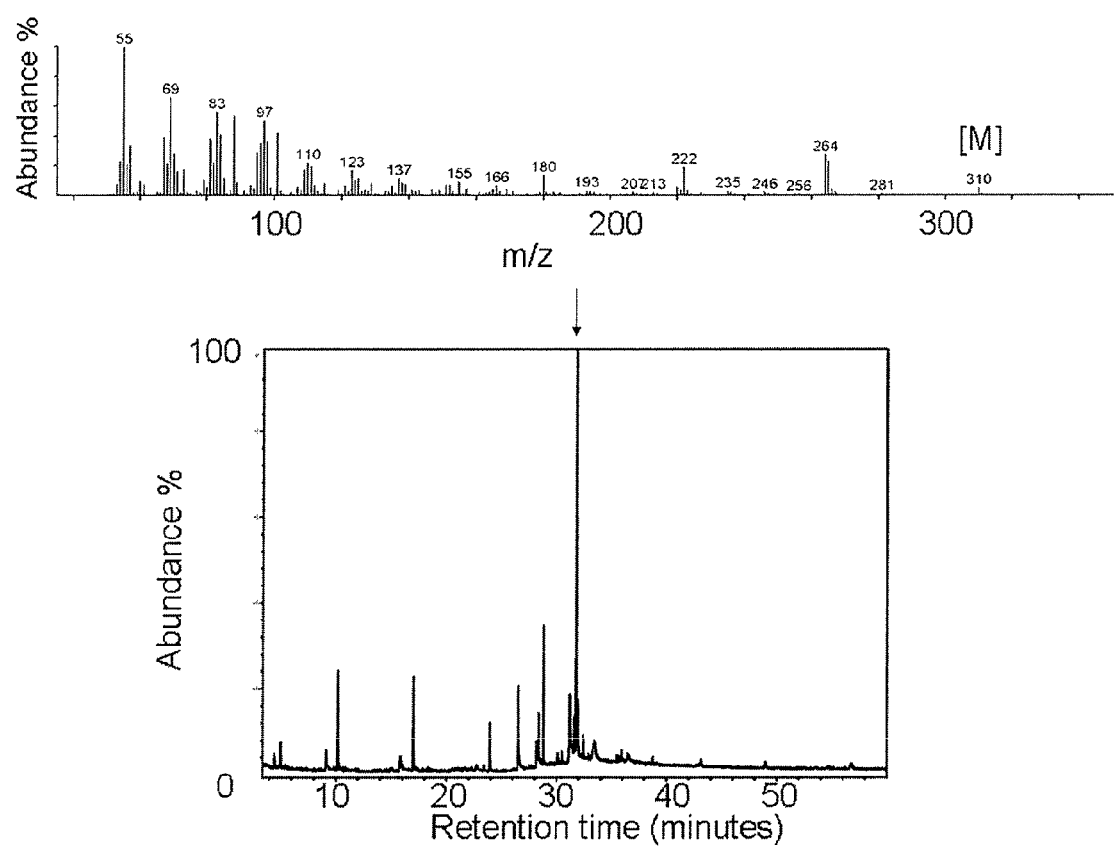
FIG. 13 shows a GC-MS analysis of ethyloleate produced by yeast. GC-MS data showing ethyloleate extracted from *S. cerevisiae* expressing WS2 the retention time was 31.8 minutes (bottom arrow) and the calculated mass [M] of ethyloleate is 310 daltons

Analysis of Neutrals Lipids and FAEEs (FIGS. 11-13)

Thin layer chromatography (TLC) revealed ethyloleate ester product was synthesized in vitro when WS2 was coupled with Acs2 and given oleic acid an ethanol as substrates. TLC also revealed ethyloleate was produced in vivo in H1246 when given both ethanol and oleic acid as substrates. Ethyloleate was also shown in vivo in yeast harboring the Mig1 deletion and expressing the pESC-URA-WS2. WS2 is induced with galactose and was able to synthesize ethanol from glucose when grown anaerobically with exogenous 0.1% potassium oleate. No ethyloleate product was seen on the TLC plates when potassium oleate was not supplemented. In addition, no ethyloleate was seen in the empty pESC-URA plasmid negative control, indicating that WS2 was responsible for the synthesis of ethyloleate product. The only ester products detected by TLC were TAG products that were seen in both WS2-expressing strain and the negative control. In the case of YGL035c, only oleic acid was supplemented as the ethanol could be produced anaerobically by the yeast in the presence of glucose and galactose for GAL-10 induced gene expression. H1246 was tested for production of ethyloleate with galactose for the carbohydrate source and oleic acid present. However no FAEE were detected when grown anaerobically (data not shown). YGL035c was grown with out oleic acid supplemented in the media, which also showed no FAEE product formation (data not shown).

Kinetics of WS2 with Ethanol and Oleoly-CoA- (FIGS. 14, 15)

Kinetic analysis of purified WS2 with ethanol was calculated to be 17 µM and a $v_{max}$ of 1250 µmol $(min/mg)^{-1}$ and a $K_{cat}$ of 58 $s^{-1}$. The $K_m$ for oleoyl-CoA was 23 µM a $v_{max}$ was calculated to be 1667 µmol $(mg/min)^{-1}$ and a $K_{cat}$ of 58 $s^{-1}$. These measurements were performed in triplicate and averaged. The Lineweaver-Burke plot indicates an increase in enzymatic velocity as substrate concentration increases. This increase is not seen with the ethanol Michaelis-Menten plot. The increase in velocity may be due to interfacial activation of WS2. This behavior has been seen with lipases that have a substrate interfacial mechanism where a lid domain "unhinges" at the aliphatic/aqueous interface. Oleoyl-CoA behaves as a detergent and forms micelles during the reaction and as substrate is turned over into FAEEs the solubility decreases. Furthermore, as the substrate concentration is high (over 100 µM) the solubility enhances the activation and turn over of product by WS2. Thus, in comparing the catalytic efficiencies of ethanol and oleoyl-CoA to palmitol (hexadecanol) and palmitoyl-CoA the $K_m$ shows a high binding capacity for ethanol and oleoyl-CoA but the turn over rate is several fold lower compared to the native substrates (palmitoyl-CoA and hexadecanol) of WS2.

TABLE 5

Steady state kinetic analysis of WS2 in vitro on ethanol and oleoyl-CoA

|  | Oleoyl-CoA | Ethanol |
|---|---|---|
| Km | 23 μM | 17 μM |
| Vmax | 1667 μmol (mg/min)$^{-1}$ | 1250 μmol (mg/min)$^{-1}$ |
| Kcat | 59 s$^{-1}$ | 32 s$^{-1}$ |
| Kcat/Km | 2.56 × 10$^6$ (M$^{-1}$ s$^{-1}$) | 1.88 × 10$^6$ (M$^{-1}$ s$^{-1}$) |

Figure 16:
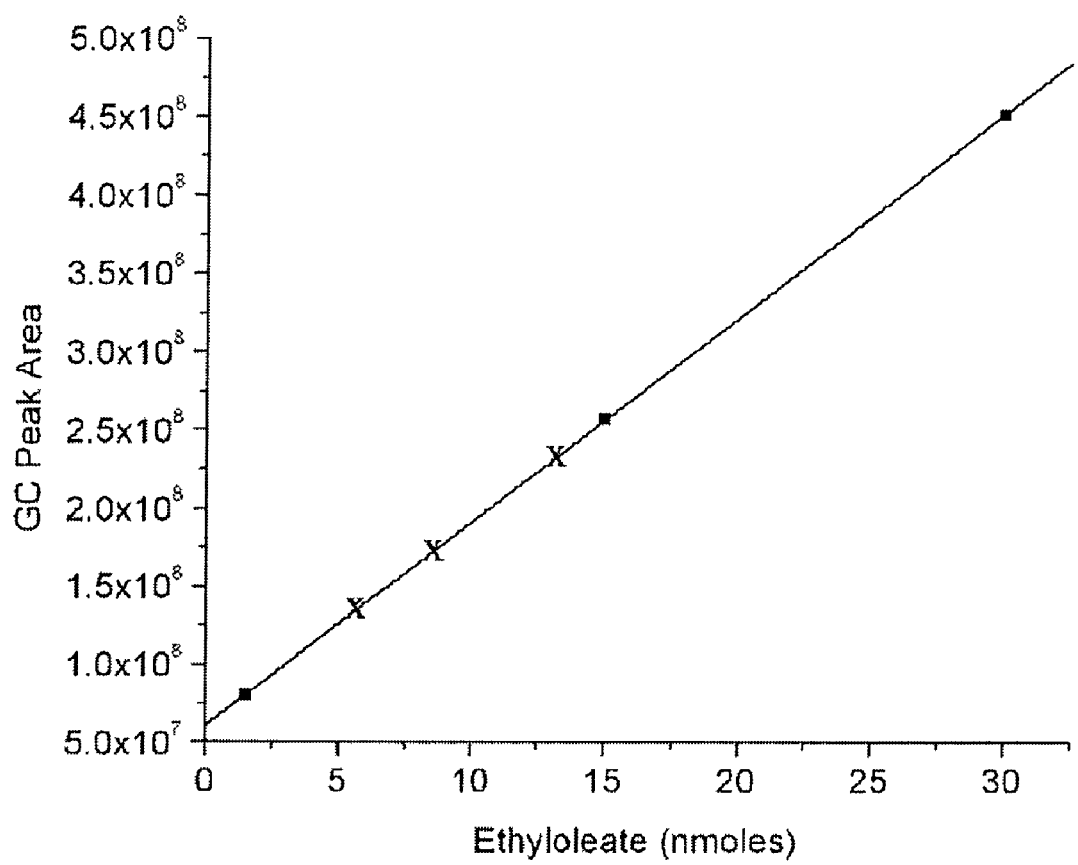
FIG. 16 shows a standard curve of integrated FAEE peaks from GC analysis. Standard ethyloleate standard curve of integrated GC peak areas used for calculation of ethyloleate yields of FAEE produced in vivo (marked with "x"). The curve displays a slope of three known amounts of ethyloleate injected onto GC 1.5 nanomoles, 15 nanomoles, and 30 nanomoles (marked with "■").

Production Yields of Neutral Lipids in YGL035c Expressing WS2 (FIG. 16).

Yeast cultures were grown in batch culture shake flask fermentation to calculate the absolute yield of ethyloleate that could be synthesized in *S. cerevisiae* YGL035c compared with and without WS2 expression. No ethyloleate was detected by thin layer chromatography in YGL035c without WS2 gene present (empty pESC vector). The cultures were grown in the presence of glucose aerobically for 24 hours at 30° C. and then transferred to media with galactose and glucose in the culture. The flasks were capped with rubber stopper and grown anaerobically at 30° C. The recombinant yeast showed that it was feasible to create FAEEs anaerobically with GAL1 induction of WS2.

TABLE 6

Efficiency of oleic acid converted into ethyloleate

| Total ethyloleate produced in a 250 mL culture (μM) | % Efficiency oleate to ethyloleate |
|---|---|
| 49.36 ± 20.49 | 5.5 |

TABLE 7

Percentage dry weight of total lipid produced by YGL035c

| Sample (averaged triplicate) | Cellular Dry weight (mg) | Total neutral lipid weight (mg) | % weight |
|---|---|---|---|
| YGL035c with WS2 | 38.8 ± 13.5 | 2.1 ± 0.46 | 5.6 ± 1.28 |
| YGL035c empty vector | 36.1 ± 11.3 | 1.53 ± 0.48 | 4.7 ± 0.47 |

The calculated production of ethyloleate in yeast was quantified by integrating the peak areas of known concentration of ethyloleate dissolved in chloroform on the GC. The peak area of the cellular extracts taken form yeast expressing WS2 was compared to a stand curve. The efficiency of converting oleate into ethyloleate was calculated to be 5.5%. This yield was based on the amount of oleate added to the culture 0.1% (wt/vol) added to a 250 mL volume (889 μmoles) that was converted into approximately 50 μmol of ethyloleate. The percent dry weight of cells was also calculated and also compared the total neutral lipids (both TAGs and/or ethyl oleate) that were chloroform extracted from dried cell pellets and compared to the total cell dry weight. The percent yield of neutral lipids (including FAEEs) was 5.5% of the total cell weight compared to the negative control, which was calculated to be 4.7%. The cellular dry mass of negative control was 36.1 mg per 50 mL of liquid culture and 38.8 mg per 50 mL in the WS2 expressing yeast.

Discussion

In this report, fatty acid ethyl esters (FAEE) were synthesized in a Mig1p deletion (YGL035c) strain of *Saccharomyces cerevisiae*. FAEE were made through heterologously expressing a microbial wax ester synthase (WS2) from the previously described *M. hydrocarbonoclasticus* DSM 8798 strain using a galactose promoter system. WS2 is capable of synthesizing only wax ester products rather than TAGs products that are produced by the bifunctional WS/DGAT from *Acinetobacter baylyi* ADP1. Attempts at making neutral lipids with yeast were previously performed using a TAG-phenotype strain of *Sacchromyces cerevisiae* H1246 (Dahlqvist et al., 2000. PNAS 97:6487-6492; Kalscheuer et al., 2004. Appl Environ Microbiol 70:7119-25; Sandager et al., 2002. J. Biol. Chem. 277:6478-6482).

The yield of ethanol in yeast has been reported to be as high as 10% (wt/vol) of an optimally grown fermentation. However with our initial anaerobic growth conditions, it is estimated that the ethanol concentrations is considerably less than 10%. Therefore this may contribute to the low yields of FAEEs seen with our experiments. Future experiments should monitor ethanol yields (via GC analysis) and optimize fermentation condition to produce as high yield of ethanol as possible.

A highly expressed, constitutive expression system using pDR196 and pDRf1 shuttle plasmids, which uses an ATPase constitutive promoter upstream of WS2 in the TAG deficient H1246 *S. cerevisiae* strain would allow the use of glucose for creation of more ethanol and avoid using galactose for GAL-dependent promoter systems. This would create higher yields of ethanol. However, the expression using a constitutive promoter was compromised possibly with expression of WS2 under anaerobic conditions as the control experiment using GFP induction showed little to no gene-expression under anaerobic conditions.

Therefore, a strong gene induction system using a GAL promoter system in the MIG1 deletion strain would increase yields of FAEE as this strain grew to higher cell densities compared to H1246. However, the low conversion rate of oleate into ethyloleate (5.5%) may be due to the production of ethanol rather than the uptake of oleate or the activity of WS2. The molar equivalence is roughly 1 ethanol molecule for every 10 oleate molecules based on percent weight. Yeasts are known to produce an excess of 10% ethanol (wt/vol) if grown under optimal conditions (Jacques et al., 2003. The Alcohol Textbook 4th Edition, 4th ed. Nottingham University Press, Nottingham, NG110AX, United Kingdom). The ethanol production level calculated to be less than 1% may reflect why the production of FAEE is low. In addition to available substrates, the calculated efficiency of WS2 in respect to oleoyl-CoA and ethanol was also rather low in comparison to the palmitoyl-CoA and hexadecanol; this may also attribute to the low turnover of supplemented oleate into ethyloleate. Growing the cells in a batch fermentation for FAEE production rather than shaker flask would also help in creating more FAEE product. However WS2 does show promiscuous activity for the biotechnological production of neutral lipids (Holtzapple and Schmidt-Dannert. 2007. J Bacteriol 189: 3804-12).

The kinetic measurements of WS2 against oleoyl-CoA and ethanol showed high activity in vitro. However, there are no measurements that were performed against these substrates with WS/DGAT to see whether a metabolic "bottleneck" was occurring in converting ethanol and oleoyl-CoA into ethyloleate.

Example 4

Optimization of Biosynthesis of the Fatty Acid Ethyl Ester, Ethyloleate

In this example yeast strains are used that produce high amounts lipids (i.e. *Yarrowia lipolyticum*) (Fickers et al., 2005. FEMS Yeast Res 5:527-43; Gaspar et al., 2007. Biochim Biophys Acta. 1771:241-54). The de novo synthesis of fatty acids could be generated using other prokaryotic hosts strains. Kalscheuer et al. (Kalscheuer et al., 2006. Microbiology 152:2529-36) recommended the use of Gram positive bacteria (Talarico et al., 2005. Microbiology 151:4023-4031) such as *actinomyces; Streptomyces* species that are capable of synthesizing large amount of fatty acids (Olukoshi and Packter. 1994. Microbiology 140:931-43; Packter and Olukoshi. 1995. Arch Microbiol 164:420-7). The genes responsible for ethanol production could be heterologously expressed using ethanol synthesis genes from *Zymomonas mobilis* (Ingram et al., 1989. Efficient Ethanol—Production from Xylose, Lactose and Glucose by Recombinant *Escherichia-Coli*. Abstracts of Papers of the American Chemical Society 198: 29-MBTD). However, the expression of ethanol synthesis genes may require introduction into a non-ethanol producing species. In previous investigations, FAEE has been synthesized in *E. coli* with addition of an ethanol synthetic pathway from *Zymomonas mobilis* strain capable of making ethanol aerobically.

Genetic manipulations of the YGL035c strain for FAEE production, WS2 may be integrated into the yeast chromosome, which would allow a more stable approach to synthesizing FAEES where a complex media could be used rather than a synthetic dropout media that is traditionally used for expression of episomal, heterologously expressed genes in yeast. In Kalsheuer's report, supplementing the medium with exogenous fatty acids made FAEEs; De novo fatty-acid biosynthesis by *E. coli* does not provide sufficient acyl substrates for WS/DGAT-mediated FAEE synthesis, indicating that this microorganism may not be the ideal 'platform' for biodiesel production. Substantial FAEE biosynthesis can be achieved that is not dependent on the addition of exogenous fatty acids to the yeast culture.

Figure 17:
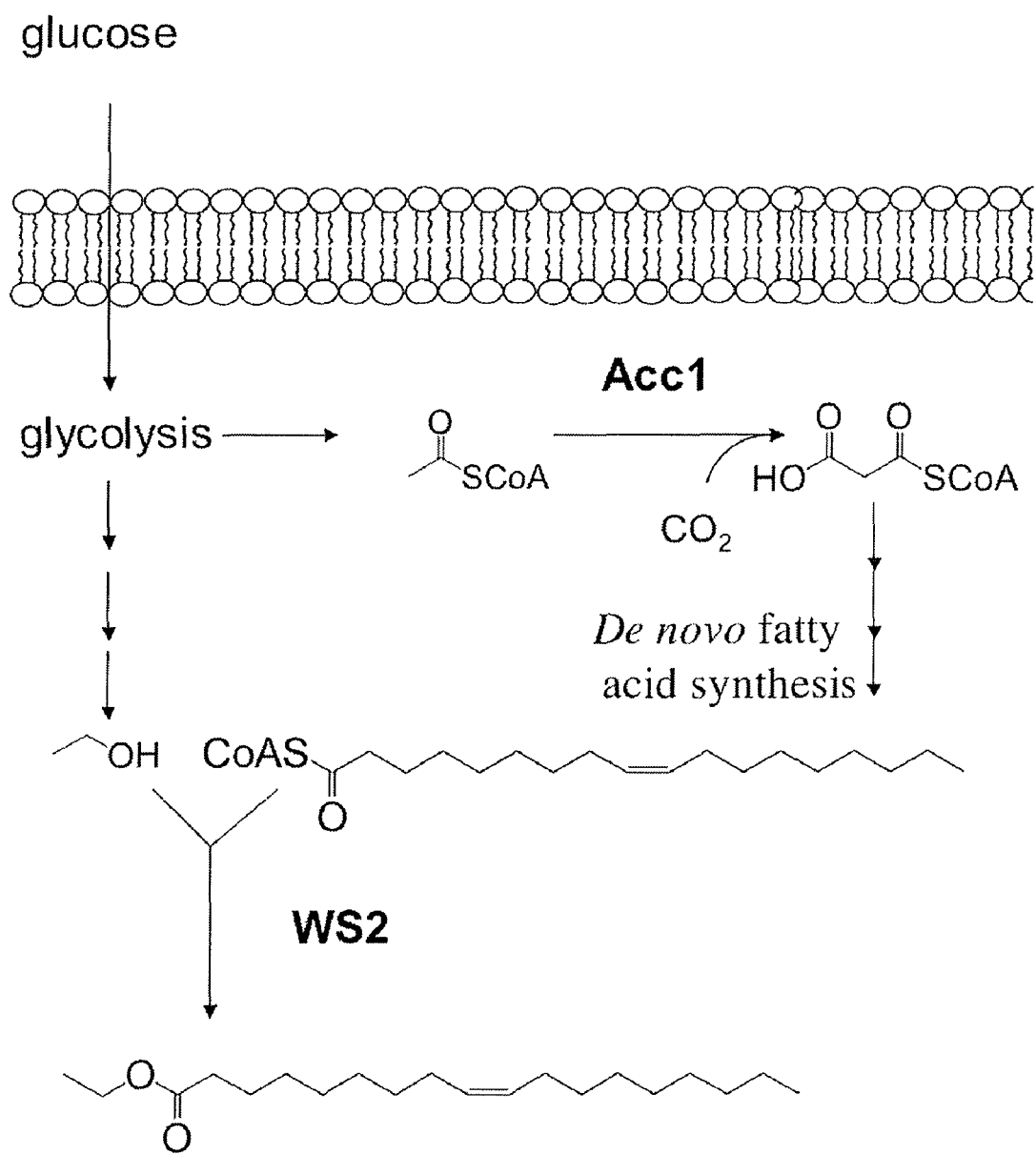
FIG. 17 shows a metabolic pathway in YGL035c with the coexpression of WS2 and ACC1 under GAL induction. *S. cerevisiae* YGL035c grown on glucose as the sole carbon source for the production of biodiesel. Ethanol can be produced via glycolysis as well as acetyl-CoA for the precursor substrates needed for making FAEE via WS2. The proposed pathway of the fatty acid ethyl ester pathway using a GAL10-induced acetyl-CoA carboxylase (Acc1) to create pools of malonyl-CoA for higher yields of fatty acetyl-CoA.

For enhanced FAEE production, up-regulation of the acetyl-CoA carboxylase (Acc1) enzyme can be manipulated either on the chromosome or on a GAL-inducible episomal system. Acc1 is a biotin-containing enzyme that catalyzes the carboxylation of acetyl-coA to malonyl-CoA. In bacteria, this reaction is performed by a heterotetramer (Acc1 A-D) but in eukaryotes such as yeast the reaction is carried out by one multi-complexes monomer protein (Stryer, 1988. Biochemistry 3rd Edition. W.H. Freeman And Company (NY):481-485). This reaction is believed to be an important regulatory step in fatty acid biosynthesis in animals, bacteria, and plants (Akoh et al., 2007. J Agric Food Chem 55:8995-9005; Antoni et al., 2007. Appl Microbiol Biotechnol 77:23-35; Canoira et al., 2006. Biomass and Bioenergy 30:76-81; Carvalhal et al., 1996. Revista De Microbiologia 27:263-267). Two partial reactions are involved in this process: 1) carboxylation of an enzyme-bound biotin molecule, and 2) transfer of the carboxyl group to acetyl-coA. Thus, by over expressing the first step devoted to de novo fatty acid synthesis in *Sacchromyces*, substantial pools of malonyl-CoA can be made for fatty acyl chain elongation. With more expressed Acc1, all the glucose fed to yeast can be converted into precursors for FAEES in the form of CoA-activated fatty acids and ethanol derived from glucose (FIG. 17). Therefore, it is likely that oleic acid would not need to be supplemented as in other methods of producing biodiesel-using WS/DGAT.

In addition to upregulated expression of ACC1, media can also be supplemented with the cofactor biotin (vitamin H). *S. cerevisiae* is auxotrophic for biotin synthesis and must actively transport this cofactor from the environment (Stolz et al., 1999. J Biol Chem 274:18741-18746). High concentrations (>2 µg/mL) may be needed for yeast strongly expressing ACC1 to create high yields of malonyl-CoA, as biotin is an essential cofactor for the carboxylation of acetyl-CoA substrates.

In addition to biotin being a possible limiting factor for Acc1p activity, one should also consider the amount of available ATP, as ATP is also required for malonyl-CoA production. This was addressed when a transgenic *Solanum tuberosum* was engineered for higher levels of ATP synthesis there was an increase in plastidic ATP content, which resulted in increased amounts of starch in transgenic potato tubers (Geigenberger et al., 2001. Plant Physiol 125:1667-78; Tjaden et al., 1998. J Biol Chem. 273:9630). However, the strain of potatoes with higher amounts of ATP pools did not alter the amount of TAGs that were produced (Klaus et al., 2004. Planta 219:389-96). Therefore, the amount of ATP seems to be not limiting for fatty acid synthesis.

Furthermore, previous investigations have made attempts in manipulating pools of malonyl-CoA in a photosynthetic system for production of more neutral lipids. An example is the transformed potato, *Solanum tuberosum*, with a copy of the *Arabidopsis thaliana* ACC1, containing a strong CaMV (cauliflower mosaic virus) promoter was used to express large amounts of Acc1 protein (Klaus et al., 2004. Planta 219:389-96). The results indicated that over-expression of ACC1 increased the production of malonyl-CoA. The larger pool of malonyl-CoA resulted in a five-fold increase in neutral lipids (Klaus et al., 2004. Planta 219:389-96). The Acc1p from the diatom *Cyclotella cryptica* has also been investigated for enhanced triacylglycerol accumulation (Dunahay et al., 1996. Appl Biochem Biotechnol 57/58:223-231). The WS2 microbial wax ester acyltransferases may also be heterologously expressed in a photosynthetic host where FAEES products could be produced rather than TAGs. Creating a photosynthetically derived biodiesel product from $CO_2$ may be an efficient way of making an energy dense liquid fuel (Chisti, 2008. Trends Biotechnol 26:126-31).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An isolated polypeptide having isoprenoid wax ester synthase activity, wherein said polypeptide comprises an amino acid sequence having at least 95% sequence identity to SEQ ID NO: 2.

2. A genetically modified microbe comprising an exogenous polynucleotide, wherein the exogenous polynucleotide encodes the isolated polypeptide of claim 1.

3. The genetically modified microbe of claim 2 wherein the microbe is a yeast.

4. A method comprising:
   providing the genetically modified microbe of claim 2; and
   incubating the microbe under conditions suitable for the production of an ester.

5. The method of claim 4 further comprising isolating the ester.

6. The method of claim 4 wherein the ester comprises a fatty acid ethyl ester.

7. The method of claim 4 wherein the ester comprises a fatty acid methyl ester.

8. The method of claim 4 wherein the ester comprises an alcohol-derived group of $C_1$ or $C_2$.

9. The method of claim 4 wherein the ester comprises a fatty acid-derived group of at least $C_8$.

10. The method of claim 4 wherein the fatty acid-derived group is unsaturated.

11. The method of claim 4 wherein the ester is palmityl oleate.

12. The method of claim 4 wherein the microbe is a yeast.

13. The method of claim 4 wherein the microbe is a prokaryotic microbe.

14. The method of claim 4 wherein the genetically modified microbe further comprises an exogenous polypeptide having isoprenoid acyl CoA-synthetase activity, wherein said polypeptide comprises an amino acid sequence having at least 95% sequence identity to SEQ ID NO: 4.

15. The isolated polypeptide of claim 1 wherein the amino acid sequence of the isolated polypeptide comprises the amino acid sequence of SEQ ID NO:2.

16. The isolated polypeptide of claim 1 wherein the specific activity of the isolated polypeptide is at least 20 mmo $mg^{-1}$ $min^{-1}$ when measured with palmitoyl-CoA and hexadecanol as substrates.

17. The genetically modified microbe of claim 3 wherein the yeast is in the order Saccharomycetales.

18. The genetically modified microbe of claim 17 wherein the yeast is *Saccharomyces cerevisiae*.

19. The genetically modified microbe of claim 2 wherein the microbe is a bacterium.

20. The genetically modified microbe of claim 19 wherein the bacterium is *Acinetobacter baylyi* or *E. coli*.

21. The isolated polypeptide of claim 1 when expressed in a microbe, produces triacylglycerols in an amount no greater than 0.5% of cellular dry weight in said microbe.

* * * * *